(12) United States Patent
Brooks et al.

(10) Patent No.: US 12,420,116 B2
(45) Date of Patent: Sep. 23, 2025

(54) METHODS AND SYSTEMS FOR USING AND CONTROLLING HIGHER DOSE RATE IONIZING RADIATION IN SHORT TIME INTERVALS

(71) Applicant: IntraOp Medical Corporation, Sunnyvale, CA (US)

(72) Inventors: Kenneth W. Brooks, Windermere, FL (US); James A. Nelson, Newark, CA (US); Derek T. DeScioli, San Jose, CA (US); Christopher J. Patane, San Mateo, CA (US); Donald A. Goer, Sunnyvale, CA (US)

(73) Assignee: IntraOp Medical Corporation, Sunnyvale, CA (US)

( * ) Notice: Subject to any disclaimer, the term of this patent is extended or adjusted under 35 U.S.C. 154(b) by 443 days.

(21) Appl. No.: 17/642,554

(22) PCT Filed: Sep. 9, 2020

(86) PCT No.: PCT/US2020/049925
§ 371 (c)(1),
(2) Date: Mar. 11, 2022

(87) PCT Pub. No.: WO2021/050535
PCT Pub. Date: Mar. 18, 2021

(65) Prior Publication Data
US 2022/0323793 A1  Oct. 13, 2022

Related U.S. Application Data

(60) Provisional application No. 62/986,104, filed on Mar. 6, 2020, provisional application No. 62/900,505, filed on Sep. 14, 2019.

(51) Int. Cl.
A61N 5/10 (2006.01)
(52) U.S. Cl.
CPC ......... *A61N 5/1067* (2013.01); *A61N 5/1071* (2013.01); *A61N 5/1077* (2013.01)
(58) Field of Classification Search
None
See application file for complete search history.

(56) References Cited

U.S. PATENT DOCUMENTS

| 3,201,065 A | 8/1965 | Dunn |
| 3,391,881 A | 7/1968 | Maltby |

(Continued)

FOREIGN PATENT DOCUMENTS

| EP | 0 838 844 B1 | 7/2003 |
| GB | 2 127 173 A | 4/1984 |

(Continued)

OTHER PUBLICATIONS

PCT/US2018/030897, Intraop Medical Corporation, International Search Report and Written Opinion, dated Sep. 6, 2018, 12 pgs.

(Continued)

*Primary Examiner* — Eliza W Osenbaugh-Stewart
(74) *Attorney, Agent, or Firm* — Kagan Binder, PLLC

(57) ABSTRACT

The present invention provides strategies to use and control the delivery of ionizing radiation to carry out therapeutic and industrial irradiation treatments. The present invention uses partial pulse control, component selection, and/or component configuration strategies in order to accurately monitor and terminate irradiation. The strategies are particularly useful to control dosing in the high dose rate and short time scales associated with FLASH technology.

42 Claims, 17 Drawing Sheets

(56) References Cited

U.S. PATENT DOCUMENTS

| | | |
|---|---|---|
| 3,651,360 A | 3/1972 | Sommeria |
| 3,820,035 A | 6/1974 | Meddaugh |
| 3,852,610 A | 12/1974 | McIntyre |
| 4,131,799 A | 12/1978 | Stieber |
| 4,627,089 A | 12/1986 | Menor et al. |
| 4,638,814 A | 1/1987 | Spanswick |
| 4,882,741 A | 11/1989 | Brown |
| 4,891,767 A | 1/1990 | Rzasa et al. |
| 4,995,087 A | 2/1991 | Rathi et al. |
| 5,072,123 A | 12/1991 | Johnsen |
| 5,321,271 A | 6/1994 | Schonberg et al. |
| 5,326,967 A | 7/1994 | Herrmann et al. |
| 5,418,372 A | 5/1995 | Schonberg et al. |
| 5,661,377 A | 8/1997 | Mishin et al. |
| 5,745,545 A | 4/1998 | Hughes |
| 5,933,523 A | 8/1999 | Drisko et al. |
| 6,076,005 A | 6/2000 | Sontag et al. |
| 6,078,036 A | 6/2000 | Cook et al. |
| 6,087,664 A | 7/2000 | Gripp et al. |
| 6,118,847 A | 9/2000 | Hernandez-Guerra et al. |
| 6,137,893 A | 10/2000 | Michael et al. |
| 6,346,966 B1 | 2/2002 | Toh |
| 6,362,875 B1 | 3/2002 | Burkley |
| 6,554,452 B1 | 4/2003 | Bourn et al. |
| 6,690,965 B1 | 2/2004 | Riaziat et al. |
| 6,864,633 B2 | 3/2005 | Trail et al. |
| 6,871,993 B2 | 3/2005 | Hecht |
| 7,339,320 B1 | 3/2008 | Meddaugh et al. |
| 7,400,093 B2 | 7/2008 | Salop et al. |
| 7,894,649 B2 | 2/2011 | Fu et al. |
| 8,111,025 B2 | 2/2012 | Whittum et al. |
| 8,198,587 B2 | 6/2012 | Whittum et al. |
| 8,269,197 B2 | 9/2012 | Goer et al. |
| 8,719,398 B2 | 5/2014 | Qian et al. |
| 8,791,437 B2 | 7/2014 | Felici et al. |
| 8,853,636 B2 | 10/2014 | Perkins |
| 9,030,134 B2 | 5/2015 | Whittum et al. |
| 9,040,945 B1 | 5/2015 | Hayman |
| 9,257,253 B1 | 2/2016 | Allen et al. |
| 9,308,395 B2 | 4/2016 | Adler, Jr. et al. |
| 9,393,439 B2 | 7/2016 | Goer |
| 9,746,581 B2 | 8/2017 | Whittum et al. |
| 9,757,593 B2 | 9/2017 | Adler et al. |
| 9,855,445 B2 | 1/2018 | Mansfield |
| 10,071,264 B2 | 9/2018 | Liger |
| 10,092,774 B1 | 10/2018 | Vanderstraten et al. |
| 10,183,179 B1 | 1/2019 | Smith et al. |
| 10,245,448 B2 | 4/2019 | Heese |
| 10,307,618 B2 | 6/2019 | Mansfield |
| 10,485,993 B2 | 11/2019 | Goer et al. |
| 11,135,449 B2 | 10/2021 | Johnson et al. |
| 11,285,341 B2 | 3/2022 | Goer et al. |
| 2001/0042841 A1 | 11/2001 | Lyons et al. |
| 2007/0003874 A1 | 1/2007 | Yang |
| 2007/0102651 A1 | 5/2007 | Yang |
| 2008/0131312 A1 | 6/2008 | Kang et al. |
| 2009/0054318 A1 | 2/2009 | Kanegasaki et al. |
| 2009/0126760 A1 | 5/2009 | Banerjee et al. |
| 2009/0254154 A1 | 10/2009 | De Taboada et al. |
| 2009/0296885 A1 | 12/2009 | Boeh et al. |
| 2009/0314590 A1 | 12/2009 | Dagh et al. |
| 2010/0008467 A1 | 1/2010 | Dussault et al. |
| 2010/0127169 A1 | 5/2010 | Whittum et al. |
| 2010/0166294 A1 | 7/2010 | Marrion et al. |
| 2011/0017920 A1 | 1/2011 | Goer et al. |
| 2011/0049377 A1 | 3/2011 | Morf et al. |
| 2011/0114838 A1 | 5/2011 | Han et al. |
| 2014/0091238 A1 | 4/2014 | Miyashita et al. |
| 2015/0174430 A1* | 6/2015 | Felici .......... A61N 5/1077 600/1 |
| 2016/0247656 A1 | 8/2016 | Hemberg et al. |
| 2016/0287905 A1 | 10/2016 | Liger |
| 2017/0281981 A1 | 10/2017 | Mansfield |
| 2018/0133514 A1 | 5/2018 | Mansfield |
| 2018/0161600 A1 | 6/2018 | Bowman et al. |
| 2019/0022407 A1 | 1/2019 | Abel et al. |
| 2019/0022409 A1 | 1/2019 | Vanderstraten et al. |
| 2019/0022411 A1 | 1/2019 | Parry et al. |
| 2019/0022416 A1 | 1/2019 | Smith et al. |
| 2019/0022417 A1 | 1/2019 | Heese |
| 2019/0022422 A1 | 1/2019 | Trail et al. |
| 2019/0029101 A1 | 1/2019 | Roecken et al. |
| 2019/0054318 A1 | 2/2019 | Goer et al. |
| 2019/0060667 A1 | 2/2019 | Vanderstraeten et al. |
| 2019/0209870 A1 | 7/2019 | Ueno et al. |
| 2019/0255361 A1 | 8/2019 | Mansfield |
| 2019/0272969 A1 | 9/2019 | Allen |
| 2019/0314645 A1 | 10/2019 | Ciresianu et al. |
| 2020/0054896 A1 | 2/2020 | Johnson et al. |
| 2020/0086144 A1 | 3/2020 | Goer et al. |
| 2023/0039675 A1 | 2/2023 | Turk et al. |
| 2024/0245933 A1 | 7/2024 | Johnson et al. |

FOREIGN PATENT DOCUMENTS

| | | |
|---|---|---|
| WO | 2013/134597 A1 | 9/2013 |
| WO | 2013175517 A1 | 11/2013 |
| WO | 2014/116868 A1 | 7/2014 |
| WO | 2017/151763 A1 | 9/2017 |
| WO | 2017/173443 A1 | 10/2017 |
| WO | 2018/204649 A1 | 11/2018 |
| WO | 2019/016249 A1 | 1/2019 |
| WO | 2019/016301 A1 | 1/2019 |
| WO | 2019/016305 A1 | 1/2019 |
| WO | 2019/016312 A1 | 1/2019 |
| WO | 2019/016326 A1 | 1/2019 |
| WO | 2019/018341 A1 | 1/2019 |
| WO | 2019/018376 A1 | 1/2019 |
| WO | 2019/018813 A1 | 1/2019 |
| WO | 2020/018904 A1 | 1/2020 |
| WO | 2020/035615 A1 | 2/2020 |
| WO | 2021108375 | 6/2021 |
| WO | 2022/246061 A1 | 11/2022 |

OTHER PUBLICATIONS

PCT/US2017/020191, Intraop Medical Corporation, International Search Report and Written Opinion, dated May 24, 2017, 12 pages.
PCT/US2020/061963, Intraop Medical Corporation, International Search Report and Written Opinion, Feb. 16, 2021, 10 pgs.
PCT/US22/30022, Intraop Medical Corporation, International Search Report and Written Opinion, Feb. 16, 2021, Aug. 24, 2022, 8 pgs.
NanoDot™—Dosimetry Badges I Landauer,https://www.landauer.corn/product/nanodot, (2019) pp. 1-2.
Keane, MD, et al., "Intraoperative Radiotherapy in the Era ofIntensive Neoadjuvant Chemotherapy and Chemoradiotherapy for Pancreatic Adenocarcinoma" American Journal of Clinical Oncology, vol. 00, No. 00 (2016), pp. 1-6.
Balter et al., "Anniversary Paper: A sampling of novel technologies and the role of medical physicists in radiation oncology" Med. Phys.35 (12), Dec. 2008, pp. 5641-5652.
Casali et al, "An electron beam imaging system for quality assurance in IORT" Nucl. Instr. and Meth. in Phys. Res. B 213 (2004) pp. 616-620.
Palta, Ph.D., et al., "Intraoperative Electron Beam Radiation Therapy: Technique, Dosimetry, and Dose Specification: Report Task of Force 48 of the Radiation Therapy Committee, American Associate of Physicists in Medicine" Int. J. Radiation Oncology Biol. Phys., vol. 33, No. 3, (1995) pp. 725-745.
Radiation Products Design, Inc., Periscopic Viewer, May 27, 2017,pp. 1-4.
Beddar et al., "Intraoperative radiation therapy using mobile electron linear accelerators: Report of AAPM Radiation Therapy Committee Task Group No. 72" Med. Phys. 33, (2006) pp. 1476-1489.
Nakagawa et al., "Dosimetry of leakage doses from a mobile accelerator for IORT and legal issues for its clinical use in Japan" Int J Clin Oncol (1999) 4, pp. 215-219.
Willett et al, Intraoperative Radiation Therapy: Journal of Clinical Oncology, vol. 25, No. 8, (2007) pp. 971-977.

(56) References Cited

OTHER PUBLICATIONS

R.M. Wilenzick, Department of Radiation Therapy, Alton Ochsner Medical Foundation, W.S. Kubricht, Jr., et al, Mary Bird Perkins Radiatio Treatment Center, "Evaluation of a Commercial ApplicatorSystem for Intraoperative Radiotherapy" (1985) pp. 1-20.
K.R. Hogstrom, et al., "Design of metallic electron beam cones foran intraoperative therapy linear accelerator" Int. J. Radiat. Oncol. Biol. Phys. 18, (1990) pp. 1223-1232.
J. R. Palta and N. Suntharalingam, "A nondocking intraoperativeelectron beam applicator system" Int. J. Radiat. Oncol. Biol. Phys. 17, (1989) pp. 411-417.
C. E. Nelson, et al., "The dosimetric properties of an intraoperative radiation therapy applicator system for a Mevatron-80" Med. Phys. 16, ( 1989) pp. 794-799.
Ravichandran et al., "Diamond detector in absorbed dose measurements in high-energy linear accelerator photon and electron beams", Journal of Applied Clinical Medical Physics, vol. 17, No. 2, 2016, pp. 291-303.
IntraOp, Mobetron® 2000 Product Specification (Sep. 2016) pp. 1-16.
McCullough, et al., Technical Notes "The dosimetric properties of an applicator system for intraoperative electron-beam therapy utilizinga Clinac-18 accelerator" Med. Phys. vol. 9, No. 2 (Mar. 21, /Apr. 1982) pp. 261-268.
H. Kharrati, et al., "Design of a non-docking intraoperative electron beam applicator system" Radiotherapy and Oncology 33(1) (1994) pp. 80-83.
M.J. Day, B.A., et al., "The 4 MeV Linear Accelerator At NewcastleUpon Tyne" Brit. J. Radio !. 31 (1958) pp. 669-682.
M. Weissbluth, et al., The Stanford Linear Accelerator "II. Installation and Physical Measurements" Radiology, 72 (2) (1959) pp. 242-253.
Thwaites et al., "Back to the future: the history and development of the clinical linear accelerator", Phys. Med. Biol. 51 (2006) R343-R362.
Jones, "Apparatus, Technique and Dosimetry of Intraoperative Electron Beam Therapy" Vaeth JM, Meyer JL (eds): The Role of High Energy Electrons in the Treatment of Cancer. 25th Annual San Francisco Cancer Symposium, Feb. 1990. Front Radiat Ther Oncol. Basel, Karger, vol. 25 (1991) pp. 233-245.
Varian, SIP Data Sheet, Linatron XP 950 kV Portable X-Band X-Ray Source (May 2016) pp. 1-2.
Almond et al., "The calibration and use of plane-parallel ionization chambers for dosimetry of electron beams: An extension of the 1983 AAPM protocol report of AAPM Radiation Therapy Committee Task Group No. 39" Medical Physics vol. 21, No. 8, (1994) pp. 1251-1260; doi: 10.III8/I.597359.
EP 211537748.5, Intraop Medical Corporation, Extended European Search Report, search completed Apr. 23, 2021, 5 pages.
McLaughlin, David, "Energy spectra comparisons for matched clinical electron beams on Elekta linear accelerators using a permanent magnet spectrometer" (2013). LSU Master's Theses, pp. 1-173 103; https://digitalcommons.lsu.edu/gradschool_theses/ 103.
Agostinelli et al, "On-line optimization of instraoperative electron beam radiotherapy of the breast", Radiotherapy and Oncology xxx (2012) xxx-xxx, 1-5, doi:10.1016/j.radonc.2012.01.009.
Wambersi et al., "Medical Applications of Electron Linear Accelerators" In: Turner S (ed) CERN Accelerator School (CAS): Cyclotron, linacs and their applications, CERN 96-02, (1996) CERN, Geneva, pp. 229-248.
AAPM Report No. 63, Radiochromic Film Dosimetry, "Radiochromic film dosimetry: Recommendations of AAPM Radiation Therapy Committee Task Group 55" (1998), pp. 1-25, Reprinted from Medical Physics, vol. 25, Issue II, Nov. 1998.
Price et al., "In vivo dosimetry with optically stimulated dosimeters and RTQA2 radio chromic film for Intraoperative radiotherapy of the breast" Medical Physics 40 (9), pp. 091716-1-091716-9 (2013); doi: 1O.II18/1.4819825.
Tabata, "Backscattering of Electrons from 3.2 to 14 MeV*", Postprint, re-edited for inclusion in T. Tabata, edited with commentary, The Collected Works of Tatsuo Tabata vol. 3, IDEA-TR 7 (2017), of the paper published in the Physical Review, vol. 162, Issue 2, Oct. 10, 1967, pp. 336-347 (doi:IO.II03/PhysRev.162.336).
Kenneth F. Koral and Allan J. Cohen, "Empirical Equations for Electron Backscattering Coefficients, NASA Technical Note", NASA TN D-2909, pp. 1-19 (1965); https://ntrs.nasa.gov/search.jsp?R~19650017673 2019-06-20TI2:37:48+00:00Z.
Bengt E. Bjarngard, et al., "Electron scattering and collimation system for a 12-MeV linear accelerator", Med. Phys. vol. 3, No. 3, May/Jun. 1976 pp. 153-158.
Sung-Joon Ye, et al., "Monte Carlo techniques for scattering foil design and dosimetry in total skin irradiations", Med. Phys. 32 (6), Jun. 2005, pp. 1460-1468.
Prof.P.G.Mahajan et al., "Basic Operation & Applications of Van de Graaff Generator" IJSRE vol. 05, Issue 05, May 2017, pp. 6395-6399; DOI: http://dx.doi.org/10.18535/ijsre/v5i05.04.
Karzmark, "Advances in linear accelerator design for radiotherapy" Medical Physics, vol. II, No. 2, Mar./ Apr. 1984, pp. 105-128.
Nakagawa et al., "Dosimetry of leakage doses from a mobile accelerator for IORT and legal issues for its clinical use in Japan" Int J Clin Oncol (1999) 4, pp. 215-219.
Purdy et al., "Dual Energy X-Ray Beam Accelerators in Radiation Therapy: An Overview" Nuclear Instruments and Methods in Physics Research BIO/II (1985) pp. 1090-1095.
D. Goer, Linear Accelerator, Medical , Encyclopedia of Medical Devices and Instrumentation, 1988, John Wiley & Sons, vol. 3, pp. 1772-1800.
Muluta et al., "Intraoperative Electron Radiotherapy (IOERT) as an Alternative to Standard Whole Breast Irradiation: Only for Low Risk Subgroups?" Breast Care (2014) 9, pp. 102-106; DOI: 10.II59/000362392.
Silverstein et al., "Intraoperative Radiation Therapy: A Critical Analysis of the Eliot and Targit Trials. Part 1—Eliot" Ann Surg Oncol, Jun. 23, 2014, Published online: Aug. 27, 2014, pp. 1-6; DOI 10.1245/ sl0434-014-3998-6.
Silverstein et al., "Intraoperative Radiation Therapy: A Critical Analysis of the Eliot and Targit Trials. Part 2—Targit" Ann Surg Oncol, Jun. 23, 2014, Published online: Aug. 20, 2014, pp. 1-6; DOI 10.1245/sl0434-014-3999-5.
Meurk et al., "The Mobetron: A New Concept for IORT" Vaeth JM ( ed): Intraoperative Radiation Therapy in the Treatment of Cancer, Front Radiat Ther Oncol. Basel, Karger, 1997, vol. 31 , pp. 65-70.
Khan et al., AAPM Report No. 32, Clinical electron-beam dosimetry: Report of AAPM Radiation Therapy Committee Task Group No. 25, Med. Phys., vol. 18, Issue 1, (1991) pp. 73-109.
Jean Bourbis, MD, et al., "Clinical translation of Flash radiotherapy: Why and how?" Radiotherapy and Oncology, 139, Oct. 2019, pp. 11-17.
Kutcher et al., "Comprehensive QA for radiation oncology: Report of AAPM Radiation Therapy Committee Task Group 40," Med. Phys. 21 (4) Apr. 1994, pp. 581-618.
Klein et al., "Task Group 142 Report: Quality Assurance of Medical Accelerators," Med. Phys. 36 (9) Sep. 2009, pp. 4197-4212.
Arvind Jain et al., Design and Operating Experience of Triode Electron Guns for Industrial Electron Accelerators, WEPMA011II, APAC 2007, Raja Ramana Center for Advanced Technology (RRCAT), Indore, India, pp. 348-350.
PCT/US2020/049925, International Search Report and Written Opinion, Feb. 10, 2021, 19 pgs.
D. Bhattacharjee et al., Development of Electron Guns for Linacs and DC Accelerator, J. of Physics: Conference Series 390 (2012) 012071.
EP 20862319.9, Intraop Medical Corporation, Extended European Search Report, search completed Aug. 18, 2023, 7 pgs.
EP 20894405.8, Intraop Medical Corporation, Extended Euorpean Search Report, search completed Nov. 15, 2023, 6 pages.
D. Bhattacharjee et al., Development of Electron Guns for Linacs and DC Accelerator, J. of Physics: Conference Series 390 (2012) 012071, pp. 1-6.
S. Mahadevan et al., "Improved Version of the Triode Electron Gun", Nuclear Instruments and Methods in Physics Research A, vol. 438 (1999) pp. 573-576.

(56) References Cited

OTHER PUBLICATIONS

Felici et al., "Transforming an IORT Linac Into a Flash Research Machine: Procedure and Dosimetric Characterization," Frontiers in Physics, (2002) vol. 8, Art 374, pp. 1-11.

Esplen et al., "Physics and biology of ultrahigh dose-rate (Flash) radiotherapy: A topical review," Institute of Physics and Engineering in Medicine, Physics in Medicine and Biology (2020) vol. 65, No. 23, pp. 1-107.

Rahman et al., "Electron Flash Delivery at Treatment Room Isocenter for Efficient Reversible Conversion of a Clinical Linac," Int J Radiat Oncol Biol Phys. (2021) 1;110(3):872-882. doi: 10.1016/j.ijrobp.2021.01.011. Epub Jan. 11, 2021.

David H. Whittum, "Microwave Electron Linacs for Oncology," Reviews of Accelerator Science and Technology, vol. 2 (2009) pp. 63-92.

Grosswendt, "Determination of Electron Depth-Dose Curves for Water, ICRU Tissue, and PMMA and Their Application to Radiation Protection Dosimetry," Radiation Protection Dosimetry (1994) vol. 54, No. 2, pp. 85-97.

Peter R. Almond et al., "AAPM's TG-51 protocol for clinical reference dosimetry of high-energy photon and electron beams," Med. Phys. 26 (9), Sep. 1999, pp. 1847-1870.

C.J. Karzmark et al. "Treatment Beam Production," Medical Electron Accelerators, McGraw-Hill, New York, (1993) Ch. 8, cover page, contents v-xii, pp. 137-156.

C.J. Karzmark et al. "Multi-X-Ray Energy Accelerators," Medical Electron Accelerators, McGraw-Hill, New York, (1993) Ch. 11, cover page, contents v-xii, pp. 189-199.

* cited by examiner

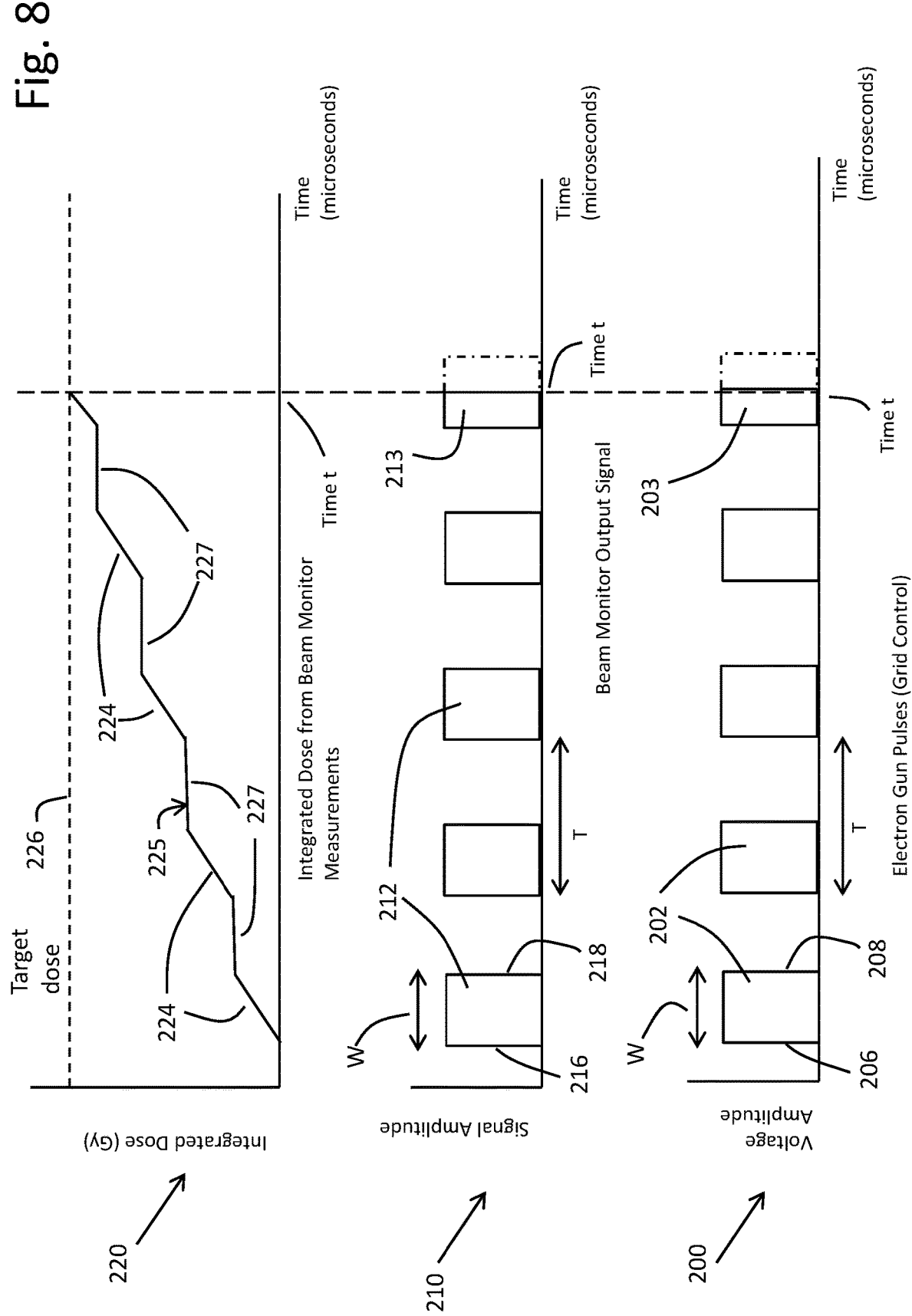

METHODS AND SYSTEMS FOR USING AND CONTROLLING HIGHER DOSE RATE IONIZING RADIATION IN SHORT TIME INTERVALS

PRIORITY

This application claims priority to International Application No. PCT/US2020/049925, filed on Sep. 9, 2020, which in turn claims the benefit of U.S. Provisional Patent Application No. 62/900,505 filed on Sep. 14, 2019, entitled "CONTROL AND OPERATION OF AN ELECTRON BEAM AT FLASH ENERGY LEVELS," and U.S. Provisional Patent Application 62/986,104 filed on Mar. 6, 2020, entitled "METHODS AND SYSTEMS FOR USING AND CONTROLLING HIGHER DOSE RATE IONIZING RADIATION IN SHORT TIME INTERVALS," the disclosures of which are hereby incorporated by reference in their respective entireties for all purposes.

FIELD OF THE INVENTION

The present invention relates to the field of methods and systems that use ionizing radiation to carry out therapeutic and industrial treatments. More particularly, the present invention relates to such methods and systems in which partial pulse strategies are used to control ionizing radiation to deliver accurate doses even when doses are delivered in short time intervals resulting in using higher dose rates.

BACKGROUND OF THE INVENTION

Ionizing radiation includes many forms of electromagnetic radiation, as well as proton beams, electron beams, and the like. Ionizing radiation is useful for both industrial applications and for radiation therapy (also "radiotherapy") in treatments of humans, animals, and plants. In an illustrative example, radiation therapy generally involves using ionizing radiation to selectively irradiate and destroy cancer tissue relative to normal tissue. Radiation therapies also are useful in a range of non-cancer therapies.

Ionizing radiation is created and delivered clinically by either of two primary methods: electronically created, externally delivered beams of energetic photons or other particles (e.g., electrons, nucleons, nuclei, etc.) or Brachytherapy comprising internal sources of radioactive nuclei placed interstitially or inserted as an intracavitary source that decays by emitting useful forms of high energy particles (e.g., electrons, protons, alpha particles) or photons (ionizing electromagnetic radiation). Many modern external beam delivery systems take the form of either linear or circular accelerating structures attached to gantries. In many instances, the systems incorporate a patient support and beam delivery and aiming apparatus for an overall treatment system that is capable of treating patients in a few minutes each day for some prescribed course of radiation therapy.

Conventional radiation therapy has evolved over the last century to produce normal tissue sparing by a combination of fractionation and target volume optimization using advances in imaging and computing technologies. This has led to increased tumor doses and cure rates and less complications. These gains have propelled radiotherapy from a treatment of last resort to one of the three pillars of oncology: surgery, chemotherapy, and radiation oncology.

In radiation therapy, the standard treatment dose SI unit definition adopted worldwide is the Gray (Gy), which is defined as one Joule of energy absorbed per kg of tissue. A typical external beam radiation treatment regimen may require a total delivered dose of between 45 Gy and 60 Gy to eradicate a cancerous tumor over the course of many treatments, referred to as fractions. Conventional external beam radiation therapy treatments generally are delivered in multiple small fractions, often 1.5 Gy to 2.5 Gy per fraction per day. In many treatment regimens, the fractions usually are delivered during the weekdays (Monday through Friday) with weekends off until the total prescribed dose has been delivered.

Conventional radiation units generally deliver radiation at a rate of 1 Gy/min to 15 Gy/min so that each daily fraction may be delivered typically in no less than 2-5 minutes ranging up to 10 minutes or more of actual beam on time. The delivery time for a fraction can be more than 10 minutes in some instances, such as for arc therapies or highly modulated Intensity Modulated Radiation Therapy (IMRT), Stereotactic Body Radiotherapy (SBRT), or Stereotactic Radiosurgery (SRS)-type treatments. The commercial systems that deliver radiation fractions at these dose-rate regimes have been designed with control technologies (referred to as dosimetry) that allow for the accurate delivery of the dose prescription to the tumor volume with usually less than 5% delivered dose error, preferably less than 3% dose error.

Some radiotherapy treatments deliver doses in higher fractions than 2.5 Gy while simultaneously reducing the total dose necessary for tumor control. For example, in Accelerated Partial Breast Irradiation (APBI), patients receive 2.7 Gy/fraction to 5.0 Gy/per fraction in 5 to 10 fractions over a 5 to 7 day period. The total dose is reduced to 25 Gy to 34 Gy from the traditional breast cancer dose of 45 Gy to 50 Gy delivered in 3 to 6 weeks. In conventional treatments it is thus possible to increase the dose per fraction while reducing both the overall treatment time and reducing the dose needed to achieve tumor control. Both the accelerated and conventional treatment deliver the same biologically equivalent dose (BED) to the tumor bed. The BED effect is predicted by the well-known $\alpha/\beta$ model of tumor destruction. Another example at conventional dose rates is the stereotactic radiation of early stage lung tumors or the irradiation of solitary brain metastases, which delivers the BED in one to 5 fractions.

Delivering the radiation over several days in multiple fractions provides a biological advantage to help spare normal tissue. Normal tissues are better oxygenated than tumor tissues and can repair damage caused by radiation faster than tumors. Normal tissues can recover and repair damage to some degree in the periods between fractions while the tumor, in most cases, is unable to heal to the same degree and continues to be eradicated to a greater degree by the subsequent irradiation fractions. In many cases, especially for early stage disease, a tumor will eventually be reduced in size so that the body's normal immune system can manage the residual tumor burden.

Despite the many significant gains in radiation therapy technology, it remains desirable to further minimize the harm to normal tissue by increasing the ability of irradiation to selectively target mainly tumorous tissue relative to normal tissue. The past 25 years of technology adoption in radiation therapy has focused on achieving gains in the therapeutic window by using sophisticated geometric based conformal avoidance technology. However, even with extremely advanced imaging and tumor tracking robotics, many tumors remain radioresistant at the doses that can be tolerated by the involved normal tissues under conventional dose rates of 1 Gy/min to 15 Gy/min. Beyond sophisticated conformal avoidance techniques, a potential treatment that could spare normal tissue while increasing the dose to radioresistant tumors and other tumors could greatly expand the therapeutic window currently experienced with conventional dose rates and techniques. Seeking more selective treatment techniques has been an important focus of radiation oncology research.

Recently, it has been discovered that radiation doses delivered within atypically short time frames (e.g., under 10 seconds, or even under 1 second, or even under 0.5 seconds, or even under 0.25 seconds, or even under 0.1 seconds) not only lead to extremely high dose rates relative to conventional radiotherapy (e.g., greater than 10 Gy/s or even greater than 20 Gy/s, or even greater than 40 Gy/s including up to 100 Gy/s, or even up to 400 Gy/s, or even up to 1000 Gy/s, or even up to 2000 Gy/s) but also show a remarkable selectivity to destroy cancer tumors relative to normal tissue with reduced harm to normal tissue. For example, in these very high dose delivery and short time of treatment modes, some treatments may deliver a total dose of 10 Gy or even 50 Gy of radiation delivered in 0.25 seconds or less, or even in 0.1 seconds or less. Delivering such doses in the shorter time intervals of these examples would yield illustrative dose rates of 40 Gy/s to 2000 Gy/s. Such newer techniques would be helpful for treatment of a wide range of cancerous tumors but would be particularly beneficial for treatment of any formerly characterized 'radiation resistant' tumor, because the discovered selectivity could allow the dose to be escalated to the point of cure with dramatically lower impact upon normal tissue.

This new approach is referred to in the field of radiation therapy as FLASH irradiation or FLASH radiotherapy. Researchers report that it is desirable to deliver the FLASH dose as fast as possible in order to better optimize the biologic FLASH effect of enhanced normal tissue sparing. In other words, research shows that the FLASH selectivity to target cancerous tissue relative to normal tissue at a given dose tends to increase as the time interval used to deliver the dose is reduced. Stated another way, the selectivity with respect to a given total dose delivered increases with increasing dose rate.

In one recent experiment reported by oncology researches at the Hospital of the University of Pennsylvania, tumors in the abdomen of mice were treated using FLASH technology. Tumors were "flashed" with a single pulse of radiation lasting 100 to 200 milliseconds. Remarkably, the researchers reported that the tumor growth was stymied while healthy tissue was unharmed.

Over 30 years ago the International Commission on Radiation Units (ICRU) created standard definitions and nomenclature for cancerous tissue volumes to be used for all radiation therapy treatments. These have been adopted worldwide as standard medicolegal definitions of physician prescriptions involving lesions and normal tissue and the boundaries inherent in prescribing curative doses of radiation. They involve three primary progressive and encompassing volumes: Gross Tumor Volume (GTV) defined as the gross apparent clinical tumor extent; Clinical Tumor Volume (CTV) defined as the GTV plus a surrounding margin for non-apparent subclinical disease extension; and, lastly, the Planning Target Volume (PTV) which is defined as the CTV plus a margin added for technical delivery errors known to exist with a given delivery technique (to include all motion and uncertainties of localization technologies, treatment planning errors, etc.).

In 2019, the radiation oncology group of the Centre hospitalier universitaire vaudois (CHUV) (also known as the Lausanne University Hospital) in Lausanne, Switzerland reported the first treatment of a human patient with FLASH radiotherapy. They prescribed FLASH dose to a PTV using a 5.6 MeV electron beam irradiating a 3.5 cm circular shaped skin lesion using a 5-mm bolus so that a total depth covered by the 90% isodose was 1.3 cm. This cylindrical tissue PTV of 3.5 cm diameter and 1.3 cm deep (30 cc of tissue) contained metastasized, chemo resistant t-cell lymphoma and some normal tissue as per ICRU definitions for a PTV. A single 15 Gy dose was delivered to the target volume in 0.090 seconds (90 milliseconds). This resulted in an average dose rate to the PTV of 170 Gy/s. The tumor response was rapid, complete and durable at 5 months from irradiation with all signs of the cancerous lesion absent. See "Treatment of a First Patient with FLASH Radiotherapy," Jean Bourbis, M D, et al., *Radiotherapy and Oncology,* 139, October 2019, pages 18-22. The oncology group has indicated that they are still following this patient. After over a year from the treatment, the oncology group indicates that the treatment site remains disease free with no remaining side effects to normal tissue (Note that the oncology group reported a transient grade 1 edema immediately after the treatment).

This first human treatment and prior animal studies suggest that FLASH radiotherapy could greatly expand the therapeutic window much beyond the current state of art using conventional dose rates and merely sophisticated conformal avoidance systems. The reason that FLASH radiotherapy works so well is still under investigation and a subject garnering a significant amount of attention in the radiation research community. In fact a diversity of radiation researchers using several forms of radiation have confirmed the effect. The selectivity observed in animals and now in a human appears to be modulated by dose rate structure and parameters that are not explained by the contemporary and reliable radiation biology models used for lower dose rate (conventional) regimes.

In the conventional models of radiation biology, DNA damage occurs due to ionization and excitation both directly in the nucleic acid and within intercellular water. The water interactions lead to the creation of reactive oxygen species (ROS) such as the peroxides, superoxide, hydroxyl radical, singlet oxygen, and alpha-oxygen. Hydrogen peroxide in turn may be partially reduced to a hydroxyl radical (*OH). These species created within the first femto-seconds and into pico-seconds after exposure comprise what is called the physical and physiochemical steps of ionizations and molecular dissociations. As time progresses to nano-seconds after exposure, the ROS begin to diffuse or move inside the cell and react. This is called the heterogeneous chemical step. After this, the ROS have largely migrated within the cell to create single and double strand breaks in nucleic acids and other cellular components, this collective damage history within each cell leads to either enzymatic DNA repair in the biochemical step or apoptosis in a matter of hours and days in the final step called the biological step.

With conventional dose rates, the irradiation time of the tissue is well into the seconds and even multiple minutes, whereas the FLASH protective effect appears in shorter exposure times, with the effect becoming more prominent as the exposure times are further reduced. Without wishing to be bound by theory, at higher doses applied in shorter time intervals, it has been hypothesized that oxygen, and therefore ROS production, is temporarily saturated and thus depleted by the nanosecond or even faster post-exposure time frames during the physiochemical step for the irradiated tissues. In FLASH irradiation, the very rapid delivery of the dose induces oxygen consumption (depletion) sufficient to create a transient hypoxia within normal (non-cancerous) tissues. The transient hypoxia is posited to protect normal tissue from damage that would ordinarily occur at lower dose rates delivered over longer time intervals.

In tumors, which are generally hypoxic by nature, the effect of FLASH radiotherapy remains lethal just as it is with conventional radiation therapy, and many researchers even report a slight enhancement to cancer killing. Thus, tumors remain subject to destruction during FLASH irradiation at a comparable rate to that experienced with conventional dose rates. Since large doses can also be delivered to the tumor in a single fraction, the effect on the hypoxic tumor is enhanced, and a single dose of 20 to 40 Gy or more, for example, can be sufficient to totally destroy the tumor with greatly reduced normal tissue toxicity.

Other possible mechanisms also are proposed and being actively investigated. These include mechanisms such as cellular signaling, immune responses and others. Regardless of the precise reason(s) that the FLASH effect occurs, the fact remains that there is a widely observed and reproducible effect now known to occur in the FLASH treatment regimes, and one of the major components of causation appears to be at least a transient hypoxia effect that protects normal tissues to a larger degree than cancerous tissues within the transient time window lasting several microseconds of beam delivery.

Ionizing radiation machines rely on dosimetry to monitor and control the delivery of ionizing radiation. Dosimetry systems directly or indirectly sample the beam itself in order to provide information such as measured machine parameters correlated to the time-dependent amount of radiation delivered as a treatment proceeds. An important function of dosimetry systems is to provide sufficient information so that a control system terminates the ionizing radiation when the correct dose has been delivered within an acceptable tolerance of time and delivered dose accuracy.

Equipment manufacturers in the field of radiation therapy have developed a diverse variety of beam monitoring systems and associated control strategies. These systems and strategies include monitoring functionality of beam uniformity or spatial homogeneity as well as beam position, direction and dose so that the prescribed dose and electron beam energy are both accurately, uniformly and repeatably delivered to the target site. In therapeutic applications, industry standards and regulations guide the degree of accuracy that is desired. Driven by regulatory requirements, the systems and strategies also incorporate at least a double contingency principle, generally resulting in multiple beam monitoring devices or technologies in a given overall system design.

FLASH technology imposes increased demands upon dosimetry systems in several aspects. First, beam monitors and other sensors must be selected and deployed in a manner that can accurately sense the radiation fluence rates leading to the higher dose rates that are associated with FLASH irradiation. Some sensors provide signals that accurately correlate to beam characteristics in non-FLASH treatments, but are not time sensitive enough for use in controlling FLASH irradiation. The beam monitors and other sensors used in FLASH treatments must be much faster than is typical due to the much shorter time frames, and in some cases extremely short time frames, needed to create the characteristically higher dose rates seen in FLASH irradiation. Further, the components that terminate an electron beam in response to sensed information also must be much faster than is typical in order to avoid dosing errors due to the same timing concerns. Thus, slow sensing technology and overall control responses found on conventional medical radiation systems could lead to unduly large errors in dose delivery inasmuch as FLASH treatments deliver significant doses in very short time frames.

Accordingly, there remains a strong demand for improved techniques to use and control ionization radiation, particularly at the timescales and dosing rates of FLASH treatments.

SUMMARY OF THE INVENTION

The present invention provides strategies to use and control the delivery of ionizing radiation to carry out therapeutic and industrial irradiation treatments. The present invention modulates the pulse width of ionizing radiation pulses in order to accurately deliver target doses of irradiation. In some embodiments, the present invention uses partial pulse control for which a full width pulse is terminated early in order to stop irradiation at the target dose. In other embodiments, the present invention dynamically modifies one or more pulse widths during a treatment in order to accurately terminate the ionizing irradiation. Pulse widths may be dynamically expanded and/or contracted in order to help accurately deliver the target dose. In some aspects, the present invention develops a pulse width recipe by which one or more pulse widths are pre-selected, and then the recipe is implemented in an irradiation treatment in order to accurately deliver a target dose. In some embodiments, dose accuracy can be further enhanced via one or more of component selection, and/or component configuration strategies in order to accurately monitor, deliver, and terminate irradiation. The strategies are particularly useful to control dosing in the short time scales and high dose rates associated with FLASH technology.

As used herein, a FLASH treatment refers to any treatment in which (a) the dose is delivered in 10 seconds or less, preferably 5 seconds or less, or under 1 second (including but not limited to times of irradiation that are in the range from $1\times10^{-7}$ seconds to 1 second, or even $1\times10^{-6}$ seconds to 1 second, or even $1\times10^{-4}$ seconds to 1 second, or even 0.1 seconds to 1 second). and (b) the dose rate is at least 1 Gy/sec, or even at least 5 Gy/s, or even at least 10 Gy/s, or even at least 20 Gy/s or higher, or even at least 40 Gy/s and higher (including but not limited to at least 1 Gy/s up to 1500 Gy/s, or even at least 10 Gy/s up to 1000 Gy/s, or even at least 20 Gy/s up to 500 Gy/s) A non-FLASH treatment refers to any treatment in which one or both of these time interval and dose rate parameters are not met.

FLASH treatments can also potentially utilize the BED concept proven in conventional treatments. That could, for example, allow certain tumors to be treated with a single FLASH dose of 20 Gy to 30 Gy in less than a second with respect to a treatment that would need a higher total dose using a conventional strategy in which the total dose is delivered in multiple fractions.

According to one aspect of the present disclosure, an ionization radiation system that deposits a target dose of pulsed ionizing radiation into a substrate during a treatment is disclosed, said ionization radiation system comprising:

a. an ionizing radiation unit that generates and deposits the pulsed ionizing radiation into the substrate during the treatment, wherein the pulsed ionizing radiation is provided as a train of one or more individual pulses, and wherein the ionization radiation comprises fluence characteristics as the treatment proceeds;

b. a control system comprising at least one sensor that monitors the pulsed, ionizing radiation as the treatment proceeds, including monitoring the pulsed, ionizing radiation during the one or more individual pulses, wherein:
  i. the at least one sensor provides an output signal indicative of the fluence characteristics of the pulsed ionizing radiation as the treatment proceeds, including providing the output signal during the one or more individual pulses;
  ii. the control system comprises program instructions that use information comprising the output signal to determine dose information indicative of the cumulative dose deposited into the substrate as the treatment proceeds, including determining the dose information during the one or more individual pulses;
  iii. the control system comprises program instructions that determine termination information indicative of comparisons between the cumulative dose and the target dose as the treatment proceeds, including determining the termination information during the one or more individual pulses; and
  iv. the control system comprises program instructions that cause termination of the pulsed ionizing radiation if the termination information indicates that the cumulative dose sufficiently matches the target dose, wherein the program instructions are configured to cause said termination during a current individual pulse if the determination indicates that the target dose is reached during the current individual pulse such that the current pulse is a partial pulse at the time of termination.

According to another aspect of the present disclosure, an electron beam irradiating system that deposits a target dose of pulsed electron beam irradiation into a substrate during a treatment is disclosed, said system comprising:
  a. an electron beam unit comprising a triode electron gun that helps to generate and deposit the pulsed electron beam radiation into the substrate during the treatment responsive to a pulsed voltage applied to the triode-based electron gun, wherein the pulsed electron beam radiation is provided as a train of one or more individual pulses, and wherein the electron beam radiation comprises fluence characteristics as the treatment proceeds;
  b. a control system comprising at least one toroid sensor that monitors the pulsed, electron beam radiation as the treatment proceeds, wherein:
    i. the at least one toroid sensor provides an output signal indicative of the fluence characteristics of the pulsed, electron beam radiation as the treatment proceeds, including providing the output signal during the one or more individual pulses;
    ii. the control system comprises program instructions that use information comprising the output signal to determine dose information indicative of the cumulative dose deposited into the substrate as the treatment proceeds, including determining the dose information during the one or more individual pulses;
    iii. the control system comprises program instructions that determine termination information indicative of comparisons between the cumulative dose and the target dose as the treatment proceeds, including determining the termination information during the one or more individual pulses; and
    iv. the control system comprises program instructions that modify the voltage applied to the triode electron gun in a manner sufficient to cause termination of the pulsed electron beam radiation if the termination information indicates that the real time total cumulative dose sufficiently matches the target dose, wherein the program instructions are configured to cause said termination during a current individual pulse if the determination indicates that the target dose is reached during the current individual pulse such that the current individual pulse is a partial pulse at the time of termination.

According to yet another aspect of the present disclosure, a method of using ionizing radiation to deposit a target dose of pulsed ionizing radiation to a substrate during a treatment is disclosed, comprising the steps of:
  a. delivering a pulsed beam of ionizing radiation into the substrate, wherein the pulsed ionizing radiation comprises a train of one or more individual pulses, and wherein the ionization radiation comprises fluence characteristics as the treatment proceeds;
  b. using at least one sensor to provide an output signal indicative of the fluence characteristics of the pulsed ionizing radiation as the treatment proceeds, including providing the output signal during the one or more individual pulses;
  c. using the output signal to determine dose information indicative of a total cumulative dose deposited into the substrate as the treatment proceeds;
  d. comparing the cumulative dose to the target dose as the treatment proceeds; and
  e. terminating the pulsed beam if the comparing indicates that the total cumulative dose sufficiently matches the target dose, wherein terminating occurs during a current individual pulse if the comparing indicates that the target dose is reached during the current individual pulse such that the current individual pulse is a partial pulse at the time of termination.

According to even yet another aspect of the present disclosure, A method of using electron beam radiation to deposit a target dose into a substrate during a treatment is disclosed, comprising the steps of:
  a. using a triode electron gun to help generate the pulsed electron beam radiation, wherein the pulsed ionizing radiation comprises a train of one or more individual pulses, and wherein the ionization radiation comprises fluence characteristics as the treatment proceeds;
  b. causing the pulsed electron beam radiation to irradiate the substrate;
  c. using at least one sensor to provide an output signal indicative of the fluence characteristics of the pulsed electron beam radiation as the treatment proceeds, including providing the output signal during the one or more individual pulses;
  d. using the output signal to determine dose information indicative of a total cumulative dose deposited into the substrate as the treatment proceeds;
  e. comparing the cumulative dose to the target dose as the treatment proceeds; and
  f. terminating the pulsed beam if the comparing indicates that the total cumulative dose sufficiently matches the target dose, wherein terminating occurs during a current individual pulse if the comparing indicates that the target dose is reached during the current individual pulse such that the current individual pulse is a partial pulse at the time of termination.

According to even still yet another aspect of the present disclosure, an ionization radiation system that irradiates a substrate with a target dose of pulsed ionizing radiation during a treatment is disclosed, said system comprising:

a. an ionizing radiation unit that generates and deposits the pulsed ionizing radiation into the substrate, wherein the pulsed ionizing radiation is provided as a train of one or more individual pulses, and wherein the ionization radiation comprises fluence characteristics as the treatment proceeds;
b. a control system comprising at least one sensor that monitors the pulsed, ionizing radiation as the treatment proceeds, including monitoring the pulsed, ionizing radiation during the one or more individual pulses, wherein:
   i. the at least one sensor provides an output signal indicative of the fluence characteristics of the pulsed ionizing radiation as the treatment proceeds, including providing the output signal during the one or more individual pulses;
   ii. the control system comprises program instructions that use information comprising the output signal to determine dose information indicative of the cumulative dose deposited into the substrate as the treatment proceeds, including determining the dose information during the one or more individual pulses;
   iii. the control system comprises program instructions that determine a pulse width modulation for at least one of the pulses using information comprising a comparison between the cumulative dose and the target dose; and
   iv. the control system comprises program instructions that dynamically cause a pulse width modulation of at least one pulse if the comparison indicates that delivering one or more additional, unmodulated pulses will deliver an excess or a shortfall in the cumulative dose relative to the target dose.

According to even yet further aspect of the present disclosure, a method of irradiating a substrate with a target dose of ionizing radiation is disclosed, comprising the steps of:
a. providing a pulse width recipe that incorporates a plurality of different pulse widths into a pulse train; and
b. using the pulse width recipe to deliver a beam of pulsed, ionizing radiation to the substrate in a manner effective to deposit the target dose into the substrate.

BRIEF DESCRIPTION OF THE DRAWINGS

FIG. 8 schematically shows how voltage pulses, electron beam pulses, and the cumulative dose are correlated.

DETAILED DESCRIPTION OF PRESENTLY PREFERRED EMBODIMENTS

Figure 1A:
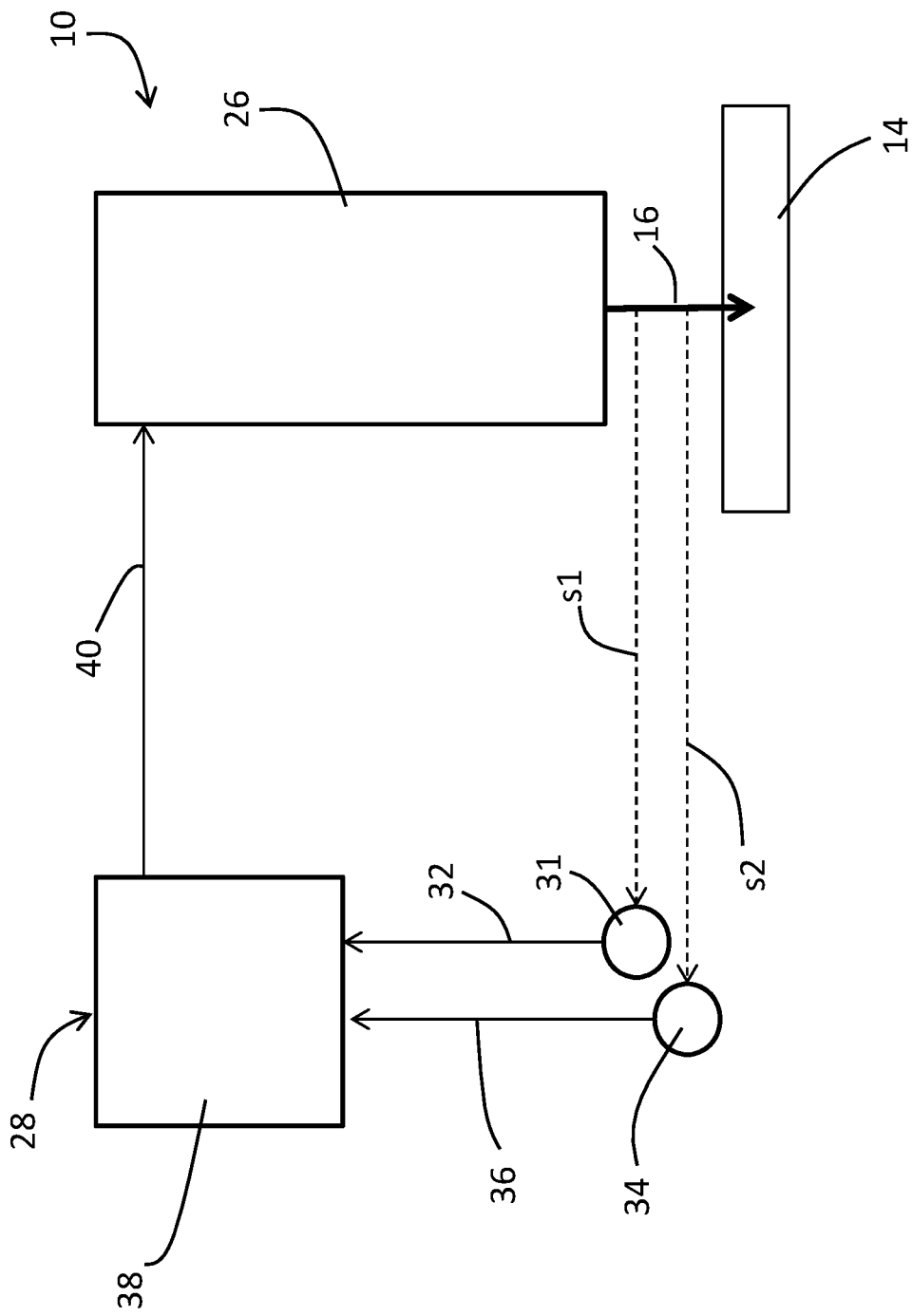
FIG. 1*a* schematically shows an illustrative embodiment of an electron beam radiation system of the present invention used to irradiate a substrate.

A detailed description of the preferred embodiments of the invention may be found below. Such embodiments are exemplary, and one skilled in the art will recognize that it is possible to practice the methods and systems of the present invention without strict adherence to the specific embodiments described herein, and no unnecessary limitations are to be understood therefrom. Numerous variations, changes, and substitutions will now occur to those skilled in the art without departing from the invention. Consequently, the illustrative embodiments of the present invention described herein are not intended to be exhaustive or to limit the invention to the precise forms disclosed in the specification and Figures. A purpose of the illustrative embodiments chosen and described is so that the appreciation and understanding by others skilled in the art of the principles and practices of the present invention can be facilitated.

All patents, patent applications, and publications cited herein are incorporated by reference in their respective entireties for all purposes.

The present invention is useful for accurately using and controlling the delivery of ionization radiation to a target site to carry out a wide range of treatments in therapeutic and industrial applications. For therapeutic applications, the present invention may be used to use and control the delivery of ionizing radiation to humans and non-humans (e.g., animals and plants) for or as an adjunct to surgery or other treatments on a wide variety of treatment sites in or on a patient in a wide variety of treatment settings. Exemplary applications in the dermatological field include prevention or treatment of scarring of the dermis including hypertrophic scarring, dermal fibroproliferative lesions, and benign fibrous tumors such as keloids. In some embodiments, electron beam radiation may be used to treat or prevent scar formation resulting from breast cancer surgical procedures or reduce the severity of scar formation in emergency room procedures. Other exemplary applications include treatment for internal conditions such as surgical adhesions and restenosis, as may occur when a blood vessel is treated for blockage. For example, principles of the present invention may be used to irradiate the microvasculature of the surgical bed to reduce the probability of formation of surgical adhesions. As another example, as an adjunct to vascular surgery, principles of the present invention may be used to treat the anastomosis of blood vessels such as the femoral artery, popliteal artery and carotid artery to help prevent restenosis.

The present invention also may be used in cancer treatment therapies. In particular, the present invention may be particularly useful to treat cancer using FLASH treatment principles inasmuch as investigators have shown that depositing ionizing radiation in short time intervals at high dose rates has remarkable ability to selectively target and destroy cancer tissue while sparing healthy tissue to a surprisingly large degree.

The present invention also may be used to use and control ionizing radiation in a wide range of industrial applications. Examples of industrial applications include gemstone irradiation (to change properties such as optical properties), food irradiation (to prevent foodborne illness, preservation, control of insects, delay of sprouting and ripening, sterilization, and the like), medical equipment sterilization (e.g., syringes, catheters, sponges, hip implants, knee implants, spinal implants, drug delivery patches, blood collection kits, drug containers, bottles, bandages, pipette tips, and the like), and cargo inspection.

The present invention is useful for accurately using and controlling the delivery of ionization radiation to a substrate or to one or more target sites in or on one or more portions of a substrate. An overall treatment may occur in one or more treatment fractions. In the case of an overall treatment using FLASH principles, an overall treatment includes preferably 1 to 5 treatment fractions, more preferably 1 to 3 treatment fractions, and even more preferably a single treatment fraction. Treatments may involve a wide variety of dosing regimens using both FLASH and non-FLASH strategies. For example, some treatments may involve dosing regimens that deposit ionization radiation at doses under 5 Gy per fraction, or even under 2 Gy per fraction as well as dosing regimens that deposit ionizing radiation at doses of 5 Gy or more per fraction. The present invention is particularly useful for accurately using and controlling the delivery of higher doses of ionization radiation per fraction, e.g., doses per fraction of at least 5 Gy, including doses per fraction of 5 Gy to 2000 Gy, or even 10 Gy to 1500 Gy, or even 20 Gy to 1000 Gy, or even 40 Gy to 400 Gy. In some current illustrative modes of practice, higher doses per fraction in the range from, for example, 5 Gy to 50 Gy per fraction when delivered in very short periods of time generally would be associated with more optimum results in FLASH treatments.

The present invention is useful for accurately controlling and depositing ionizing radiation at a wide range of dose rates. As used herein, "dose rate" refers to the average dose rate occurring during the course of a treatment fraction (which may be an entire overall treatment if the overall treatment involves only a single fraction). For example, for a fraction that delivers 40 Gy in 0.5 seconds, the average dose rate or dose rate for this treatment is 80 Gy/s. Similarly, a treatment that delivers 30 Gy in two seconds has a dose rate of 15 Gy/s. The term "instantaneous dose rate" refers to the dose deposited in a substrate over the time interval of a single pulse. For example, consider a treatment that delivers 40 Gy in 5 uniform pulses in which the dose delivery and amplitude during a pulse are uniform and constant and wherein each pulse lasts 0.20 seconds. In this scenario, each pulse delivers 8 Gy over 0.20 seconds. Within each pulse, the instantaneous dose rate is 40 Gy/s (=8 Gy/0.20 s). In some instances, the instantaneous dose rate can be quite high. For example, a pulse that delivers 100 Gy in 0.001 seconds has an instantaneous dose rate during the pulse of 100,000 Gy/s. Instantaneous dose rates on the order of $10^6$ Gy/s or $10^7$ Gy/s also may be suitable. Between pulses, where no ionizing radiation is delivered, the instantaneous dose rate would be 0 Gy/s. Some pulse trains may include pulses in which the pulse width varies and/or the dose delivered in each pulse varies. In such instances, the instantaneous dose rate would differ among such different pulses. As used herein, any reference to dose rate refers to the average dose rate unless expressly stated otherwise.

By way of example, some treatment regimens may involve depositing ionizing radiation at relatively low dose rates of under 15 Gy/min, or even under 3 Gy/min, or even under 1 Gy/min. In other modes of practice, such as with respect to treatment regimens associated with FLASH technology, ionizing radiation may be deposited at relatively higher dose rates of greater than 15 Gy/min, such as at least 1 Gy/s, or even 1 Gy/s to 2000 Gy/s, even 10 Gy/s to 1500 Gy/s, or even 20 Gy/s to 500 Gy/s, or even 40 Gy/s to 400 Gy/s.

In the practice of the present invention, ionizing radiation includes any radiation traveling as a particle and/or electromagnetic wave that carries sufficient energy to detach electrons from atoms or molecules, thus ionizing those molecules. Examples of ionizing radiation include photons such as gamma rays, x-rays, and some ultraviolet radiation; alpha particles; beta particles; neutrons; charged nuclei; muons; pions; protons; cosmic rays; and the like. An alpha particle includes two protons and two neutrons and is identical in particle content to a helium nucleus. Beta particles include high energy, high speed electrons or positrons. A flow of ionizing radiation in the form of electrons is referred to as an electron beam or ebeam.

Preferred modes of practice use ionizing radiation in the form of an electron beam. Useful electron beams may have an electron beam energy selected from a wide range. In exemplary modes of practice, a useful electron beam has an energy of at least 0.1 MeV or higher, including 4 MeV or higher, even 6 MeV or higher, even 12 MeV or higher such as up to 20 MeV, or even up to 50 MeV, or even up to 100 MeV. For FLASH treatments, electron beam energies of 4 MeV or higher, even 6 MeV or higher, even 12 MeV or higher such as up to 20 MeV, or even up to 50 MeV, or even up to 100 MeV would be suitable.

The energy of an electron beam is a factor affecting the penetration ability of the beam. Electrons with more energy tend to penetrate deeper into a substrate before stopping. Hence, due to this correlation, determining the penetration depth of an electron beam into a water phantom allows the electron beam energy to be determined. In the practice of the present invention, the electron beam energy, E, is given by $E=R_{80}/2.8$, where $R_{80}$ is the penetration depth in centimeters when the deposited dose falls to 80% of the maximum dose in a water phantom. The $R_{80}$ penetration depth is determined according to the protocol described in Peter R. Almond et. al, "AAPM's TG-51 protocol for clinical reference dosimetry of high-energy photon and electron beams," Med. Phys. 26 (9), September 1999, pp. 1847-1870 (referred to in the industry as the AAPM TG51 report). Additional AAPM reports are helpful with respect to penetration depth tolerances that are desired in therapeutic applications. These include the Kutcher et al., "Comprehensive QA for radiation oncology: Report of AAPM Radiation Therapy Committee Task Group 40," Med. Phys. 21 (4) April 1994, pages 581-618 (referred to in the industry as the AAPM TG-40 report); and Klein et al., "Task Group 142 Report: Quality Assurance of Medical Accelerators," Med. Phys. 36 (9) September 2009, pages 4197-4212 (referred to in the industry as the AAPM TG-142 report).

For purposes of illustration, the principles of the present invention will now be described with respect to using and controlling an electron beam in the exemplary embodiment of an electron beam radiation system 10 that is schematically shown in FIG. 1a. Electron beam radiation system 10 is useful to deposit a target dose of electron beam radiation into substrate 14 in one or more treatment fractions. Unit 26 is aimed so that electron beam 16 irradiates the substrate 14 in one or more electron beam pulses to deposit the desired dose using an appropriate electron beam energy, dose rate, and/or treatment time.

System 10 allows improved accuracy and control for depositing a desired dose of electron beam energy into substrate 14 by using control and hardware features that allow one or more pre-modulated (using a pre-selected recipe), dynamically modulated, and/or partial pulses of electron beam energy to be emitted at the substrate 14, optionally in combination with one or more complete pulses. For example, one treatment may involve depositing a desired dose in a single, pre-selected pulse. Another treatment may involve depositing a desired dose in one or more full pulses finishing with a partial pulse in which the final pulse is terminated early. Another treatment may involve depositing a desired dose in one or more full pulses where the full pulses cumulatively provide the total desired dose. One or more of these treatments can be practiced in one or more fractions, such as 1 or more fractions occurring over a span of hours or days or weeks. The ability to modulate the pulse width of the ionizing radiation dose delivered to a target site provides enhanced accuracy in any treatment regime, but is particularly significant for FLASH treatments.

In some treatments based on FLASH principles, depositing the total dose in a combination of a) one or more whole pulses and b) a final partial pulse could enhance the accuracy by which the target dose is deposited For example, a human patient in an early FLASH treatment regimen received 15 Gy in 90 milliseconds (in a 6 cm field size with 6 MeV electrons), which equates to an approximate instantaneous dose rate of about 150 Gy/Sec. Researchers wanting to further explore the range of possible effects for field sizes that might be useful for human clinical use may desire a range of field sizes in a range from 3 cm to 10 cm, and the dose rates desired to create the FLASH effect could increase into the several hundred Gy/sec range or even higher.

A specific example of a conventional treatment (non-FLASH) might involve delivering a total dose of 40 Gy at 10 Gy/min at a rate of 50 pulses per second (pps). This treatment involves 12,000 pulses, or only 0.003 Gy/pulse. Another conventional treatment (non-FLASH) may involve delivering a relatively low dose (e.g., 2 Gy) with a pulse frequency of 20 Hz over 2 minutes (120 seconds). In this kind of treatment, a total of 2400 pulses occur, with each pulse including 0.0008 Gy per pulse. In a conventional treatment such as these, stopping the treatment a few pulses short or carrying out the treatment for a few extra pulses has a negligible impact on the overall dose delivered. The resultant error in dose delivery is hardly impacted at all by stopping irradiation using a control system that can only stop irradiation after an integral number of pulses. Also, a delay in terminating the beam due to the time for the circuitry to effect termination also has a de minimis impact on the total dose delivered in such a non-FLASH treatment.

In contrast, a shortfall or excess of even one pulse or even a fraction of a pulse is much more significant in a FLASH treatment. Each pulse in a FLASH treatment corresponds to a significant portion of the total treatment dose. For example, an illustrative FLASH treatment might involve depositing a total of 40 Gy in 8 pulses, or 5 Gy/pulse. If 43 Gy are needed, using a whole extra pulse deposits an excess of 2 Gy, which is about a 4.6% error. Using partial pulse control strategies of the present invention allows this excess to be avoided so that 43 Gy can be more accurately deposited by finishing the treatment with a partial pulse. In short, the ability to use and control partial pulses is a key strategy to make any ionizing regimen, but particularly FLASH treatments, significantly more accurate.

In one aspect of the practice of the present invention, different strategies are available to deposit one or more modulated pulses during a treatment session. As one option, a train of pulses may be deposited. The cumulative dose is monitored as irradiation progresses. The electron beam is terminated, even in the middle of a pulse, when monitoring indicates that the target dose is reached. As another option, particularly using a solid state modulator that is able to dynamically adjust pulse width extremely fast, a train of pulses may be deposited in which the pulse width of at least one pulse is dynamically changed to be reduced or increased in order to be able to stop the electron beam when the desired target dose is reached. Such a dynamically modulated pulse width if reduced is a partial pulse in the sense that its pulse width is reduced relative to other pulses. In other instances, one pulse may be dynamically widened in order to complete a dose delivery in the event that the regular sized pulses in the treatment would fall short of delivering the target dose, and delivering two more complete pulses would deliver an undue excess of irradiation. In such an instance, the "regular" pulses are partial pulses in the sense that they have a reduced width relative to the final, widened pulse.

In other words, in an aspect, the present invention involves depositing accurate total doses using pulse strategies in which the pulse widths of the beam pulses are modulated in order to help ensure accurate depositing of the desired target dose. This can involve widening pulses, narrowing pulses, terminating pulses early, and/or the like. The pulse widths can be dynamically monitored and controlled as a treatment proceeds. Alternatively, when the instantaneous dose rate occurring during pulse(s) can be controlled with sufficient accuracy, a pulse width recipe can be provided in advance of a treatment and then carried out in order to deposit accurate total doses. For example, if a treatment goal is to deposit a target dose of 100 Gy, as might be useful in an industrial application, where the instantaneous dose rate is 1000 Gy/s, a total pulse time of 0.1 seconds is needed to deliver the total dose of 100 Gy. Example recipes may deliver the desired total dose in a single pulse lasting 0.1 seconds; two pulses lasting 0.08 and 0.02 seconds, respectively; three pulses in which two pulses last 0.04 seconds and the last pulse lasts for 0.02 seconds, etc.

As a treatment proceeds, a solid-state modulator will allow for very fast, dynamic changing of pulse widths to pulse widths less than or greater than a pre-set pulse width. In principle, this would allow for one or more pulses in a pulse train, such as a final pulse, to contain a reduced or increased dose, as the case may be, than the previous pulse(s) and so achieve more accuracy in beam termination. The practical time to change pulse widths using a solid state modulator is typically 1 to 2 microseconds, which is fast enough for effective changes to occur as a treatment proceeds with respect to the pulse repetition rates used in practice. However, changing pulse widths during a treatment may disturb the system enough so that the energy per pulse is much harder to control or predict. Changing the pulse frequency as a treatment proceeds, such as if one is using a solid-state modulator, is relatively easy to do and straightforward, but it may not provide as much accuracy in dose deposition as might be desired in some instances. This issue may be exacerbated in instances in which the dose rate per pulse is fixed based on the initial pulse width.

Consequently, in preferred embodiments, using strategies that allow one or more partial pulses to be used in combination with one or more full pulses (e.g., using uniform pulse widths in which one or more pulses are terminated early) is more preferred to modulate the energy deposited per pulse as compared to dynamically changing the pulse frequency or pulse width or as compared to specifying a pulse width recipe in advance. By using a constant pulse frequency, pulse amplitude, and pulse width with an ability to finish with one or more partial pulse(s), a more stable equipment equilibrium can be established so that the instantaneous dose rate during a pulse and the overall dose per pulse is highly uniform and highly correlated, e.g., proportional, to the pulse width. In sum, while dynamic changing of pulse widths is feasible and an aspect of the present invention, termination on partial pulses is the preferred method as it is simple to accomplish and highly accurate. Features of the invention that facilitate partial pulse strategies of the present invention are described further below with respect to system 10 and its use and control.

It is desirable that the total error in dose delivery be less than 5%, or even less than 2%. According to some current regulations, a dose error of greater than 5% is considered to be a mistreatment, but need not be reported to authorities. According to some regulations, a dose error of greater than 10% is not only a mistreatment but also must be reported to authorities.

Figure 1B:
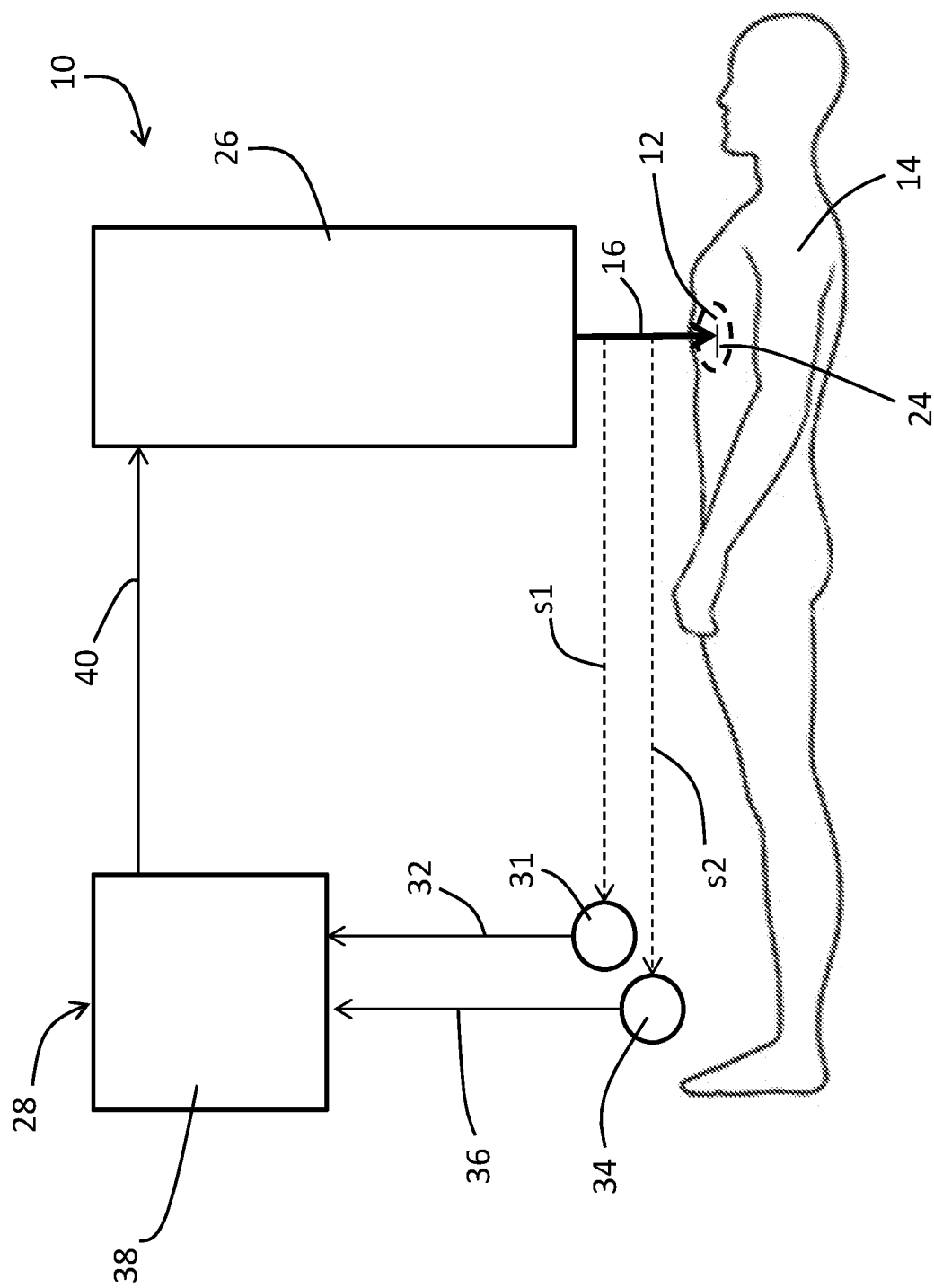
FIG. 1*b* shows the electron beam radiation system of FIG. 1*a*, wherein the substrate is a human patient.

System 10 is useful for irradiating a wide range of substrates 14. For example, FIG. 1b is a mode of practice in which substrate 14 is a human patient and in which irradiation is delivered to a target site anywhere in or on body or body parts of the patient. For example, external treatments may involve treating the ears, nose, face, forehead, scalp, back, shoulders, neck, arms, hands, chest, abdomen, pelvic region, legs, or feet. Due to the ability to control the shape and aim direction of the electron beam aimed at the target site 12, system 10 is useful for treating target sites with a variety of shapes and contours. The substrate 14 is shown as a human patient, but the treatments are useful in therapies for non-humans including plants and animals and inanimate objects such as gemstones and plastics for sterilization.

Figure 1C:
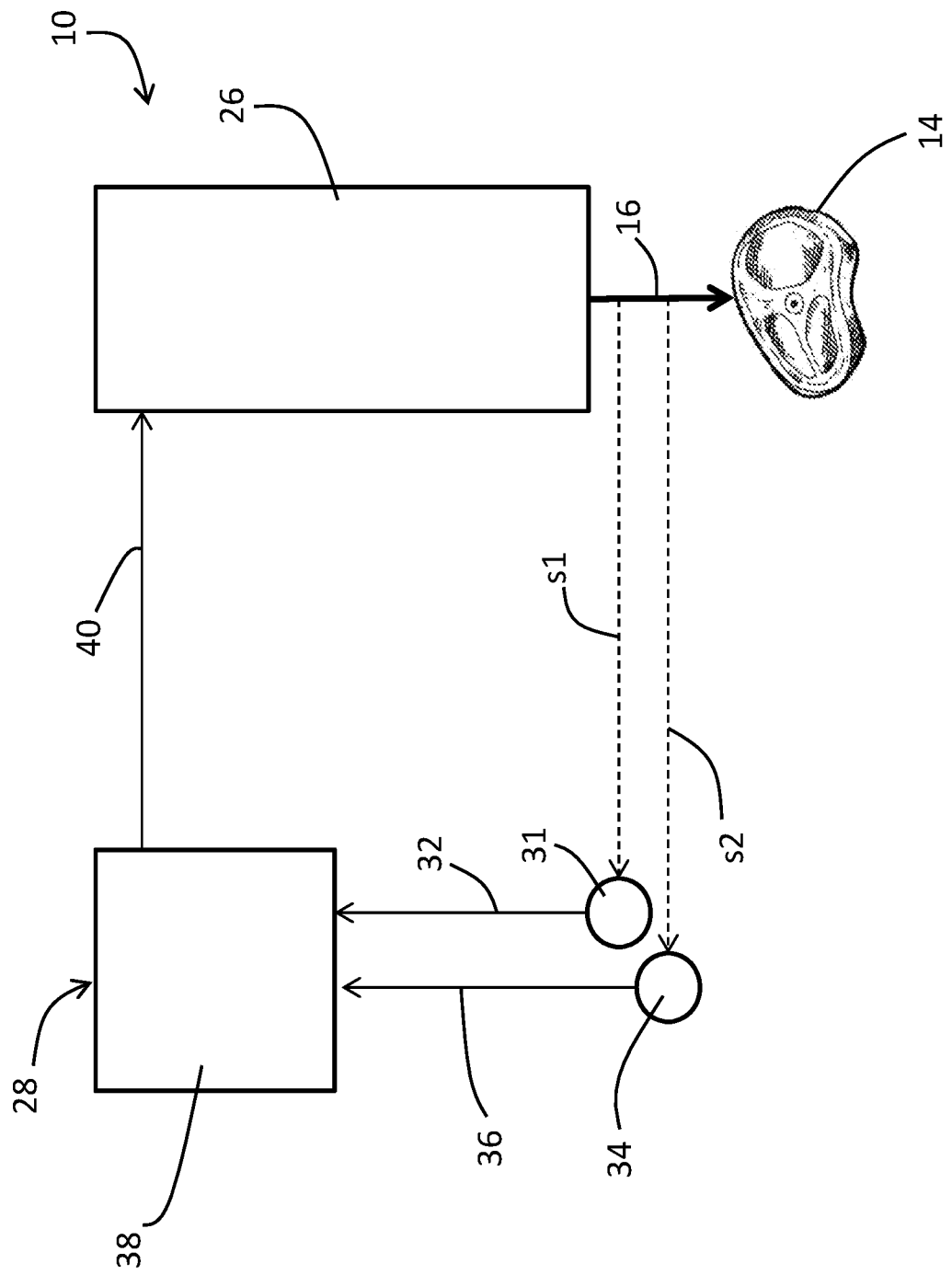
FIG. 1*c* shows the electron beam radiation system of FIG. 1*a*, wherein the substrate is meat that is irradiated for sterilization.
Figure 1D:
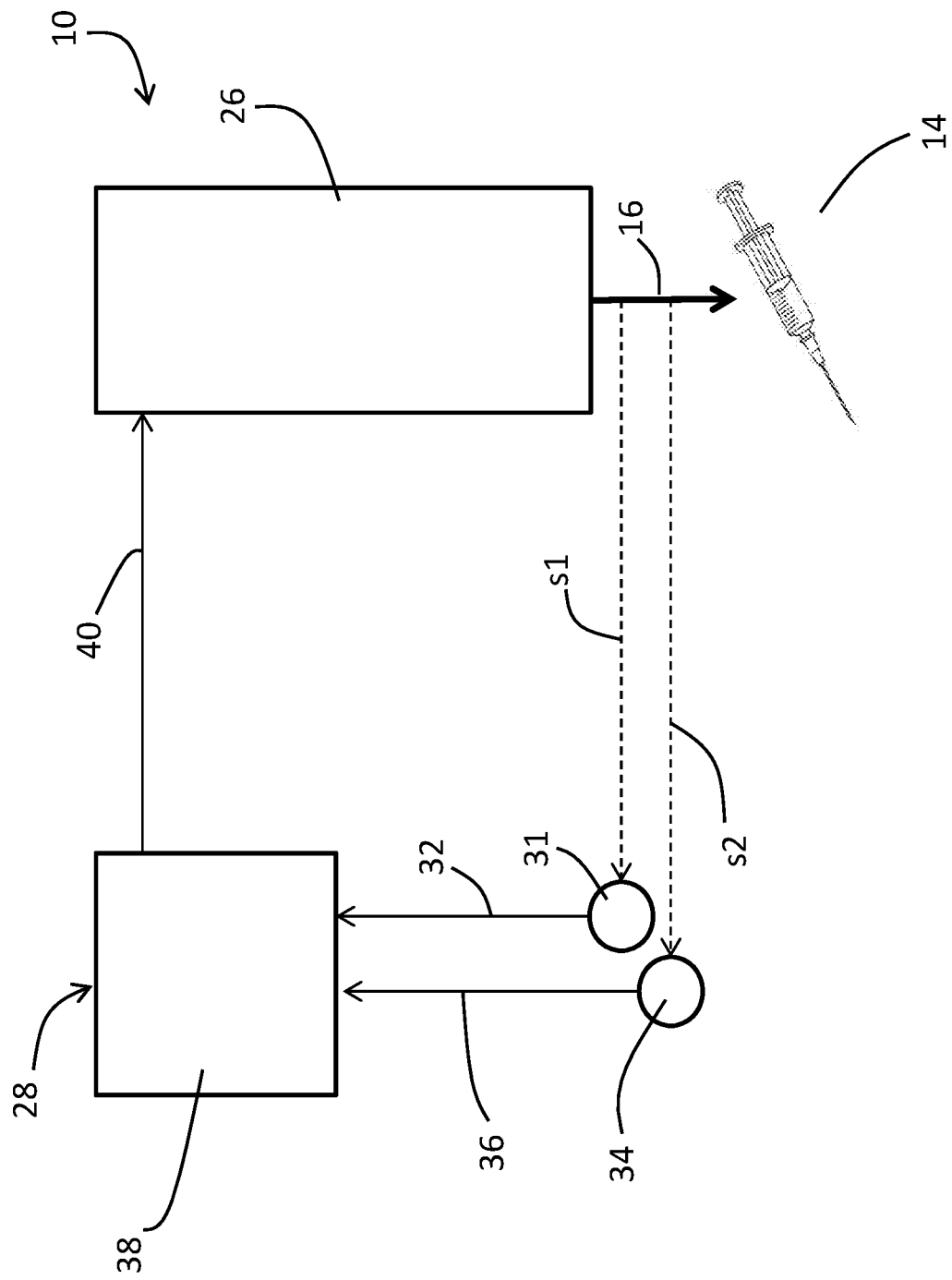
FIG. 1*d* shows the electron beam radiation system of FIG. 1*a*, wherein the substrate is a medical device in the form of a syringe being irradiated for sterilization.
Figure 1E:
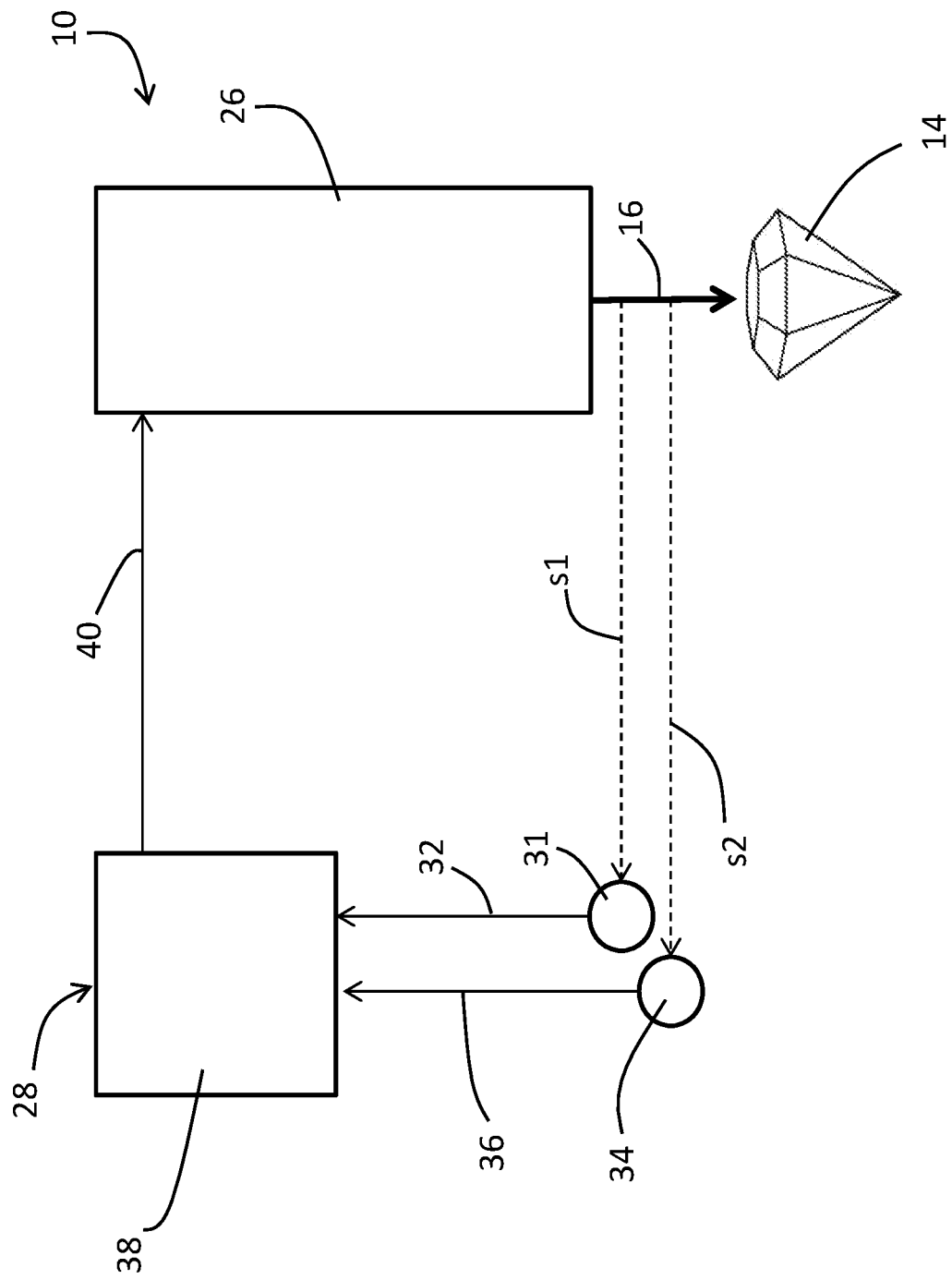
FIG. 1*e* shows the electron beam radiation system of FIG. 1*a*, wherein the substrate is a gemstone being irradiated to modify characteristics such as optical properties.
Figure 1F:
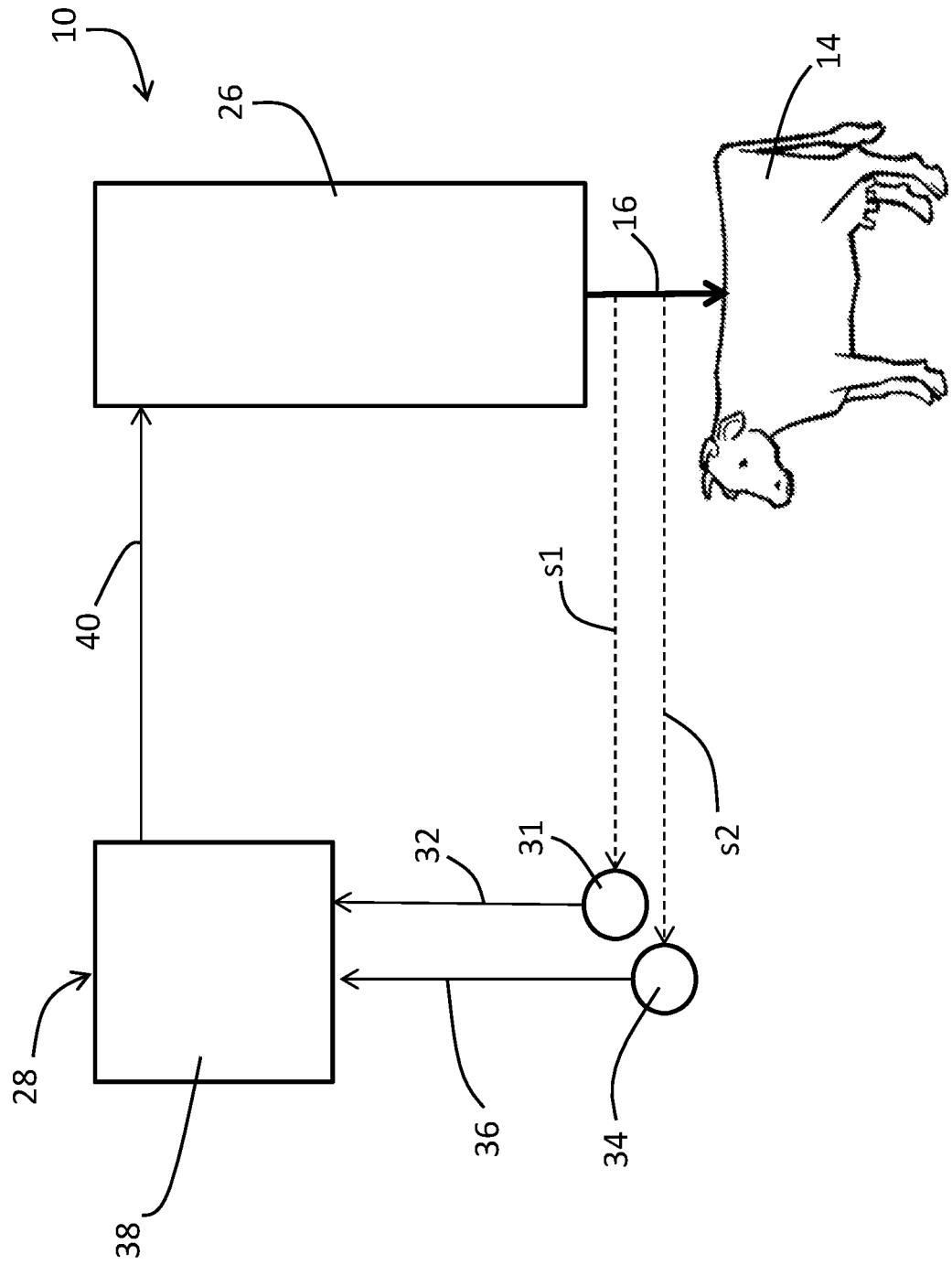
FIG. 1*f* shows the electron beam radiation system of FIG. 1*a*, wherein the substrate is an animal patient.

FIG. 1c shows system 10 being used to irradiate a substrate 14 in the form of a meat product. The meat product is irradiated for sterilization. FIG. 1d shows system 10 being used to irradiate a substrate 14 in the form of a medical syringe. The medical syringe is irradiated for sterilization. FIG. 1e shows system 10 being used to irradiate a substrate 14 in the form of a gemstone. The gemstone is irradiated to modify properties such as optical characteristics. FIG. 1f shows system 10 used to irradiate a substrate 14 in the form of an animal patient.

Reference will now be made to FIG. 1b to discuss therapeutic uses of system 10. Due to its compact nature, self-shielding capabilities, and/or mobility in many modes of practice, system 10 may be used to apply electron beam radiation before or after surgery. In some applications, such as scar amelioration, it is beneficial to irradiate the closed incision promptly. For example, system 10 can be used to deliver electron beam radiation dose(s) in a time period ranging from 0 to 24 hours, or even 0 to 5 hours, or even 0 to 1 hour, or even 0 to 30 minutes of the time of a surgery. This ability to apply irradiation treatments promptly is contrasted to treatments that use very large and immobile machines housed in separate, heavily-shielded environments that are remote from the surgical location. Radiation treatment in such large, remotely housed machines has been applied post-operatively after a delay of hours or days, thereby missing the opportunity to achieve the optimal benefits of electron beam radiation therapy.

System 10 is useful to carry out a wide range of treatments for which electron beam irradiation provides a treatment, benefit, or other desired effect for surgery or as an adjunct to surgery or other procedure. For example, system 10 may be used to treat dermatological conditions and/or to provide cosmesis. Exemplary applications in the dermatological field include prevention or treatment of scarring of the dermis including hypertrophic scarring, dermal fibroproliferative lesions, and benign fibrous tumors such as keloids. In some embodiments, electron beam radiation may be used to treat or prevent scar formation resulting from breast cancer surgical procedures or reduce the severity of scar formation in emergency room procedures. System 10 also may be used to selectively target and disable cancer tissue relative to surrounding healthy tissue.

Advantageously, system 10 is useful to carry out therapies referred to as "FLASH" treatments. The so-called FLASH treatments use atypically short time intervals and atypically high dose rates in one or more fractions, often only a single fraction. FLASH treatments have shown the ability of high energy electron beam energy delivered for brief dose intervals to selectively target and disable cancer tissue with minimal harm if any to surrounding healthy tissue. In particular, researchers have discovered that delivering higher dose rates of at least 1 Gy/s, even at least 5 Gy/s, even at least 10 Gy/s, even 20 Gy/s or higher, even 30 Gy/s or higher, even 50 Gy/s and higher, even up to 1000 Gy/s, or even up to 2000 Gy/s, vastly reduces healthy tissue toxicity while preserving anti-tumor activity.

Figure 2:
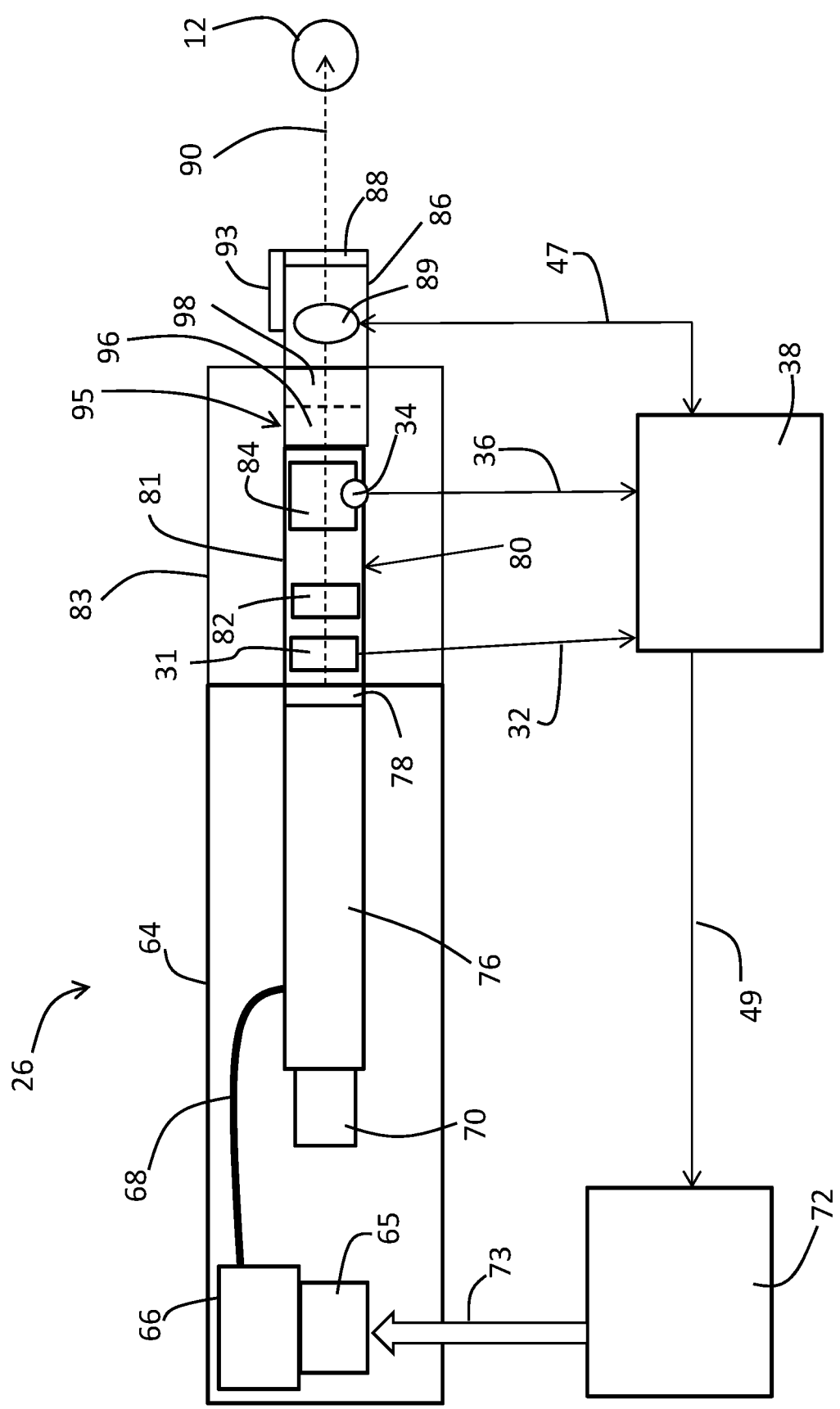
FIG. 2 schematically shows more details of an illustrative electron beam generation unit used in the electron beam radiation system of FIG. 1.

FLASH techniques used in electron beam therapy by system 10 may use electron beam energies such as an energy of 4 MeV or higher, even 6 MeV or higher, even 12 MeV or higher such as up to 20 MeV, or even up to 50 MeV, or even up to 100 MeV. FLASH techniques may deliver a total electron beam dose in a single treatment or single fraction such as a dose of at least at least 5 Gy, including doses per fraction of 5 Gy to 2000 Gy, or even 10 Gy to 1500 Gy, or even 20 Gy to 1000 Gy. FLASH techniques may deliver an electron beam dose in a relatively brief interval such as a treatment in the range from 0.01 milliseconds to 3 seconds, or even 0.01 milliseconds to 1 second or even 0.1 milliseconds to 500 milliseconds. It can be appreciated that system 10 of FIGS. 1a-1f and its components as illustrated in FIG. 2, is capable of producing electron beams with energies of 6 to 12 MeV or even higher at very high dose rates, e.g., on the order of 40-400 Gy/sec in illustrative embodiments. The high dose rate makes electron beams practical to use in gemstone irradiation. This allows the irradiation processing of gemstones to be completed in a short period of time.

Electron use could avoid the use of heavy shielding required for gamma or cobalt irradiators. Because the energy used is relatively low as compared to other types of ionizing radiation, the risk of activating the gemstones is substantially reduced.

As an alternative to using system 10 to practice FLASH radiotherapy, other modes of practice may use lesser energy, dose rates, and or doses to be delivered in one or more fractions for suitable time periods. For example, for some therapies, the electron beam energy delivered to the target site 12 is within a range from 0.1 MeV to 12 MeV, preferably 0.2 MeV to 6 MeV, more preferably 0.3 MeV to 4 MeV, and even more preferably 0.5 MeV to 2 MeV. In some modes of practice for such therapies, an operation range from 1 MeV to 2 MeV would be desirable. In such embodiments, the electron beam systems provide irradiation doses of up to about 20 Gy, such as up to about 15 Gy, up to about 10 Gy, up to about 5 Gy, or up to about 2 Gy in a treatment regime involving one or more fractions. In such embodiments, the electron beam systems may provide radiation to the target site 12 at a rate of at least about 0.2 Gy/min, at least about 1 Gy/min at least about 2 Gy/min, at least about 5 Gy/min, or at least about 10 Gy/min. In such embodiments, the electron beam energy may be delivered to the target site 12 during each fraction for a time period in the range from 0.01 milliseconds to 5 minutes, or even 0.1 seconds to 3 minutes. An exemplary mode of practice in this area uses system 10 to irradiate incised tissue proximal to a surgical incision 24 after wound closure in order to help reduce or prevent undue formation of scar tissue that otherwise could result as the incision subsequently heals.

Electron beam radiation system 10 of FIGS. 1a-1f generally includes an electron beam generation unit 26 that emits a linearly accelerated, straight through electron beam 16. Using feedback control techniques as described in U.S. Pat. No. 10,485,993, system 10 emits electron beam 16 with high stability and precision to achieve one or more desired penetration depth settings within a broad operating range. The feedback principles described in U.S. Pat. No. 10,485,993 allow the beam penetration depth, beam energy, dose, and/or dose rate to be rapidly adjusted and controlled in continuous or very small increments within the corresponding operating ranges. Being able to adjust and these characteristics continuously or in small increments provides tremendous flexibility to tailor dose, energy, dose rate, and/or penetration depth to particular patient needs. This is a significant advantage over conventional machines that have only a limited number of energy settings and/or provide beams with less stability that are subject to coarser setting adjustments.

Penetration depth of an electron beam treatment means the $R_{80}$ penetration depth as determined in water according to the protocol described in Peter R. Almond et al., "AAPM's TG-51 protocol for clinical reference dosimetry of high-energy photon and electron beams", Med. Phys. 26 (9), September 1999, pp. 1847-1870 (referred to in the industry as the AAPM TG51 report). Note that while the protocol focuses on electron beams with mean incident energies in the range from 5 MeV to 50 MeV, the same protocol is applicable for lower or higher energies that optionally may be used in the practice of the present invention. Additionally, the report provides a protocol to determine the R50 penetration depth. This is the depth in water at which the absorbed dose falls to 50% of the maximum dose. The same depth-dose data resulting from this protocol also provides the $R_{80}$ penetration depth, which is the penetration of an electron beam dose into a water phantom at which the dose drops to 80% of the maximum dose. The depth of dose maximum is referred to as Dmax. Beam and dosimetry calibration for evaluation of machine settings with respect to determining $R_{80}$ penetration depth in the practice of the present invention are defined in water using a 5 cm diameter, circular, 30 cm long zero degree tip angle applicator at a 50 cm source to skin distance (SSD). The output for a specific energy is measured at Dmax.

For example, if this test shows that a particular machine configuration yields an $R_{80}$ penetration depth of 2 cm, that configuration is deemed to provide that $R_{80}$ penetration depth at the target site 12. The machine may be calibrated or otherwise evaluated to determine a plurality of machine configurations to correspond to a corresponding plurality of penetration depths. At the time of a procedure, the care provider selects a particular penetration depth suitable for the procedure. The machine is set to the corresponding configuration. The procedure is then performed using principles of the present invention to deliver a stable and precise electron beam as the procedure is carried out.

Electron beam energy and penetration depth are strongly correlated. See B. Grosswendt, "Determination of Electron Depth-Dose Curves for Water, ICRU Tissue, and PMMA and Their Application to Radiation Protection Dosimetry," Radiat. Prot. Dosimetry (1994) 54 (2): 85-97. Depending on the embodiment, this relationship can be linear or nonlinear. Generally, higher penetration depth results from using electron beams with higher energy.

Still referring to FIGS. 1a-1f, system 10 includes feedback control system 28 configured to permit controlling and adjusting the penetration depth, electron beam energy, electron beam dose, treatment time, and/or electron beam dose rate provided by electron beam 16 with precision and stability using feedback strategies such as those described in U.S. Pat. No. 10,485,993.

As a further example, as described further below, feedback control system 28 is integrated into system 10 in a manner that allows measurement of electron beam characteristics, e.g., fluence, that highly correlate to the electron beam dose deposited into target site 12 to be monitored so that the electron beam 16 can be terminated when the total desired dose is delivered. Advantageously, feedback control system 28 and other components of system 10 incorporate features that allow the electron beam to be terminated in the middle of a pulse. As compared to conventional systems that are only able to control whole pulses, this approach more accurately delivers the target dose with substantially less risk that the dose will be too high (too many pulses delivered) or too low (too few pulses delivered).

As shown in FIGS. 1a-1f, control system 28 includes at least one monitoring sensor that is used to detect one or more characteristics of the electron beam that correlate to the deposited dose at a specified depth. Additionally, a calibration protocol for correlating sensed characteristic(s) to the deposited dose is provided by AAPM TG-51 using a water phantom. This protocol allows for different sensors to be calibrated to the deposited dose so that the protocol can accommodate calibration in both non-FLASH and FLASH treatment regimes. The calibration protocol has been described in P. R. Almond, P. J. Biggs, B. M. Coursey, W. F. Hanson, M. S. Huq, R. Nath; and in D. W. O. Rogers, "AAPM's TG-51 protocol for clinical reference dosimetry of high-energy photon and electron beams," Med. Phys. 26, 1847-1870, 1999. Once the output signal(s) of one or more sensors is calibrated and correlated to the deposited dose, the output signal is useful to monitor the ionizing radiation to determine the cumulative dose deposited in the substrate as the treatment proceeds. This allows the ionizing radiation to be terminated based on such feedback monitoring when the control system 28 determines that the cumulative dose deposited in the substrate reaches the target dose.

Monitoring in this embodiment includes at least two sensors in the form of first sensor 31 and a separate second sensor 34. In other embodiments, more sensors may be included. Alternatively, multiple sensor capabilities may be incorporated into a single sensor component. First sensor 31 measures a first characteristic (s1) of the electron beam 16. First sensor 31 sends a corresponding first sensor signal 32 to controller 38. Signal 32 corresponds to the value of the characteristic(s) s1 measured by first sensor 31. Second sensor 34 measures the second characteristic(s) s2 of the electron beam 16. Second sensor 34 sends a corresponding second sensor signal 36 to controller 38.

In illustrative embodiments described further below, the sensor 31 is in the form of a toroid sensor. In other illustrative embodiments described below, sensor 34 is in the form of an array of two or more ion current chambers deployed in the outer periphery of the electron beam channel Toroid sensors are advantageous in the context of many treatments, but are particularly advantageous in FLASH treatment regimes, as toroid sensors sense information fast enough to provide excellent control over electron beam 16 in the time scales involved with either FLASH treatments or lower dose rate treatments. Also, toroid sensors can be easily configured to handle the higher fluence levels associated with FLASH treatments as well as the lower fluence levels used in non-FLASH treatments. In some embodiments, multiple toroid sensors may be used to sense different fluence levels to allow even more accurate sensing over a wide range of fluences.

Suitable toroid sensors are commercially available, such as a toroid sensor manufactured by Pearson Electronics and available under the Model designation 110. In another alternative embodiment, TibaRay, Inc. of Sunnyvale, CA has developed a real time beam monitor that can be used to accurately correlate the dose deposited at FLASH dose rates. As will be appreciated by those skilled in the art, other alternative beam monitors may be used in the control system 28 of the present invention without departing from the spirit and scope of the present invention.

Often, an electron beam generally is homogenized over about 70% to 80% of the inner cross-sectional area of the beam that is radially closest to the beam center line. Outside this inner zone, in the outer peripheral zone of the beam cross-section, the fluence (also referred to as the flux) of the beam drops off more rapidly with increasing radial distance from the beam centerline. The beam energy also drops off but to a lesser extent. Notwithstanding the more rapid reduction in fluence in the peripheral zone with increasing radial distance from the beam center, the fluence in the peripheral zone still highly correlates to the homogenized, inner zone. This correlation is particularly accurate when the beam profile across the cross section is substantially constant at a particular centerline location of the beam. This means that both the fluence characteristics of the inner zone and the outer peripheral zone of an electron beam correlate accurately to deposited dose. The stability of the peripheral zone, its lower fluence, and its high correlation to the homogenized zone and the deposited dose allow ion chambers to be deployed in the peripheral zone with many advantages.

For example, a peripheral deployment of an array of ion current chambers in the peripheral zone is advantageous as this allows ion current chambers to be used as electron beam sensing devices in both FLASH and non-FLASH treatment regimes. Conventional deployment of an ion current chamber in non-FLASH regimes tends to place the device closer on the central axis of the electron beam 16 and after the scattering foils used to flatten the beam. While the beam energy and dose rate tend to be higher in the central region of the beam, the scattering foils used in conventional systems provides a homogenous beam energy and dose rate to an ion chamber system. Thus, the central portion of the ion chamber is exposed to relatively uniform energies and dose rates well below the saturation capabilities of many ion chambers.

On the other hand, the higher dose rates of the electron beams used in a FLASH treatment can tend to saturate the capabilities of some ion chambers if placed along the beam center line, rendering the chambers useless to sense beam characteristics, even if flattened by a scattering foil system. However, the dose rate and fluence tend to decrease with increasing radial distance from the center of the beam 16. Hence, an ion current chamber deployed around the periphery of the channel through which the beam 16 travels is exposed to lesser electron beam fluence that may be below the saturation threshold of the ion current chamber.

In short, the peripheral deployment of the ion current chambers allows the sensing devices to be used more effectively to monitor lower as well as higher dose rate electron beams with much less risk of saturation when used with respect to the higher dose rate electron beams. As an additional advantage, an array of such devices around the periphery allows the beam uniformity to be evaluated inasmuch as undue differences among sensed measurements may indicate a beam problem sufficient to trigger follow up action such as beam adjustment, termination, or the like. Many ion chambers are suitable for monitoring dose rates up to about 15 Gy/min or even 20 Gy/min. In some modes of practice, it would be desirable to deploy one or more ion chambers in the peripheral zone at locations on a particular cross section in which the dose rate is under 20 Gy/min, or even under 15 Gy/min. In some modes of practice, the flux at a particular deployment site at a cross section location is in the range of 0.01% to 70%, even 0.01% to 50%, or even 0.01% to 30% of the flux at the beam centerline of that cross section.

Generally, a beam monitor signal using a beam monitor such as a toroid sensor is dependent on the amount of beam current passing through the center of the toroid, not the energy or dose rate of the beam particles. As known to those skilled in the art, beam fluence refers to the number of particles crossing the plane normal to the beam, per unit time, per unit area. In contrast, the amplitude of an ion chamber signal tends vary with both high fluences as seen in FLASH fluences and to a lesser degree with beam energy due to the dependence of beam scattering on beam energy. With the characteristics of the two sensors in mind, the energy of the beam particles may be controlled by system 28 by taking the ratio of the beam monitor signal to the ratio of the ion chamber signals and then feeding this signal to control the microwave or RF power level. The ratio also may be used by the control electronics to provide an interlock of beam energy. An interlock refers to termination of the electron beam if the beam energy is outside of a predefined energy window.

The readings from sensor 31 and optionally sensor 34, as well as one or more optional additional sensors, if any, may be used by control system 28 in a variety of control strategies. For example, one or both of sensed characteristics s1 and s2 may be used by controller 38 to determine characteristics of the electron beam 16 as a treatment proceeds so that the total dose of electron beam energy delivered to the target site 12 can be monitored to allow the electron beam to be quickly terminated, either after a full pulse or a partial pulse as the case may be, when the target dose is reached or optionally, as the target dose is about to be reached taking into account any lag time of the system to terminate the beam in response to sensed characteristics s1 and/or s2. For example, if system calibration indicates that 0.50 Gy of energy is delivered in the time to sense and terminate the beam 16, control system 28 may be configured to send a beam termination signal when the cumulative dose delivered to target site 12 is 0.50 Gy less than the desired target dose.

As another example, according to control strategies described in U.S. Pat. No. 10,485,993, controller 38 may use the sensed information to derive an analog characteristic, A, of electron beam energy from the detected characteristics s1 and s2 presented by the signals 32 and 36. The result is that measuring at least two different characteristics of the beam and using those to derive the analog characteristic allows characteristics of the electron beam 16, such as energy, dose, dose rate, treatment duration, penetration depth, and/or the like, to be easily controlled by control system 28 with high precision.

Additionally, controller 38 can use the control signal 40 in different ways to implement other feedback control. As one example, control signal 40 can be used to shut off the electron beam pursuant to an interlock protocol. As another example, control signal 40 can be used to adjust power source(s) that generate the electron beam in order to tune electron beam energy as desired. In some embodiments, such power-based control can be implemented by feedback control of the microwave source 66 (See FIG. 2 or 3) and/or the electron source 70 (See FIG. 2 or 3). Using the feedback control strategies, modulator or magnetron-based feedback (e.g., feedback to regulate modulator output voltage or magnetron frequency) allows adjusting electron beam energy in steps or continuously over the desired operating range, e.g., 0.1 MeV to 12 MeV in some embodiments, or even 6 MeV up to 20 MeV, or even up to 50 MeV, or even up to 100 MeV in other illustrative embodiments.

Figure 3:
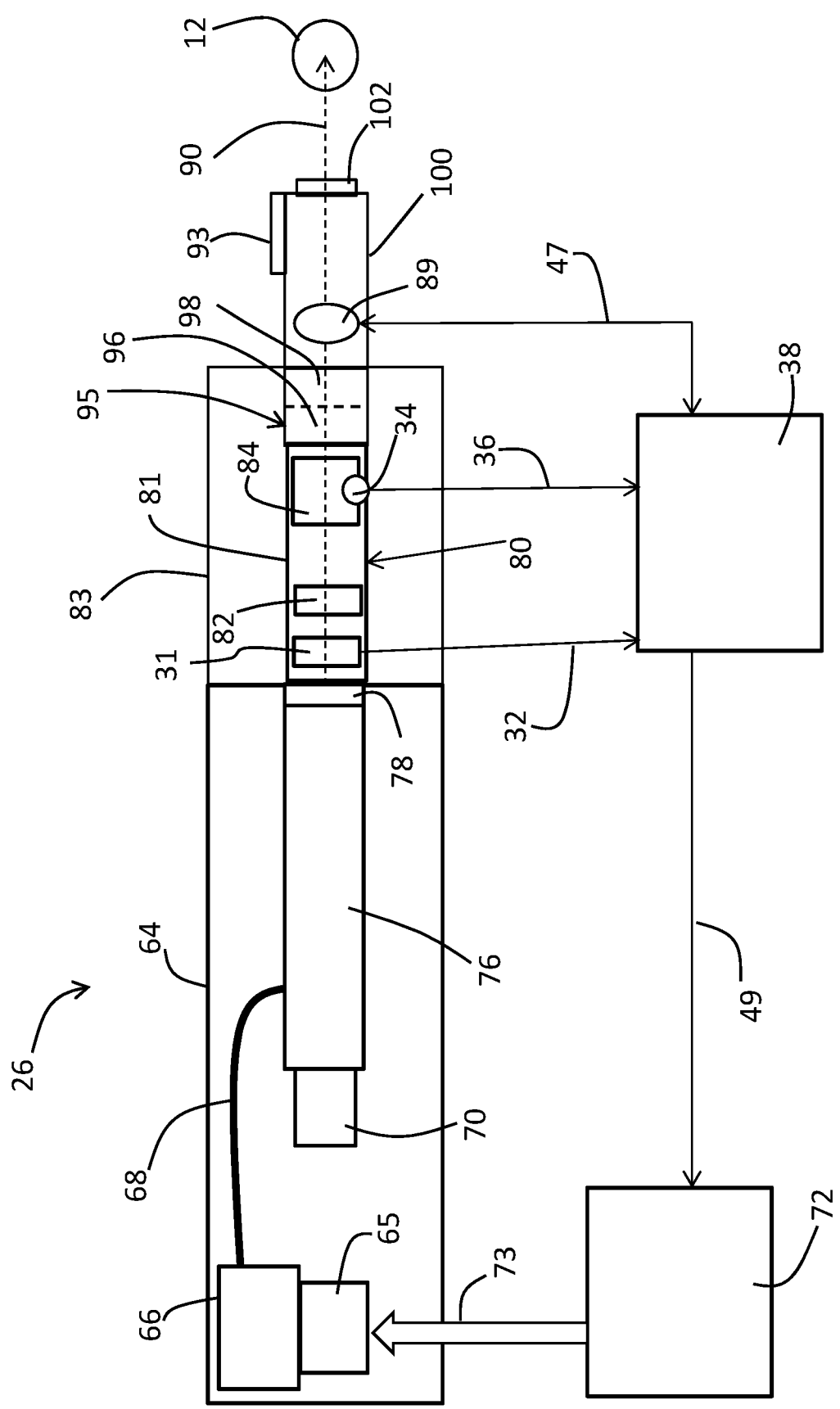
FIG. 3 schematically shows an alternative embodiment of an electron beam generation unit useful in the electron beam radiation system of FIG. 1.

As another example, the modulator output voltage can be regulated to affect current supplied to the magnetron and the microwave power. The magnetron power may be regulated, which impacts the amount of power delivered to the accelerator 76 (FIGS. 2 and 3). In addition to these strategies or as an alternative to these strategies, feedback control strategies may be used with respect to other system features that are used to establish the electron beam, including gun voltage or the like. The gun voltage can be regulated to impact the launch velocity of electrons, phasing, capture, and energy spectrum.

Additionally, the electron source 70 (See FIG. 2) and the RF-source 65 (see FIG. 2) often are typically pulsed at the same rate (i.e., the same pulse repetition frequency) but the pulse widths are not necessarily the same. Control system 28 may control the pulse frequencies of these components and the degree to which the frequencies are synchronized or offset. Controller 38 may be configured to be able to turn on or turn off each of the electron source 70 and the RF-source 65 independently such as to turn on the system 10 and allow it to warm up, to operate the electron beam during a treatment, or to quickly terminate the electron beam even in the middle of a pulse.

In many cases associated with beam actuation and termination, it is easier and faster to turn the electron gun on and off than the magnetron. This means that preferred modes of practice involve turning the electron gun off to terminate the electron beam more quickly upon reaching the target dose. As another consequence of electron gun actuation being faster, in many modes of operation, the magnetron pulse width is usually fixed, while the pulse width of the electron gun may be adjusted to a different width depending on the required dose per pulse. A narrower gun pulse produces less dose per unit time, and a wider pulse produces more dose per unit time up to a point at which the gun pulse is as wide as the magnetron pulse. The magnitude of the electron gun and/or magnetron pulses can also be changed to control the output, but this is a slower process. Consequently, magnitudes of the magnetron and electron gun pulses usually remain constant for an entire treatment Maintaining uniform pulse magnitudes is particularly important for a FLASH treatment in which the total treatment time is very short so that magnitude changes might not reach stability or even the new level in the timeframe of the treatment.

As another control strategy, control system 28 may use sensed information to provide current to steering coils upstream, so as to steer the beam 16 and/or continuously correct any beam offset or symmetry error in real time. As another control function of control system 28, the sensor readings may be used to terminate the beam 16 and limit the amount of radiation deposited into the target site if an issue with the electron beam is detected. For example, a loss of a scattering foil could result in delivery of an excessive dose. In this fashion, control system 28 provides one or more protective interlocks to shut down the beam under such circumstances.

As another approach to implement feedback control, control signal 40 can be used to adjust the settings of one or more physical system components, e.g., one or more electron beam absorbers, whose selected position setting can be used to modulate the electron beam energy. One such adjustable component is an electron beam absorber of variable thickness that can be adjusted to present different thicknesses, and hence different absorptions, to the electron beam. Such absorber-based control may be accomplished with single absorbing plates providing a range of selectable thicknesses, a variable thickness ribbon, or a rotating body containing whose degree of rotation presents variable thickness absorption to the electron beam. Using the feedback control strategies of the present invention, absorber-based feedback allows adjusting electron beam energy in steps or continuously over the desired operating range.

When using any absorber(s) to help tune the electron beam, control system 28 desirably includes monitors that confirm that an absorber is in the correct installed position. If the monitors provide a signal indicating that the position is incorrect, an interlock protocol is triggered that prevents the electron beam from being turned on. Similarly, in those embodiments in which system 10 includes a plurality of absorbers with different thicknesses, a particular absorber or combination of absorbers is the proper absorber selection for carrying out a particular treatment at a desired penetration depth. Accordingly, control system 28 desirably contains monitors that check if the installed absorber matches the machine settings for the particular treatment. If the improper absorber is installed for the selected procedure, an interlock protocol is triggered that prevents the beam from turning on. As a further safety function, a particular treatment will usually involve delivery of a particular radiation dose. Control system 28 desirably monitors the delivered dose in real-time and initiates an interlock protocol to turn off the electron beam to avoid overdose.

Some embodiments of the present invention combine both power-based and absorption-based feedback control of the electron beam energy, dose, dose rate, and/or hence penetration depth.

Exemplary features of one embodiment of a suitable electron beam generation unit 26 useful in system 10 are shown schematically in FIG. 2. Unit 26 according to FIG. 2 incorporates features that help to provide partial pulse control in accordance with the present invention.

As seen in FIG. 2, electron beam generation unit 26 generally includes a first housing 64 that contains a modulator 65, microwave source 66, a microwave network 68, an electron source 70, and a linear accelerator 76. A second housing 83 contains a collimator assembly 80. Rotary coupling system 95 helps to rotatably mount one or more field-defining members to be incorporated into unit 26. By way of example, unit 26 of system 10 (as illustrated in FIGS. 1a-1f) includes a first field defining member in the form of an applicator 86 and a second field-defining member in the form of shield 88 integrated into the unit 26. Coupling system 95 generally incorporates a first sub-assembly 96 and a second sub-assembly 98, wherein the first sub-unit 96 and second sub-assembly 98 are rotatably coupled to each other. The rotational coupling allows relative rotation between the two sub-assemblies 96 and 98 about an axis of rotation that is parallel to, and desirably co-linear and coincident with, the central axis of the linear electron beam path 90. The coupling system 95 also incorporates automated distance detection, automated illumination functionality, and other functionality. Details of rotary coupling system 95 and its functionality are further described in U.S. Ser. No. 62/941,327, filed Nov. 27, 2019, titled "ELECTRON BEAM RADIATION SYSTEM WITH ADVANCED APPLICATOR COUPLING SYSTEM HAVING INTEGRATED DISTANCE DETECTION AND TARGET ILLUMINATION," in the names of Turk et al.,.

An external power supply 72 supplies power to the modulator 65 via power cable 73. Power supply 72 and power cable 73 as an option may be included inside housing 64 along with other components. An exit window 78 is provided at the interface between linear accelerator 76 and collimator assembly 80, Scattering foil system 82 and ion chamber 84 is housed in collimator assembly 80 along with first sensor 31 and second sensor 34. Unit 26 generates an electron beam, which is aimed along substantially linear electron beam path 90 from accelerator 76 straight through applicator 86 to the target site 12 (also shown in FIGS. 1a-1f. An optional field-defining shield 88 is placed at the exit of the applicator 86.

A wide range of sensor devices may be used as sensor 31 and/or sensor 34. Generally, such sensors have functionality that allows sensing beam characteristics for a wide range of electron beam flux rates and energy levels such as those associated with both FLASH and non-FLASH treatments. One example of such sensing devices includes gas-filled detectors in which radiation causes ionization of a gas to generate a detectable amount of charge carriers that is correlated to the dose or dose rate of the ionization radiation passing through the detector. The detection signal often is a level of electric current that correlates to the flux or flux rate. Alternatively, these devices may develop a signal by counting pulses. Ionization chambers, proportional counters, and Geiger-Muller counters are examples of gas detectors of this type. In preferred embodiments, second sensor 34 is in the form of an array of ion chambers deployed around the periphery of the collimator assembly 80 defining a channel through which the electron beam 16 flows. The peripheral deployment allows sensing of higher dose and dose rate beams to be measured with much less risk that the ion chambers would be saturated by the full flux of the beam 16 at its center. The array deployment allows the uniformity of the beam 16 to be monitored.

Scintillation detectors are another type of detector that may be used to detect characteristics of ionizing radiation. These detectors include a material that exhibits luminescence when excited with ionizing radiation. The intensity of the luminescence generates a current in a photocathode that correlates to dose or dose rate. The luminescence on its own generally may generate currents of low intensity. Consequently, amplifiers such as photomultiplier tubes may be used to enhance the signal.

Semiconductor detectors also may be used to detect ionizing radiation. These detectors include inorganic and/or organic semiconductor material(s) that generate a level of electric current that correlates to the energy deposited in the material by the incident ionizing radiation. Semiconductor detectors are known to be more suitable for detection of ionizing radiation in the form of beta particles (e.g., electron beams) or gamma radiation as they may be susceptible to damage from heavier particles.

Thermoluminescent dosimeters also may be used as sensing devices. These devices generally include material, often crystalline material, that emits light when exposed to incident ionizing radiation. The emitted light correlates to the absorbed dose.

Chemical detectors also may be used. In these, incident ionizing radiation causes a measurable chemical change in a medium via mechanisms such as oxidation, reduction, dissociation, and the like. The level of the changes correlates to the amount of absorbed energy. One example of such a detector is the Fricke dosimeter.

Calorimetric sensors also may be used. These measure a radiation dose by measuring the temperature increase of a medium.

Induction or toroid sensors also may be used. Many embodiments include two toroidal coils, which can be examples or components of induction or toroid sensors, herein. Each toroidal coil can be viewed schematically as being annularly deployed around a central bore. Consequently, material such as ionizing radiation can flow through the central bore without obstruction from the coils. One toroidal coil emits an electric field. This induces an electric field in the second coil. The passage of ionizing radiation through the center bore increases the current in the second coil in an amount that correlates to the flux of the ionizing radiation. In practical effect, a toroid sensor, toroidal coil, or toroidal current monitor (commonly referred to as a toroid), is a donut shaped current to voltage transformer wherein the current to be measured typically flows through the central bore of the toroid. The output signal correlates to the instantaneous dose rate. This can be calibrated and integrated to accurately provide information such as the real time cumulative dose and the like.

In preferred embodiments, first sensor 31 includes at least one toroid sensor. Toroid sensors are very practical devices for measuring gun and beam currents because they are commercially available in various sizes and shapes and can be specified to have rise and decay profiles in the low nanosecond range, which helps to ensure that the pulse shape and amplitude is accurately sensed. A toroid sensor is fast and accurate enough to detect electron beam characteristics to provide meaningful control even at higher electron beam dose and dose rates occurring in short term intervals. The beam can be projected through the central bore area of the toroid with minimal beam obstruction. A toroid sensor rarely is fouled and requires low maintenance. Toroid sensors also are robust to electron beam 16, even at FLASH treatment levels. In more preferred embodiments, first sensor 31 includes at least one toroid sensor and the second sensor 34 includes one or more ion chambers.

Electron beam generation unit 26 as shown in FIG. 2 is the type that uses linear acceleration techniques to boost electron beam energy to desired levels. The use of linear accelerator structures to generate electron beams for therapeutic uses is well known. Additionally, electron beam generation unit 26 is a "straight through" type of system. As known in the art, a straight through system aims an electron beam at a target site along a generally linear path from the exit window 78 of the linear accelerator 76 straight through to the target site 12. This helps to ensure use of much of the beam current produced. Bending systems, in contrast, waste greater proportions of the beam current through absorption in bending magnet slits. Wastage of beam current in bending systems generally produces substantially greater background radiation per unit of dose delivered. A linear, straight-through beam line minimizes such beam loss and better optimizes dose per unit current to the target site. This means that the linear systems need less shielding. Straight through systems, therefore, tend to be smaller, more lightweight, and more compact than alternative systems that use heavy magnets and heavy shielding to aim electron beams on bent paths to a target site. An additional advantage of a straight through system is that energy may be varied quickly as there is no eddy current diffusion time limit or hysteresis as with bent beam systems.

One example of such a system suitable for intraoperative procedures is described in U.S. Pat. No. 8,269,197 assigned to IntraOp Medical Corporation. Another example of such a system suitable for intraoperative procedures is the electron beam machine commercially available from IntraOp Medical Corporation under the trade designation MOBETRON. Generally, linear, straight through systems such as these are a result of engineering a compact linear accelerator that can fit when vertical under ceiling heights common to many procedure sites such as treatment rooms or surgery rooms. These compact systems avoid complex bending systems that tend to generate extraneous background radiation that necessitates massive shielding. Advantageously, principles of the present invention may be incorporated into the MOBETRON electron beam machines, which would provide a mobile FLASH treatment system including intraoperative FLASH treatments. Strategies to configure and operate the MOBETRON electron beam machines and other linear electron beam machines in FLASH treatment modes are described further below.

Still referring to FIG. 2, modulator 65 receives power from the power output of power supply 72 via cable 73. Power supply 72 may be any suitable source of electricity. Power supply 72, as an option, may be a component of a continuous source of electricity from a power utility. Alternatively, power supply 72 may be battery powered, permitting untethered operation of electron beam generation unit 26. Modulator 65 accepts the power from power supply 72 (which may be line power, battery power or any suitable power source), and converts it to short pulses of high voltage that it applies to the microwave source 66. Microwave source 66 converts the voltage into microwave or RF energy. The pulses generated by the modulator have a frequency, pulse width, magnitude and duty cycle that can be controlled by control system 28 (see FIGS. 1a-1f).

Examples of suitable microwave sources for use as microwave source 66 include a magnetron or a klystron to power linear accelerator 76. A magnetron is more preferred as being less expensive and simpler to incorporate into system 10.

Many suitable embodiments of a magnetron operate using X-band, S-band, or C-band frequencies. X-band devices are more preferred, as other embodiments of unit 26 tend to be heavier when using S or C band devices. X-band frequency technology also tends to minimize the diameter, and hence the weight, of the accelerator structure. One illustrative example of a suitable magnetron operating at X-band frequencies is the Model L-6170-03 sold by L3 Electron Devices. This magnetron is capable of operating at a peak power of about 2.0 megawatts and 200 watts of average power.

Microwave network 68 conveys the microwave or RF power from the microwave source 66 to the linear accelerator 76. The microwave network 68 often typically includes a waveguide (not shown), circulator (not shown), a load (not shown), and an automatic frequency control system (not shown). The use of these components in an accelerator system is well known to those skilled in the art and has been described in the patent literature. See, e.g., U.S. Pat. No. 3,820,035. Briefly, microwaves from the RF source passes through the circulator before entering the accelerator guide to protect the RF source from reflected power from the accelerator 76. Instead, the power not absorbed in the accelerator 76 is reflected back into the circulator and shunted into a water-cooled or air-cooled dummy load. In the preferred embodiment, air-cooling is preferred as air cooling reduces weight and minimizes servicing issues. An AFC circuit is used to keep the resonant circuit tuned to the microwave frequency. Air cooling works in the practice of the present invention because magnetron average power, e.g., 200 W in an illustrative embodiment, is relatively low for electron beams. In contrast, x-ray machines typically involve average power in the range from 1 kW to 3 kW. The ability to use air cooling with electron beams is one factor that helps preferred electron beam machines of the present invention to be so compact and lightweight.

Microwave or RF power may be injected into the accelerator structure through a fixed waveguide if the microwave source 66 (e.g. a magnetron) is mounted on a rigid assembly (not shown) with the linear accelerator 76. Alternatively, a flexible waveguide may be used in the microwave network 68. As one option for implementing the feedback principles of the present invention, microwave or RF power supplied to the linear accelerator 76 through microwave network 68 may be modulated in the case of a magnetron by varying the pulsed high voltage supplied to the magnetron from power supply 72. Modulating the voltage of the power supply 72 in this manner correspondingly allows the energy level, dose, dose rate, and/or penetration depth of the electron beam 16 to be controlled and adjusted to many different desired settings with excellent precision using the feedback strategies of the present invention. For a klystron, the same approach may be used. Alternatively, the input microwave power to the klystron may be varied.

In parallel with microwave source 66 supplying microwave or RF energy to linear accelerator 76, electron source 70 supplies electrons to linear accelerator 76. Electron source 70 typically includes an electron gun and features that couple the gun to the linear accelerator 76. Many different embodiments of electron guns are known and would be suitable. For example, some embodiments use a diode-type or triode-type electron gun, with a high-voltage applied between cathode and anode. Many commercially available electron guns operate at voltage ranges between 10 kV to 17 kV, though electron guns operating at other voltages may, in some embodiments, also be used. The voltage often is either DC or pulsed. In the case of the triode-type gun, a lower grid voltage also is applied between the cathode and grid. The grid can disable or enable the beam 16, and the grid voltage may be varied continuously to inject more or less gun current. The grid voltage applied to the electron gun has a frequency, pulse width, magnitude and duty cycle that can be controlled by control system 28 (see FIGS. 1a-1f). A skilled worker in the field of linear accelerator engineering is able to understand and choose an appropriate gun design suitable for the linear accelerator 76 to be used.

Triode electron guns are preferred for use in the partial pulse control strategies of the present invention. Although diode guns are simpler in construction, diode guns tend to be slow to turn on and off due to the large voltage swing often required (such as in the range from 5 kV to 20 kV). Triode guns are more complex, but the extra grid element allows the gun current to be controlled with a much smaller voltage swing (e.g., around 200 volts or even less). As a result, the gun current can be turned off completely, and the electron beam terminated as a consequence, in under 100 nanoseconds. Upon delivery of the desired dose, this timeframe is fast enough to terminate the electron beam in a wide range of electron beam treatments, including FLASH treatments that occur at high doses and high dose rates in timeframes that may span only a fraction of a second.

Exemplary embodiments and descriptions of triode electron guns are described in U.S. Pat. Nos. 3,651,360; 9,257,253; and in U.S. Pat. App. Pub. No. 2019/0272969. See also Arvind Jain et al., Design and Operating Experience of Triode Electron Guns for Industrial Electron Accelerators, WEPMA011, APAC 2007, Raja Ramana Center for Advanced Technology (RRCAT), Indore, India, pp. 348-350; D. Bhattacharjee et al., Development of Electron Guns for Linacs and DC Accelerator, J. of Physics: Conference Series 390 (2012 012071; S. Mahadevan et al., Improved Version of the Triode Electron Gun, Nuclear Instruments and Methods in Physics Research Section A: Accelerators, Spectrometers, Detectors, and Associated Equipment, Vol. 438, Issues 2-3, 11 Dec. 1999, pages 573-576.

One example of a commercially available electron gun suitable in the practice of the present invention has been sold by L3 Electron Devices (formerly Litton) under the product designation M592 Electron Gun. The injector cathode of this particular gun operates in some embodiments at 10 kV to 14 kV and has a very small diameter, emitting surface. This design is intended to provide low emittance and good capture efficiency while maintaining low energy spread. Typical pulse widths for operation may be in the range from 0.5 to 6 microseconds.

The microwave or RF source is pulsed by modulator 65. It is preferred that the modulator 65 be solid state based rather than tube based to reduce weight and improve portability. A solid state based modulator also allows a rapid reprograming of key parameters that is particularly helpful for rapid modulation suitable for the high dose rates and rapid treatment times associated with FLASH operation, such as pulse width. The pulse repetition frequency (PRF) may be selected from a wide range such as from about 1 to about 500 pulses per second, and the pulse width may be selected from a wide range such as from about 1 to 25 microseconds. Some treatments can occur at these frequency rates and pulse widths for a particular time duration, e.g., from about $10^{-6}$ seconds, or from about $10^{-5}$ seconds, or from about $10^{-4}$ seconds up to about 0.1 seconds, or even up to 0.5 seconds, or even up to 3 seconds, or even more seconds in some treatments. Other treatments may proceed for a given number of pulses and optionally fractional pulses such as from 1 to 50 pulses. The combination of PRF and pulse width is one factor that impacts the dose rate of the emerging electron beam. For triode or diode gun systems, the gun likewise may be pulsed by the same modulator system, albeit with an intervening gun transformer to permit a step in voltage. Alternatively, the gun may be pulsed by a different modulator. In the practice of the present invention, it is the pulse width, pulse magnitude, pulse frequency, and pulse duty cycle applied to the electron gun that are associated with the pulse width, pulse magnitude, pulse frequency, and pulse duty cycle, respectively, of the electron beam 16 (See FIGS. 1a-1f). Hence, adjusting these characteristics of the electron gun tends to adjust beam characteristics even if similar characteristics are fixed with respect to the voltage applied to the microwave or RF source.

Linear accelerator 76 is configured to receive the microwave or RF power from the microwave network 68. Linear accelerator 76 also is configured to receive the electrons from the electron source 70. Linear accelerator 76 is coupled to the microwave network 68 and the electron source 70 in a manner effective to use the microwave or RF power to accelerate the electrons to provide electron beam 16 having an energy level in the desired operating range.

A variety of different linear accelerator structures would be suitable in the practice of the present invention. For example, linear accelerator 76 may have a structure that implements any of a variety of different cavity coupling strategies. Examples of suitable structures include those that provide side cavity coupling, slot coupling, and center hole coupling. C. J. Karzmark, Craig S. Nunan and Eiji Tanabe, Medical Electron Accelerators (McGraw-Hill, New York, 1993). Linear accelerator 76 also may have a structure that implements a variety of different symmetry strategies. Examples of suitable structures include those that provide periodic, bi-periodic, or tri-periodic symmetry. Examples of suitable accelerator structures also may implement a range of standing wave or travelling wave strategies. Examples of suitable linear accelerators 76 also may be selected to operate with many different bands of microwave or RF power. Examples of suitable power bands include S-Band (2-4 GHz), C-Band (4-8 GHz), X-Band (8-12 GHz), and still higher frequencies. David H. Whittum, "Microwave Electron Linacs for Oncology," Reviews of Accelerator Science and Technology, Vol. 2 (2009) 63-92. In some illustrative embodiments, the linear accelerator 76 uses a low profile structure design, incorporating on-axis bi-periodic cavities operated at X-band frequencies. U.S. Pat. No. 8,111,025 provides more details on charged particle accelerators, radiation sources, systems, and methods, side-coupled X-band accelerators and on-axis and side-coupled S-band and C-band accelerators are other suitable examples.

The linear accelerator 76, its attached electron source 70, and one or more other components of electron beam generation unit 26 may be mounted inside housing 64 on a strongback (not shown) or other suitable support member. The linear accelerator 76 and electron source 70 may be encased in lead or other shielding material (not shown) as desired to minimize radiation leakage. The higher the resonant frequency of the accelerator guide, the smaller is the diameter of the structure. This results in a lighter-weight encasement to limit leakage radiation. An advantage of linear, straight through machines is that the shielding requirements are less severe than machines that using beam bending strategies. This allows straight-through electron beam radiation machines to be more easily deployed for intraoperative procedures in a conventional operating theater rather than being deployed in remote locations inside heavily shielded rooms or requiring heavy shielding to be added to an operating room theater which increases the costs and structural issues to permit operation.

During operation, the network, the linear accelerator and the microwave source 66 experience heating. It is desirable to cool unit 26 (particularly the units 65, 66, the circulator and loads in microwave network 68, and accelerator structure 76) in order to dissipate this heat. A variety of strategies can be used to accomplish cooling. For example, accelerator structure 76 and microwave source 66 can be water-cooled as is well known. In addition, the practice of the present invention permits operation at low-duty cycle, for which air-cooling would be quite adequate. The ability to practice air cooling simplifies the construction of unit 26 and helps to make the unit 26 smaller and more compact. The result is that the corresponding system 10 (See FIGS. 1a-1f) is easier to deploy and use in intraoperative procedures.

An exit window 78 at the beam outlet of linear accelerator 76 is provided to help maintain a vacuum within the accelerator. The window 78 is preferably strong enough to withstand the pressure difference between the accelerator vacuum and the ambient atmospheric pressure, e.g., a difference of about 15 psi in some instances, but the window 78 preferably is thin enough to avoid excessive beam interception and/or bremsstrahlung production. Balancing these factors, the window 78 may be formed of titanium in many embodiments. Alternatively, beryllium or other metallic or composite materials also may be used.

The accelerated electron beam 16 exits the linear accelerator 26 through exit window 78 and next continues on a linear path through collimator assembly 80 that receives, broadens, and flattens the beam. To implement feedback strategies of the present invention, one or more sensors such as sensors 31 and 34 may be deployed in or around collimator assembly 80 in order to detect two or more independent characteristics of the beam 16 or to detect redundant characteristics of the beam 16 for safety purposes.

Collimator assembly 80 can include a housing 81. Housing 81 may be constructed of materials that help contain bremsstrahlung radiation, or the collimator design itself could be sufficient to contain the bremsstrahlung radiation. Inside housing 81, scattering foil system 82 and ion chamber 84 are provided. Note that ion chamber 84 and sensor 34 are shown as two different components, but the ion chamber 84 may serve as at least a portion of sensor 34. Also, ion chamber 84 is schematically shown in FIG. 2. In actual practice, peripheral deployment of the ion chamber(s) 84 in the peripheral region of the electron beam may be desirable in some modes of practice. Further, the sensor 31, which desirably is a toroid sensor (as described herein) in many instances, is shown as being upstream from the scattering foil system 82. In some embodiments, the sensor 31 can be downstream from the scattering foil system 82, particularly very close downstream from the scattering foil system 82 in some embodiments.

Scattering foil system 82 serves multiple functions. For example, electron beam systems typically produce beams of small transverse dimension, on the order of 1 mm to 3 mm across, much smaller than typical treatment fields. Scattering foil system 82 helps to broaden the electron beam 16. The scattering foil system 82 also helps to flatten electron beam 16. In many modes of practice, the beam passes through the scattering foil system 82 to help in shaping of the isodose curves at the treatment plane at target site 12.

In illustrative modes of practice, scattering foil system 82 helps to enlarge the accelerated beam 16 from being several square millimeters in cross section to several square centimeters in cross section. Uniformity of dose across the treatment field is a desired goal to simplify dose planning for therapeutic applications. For example, collimator assembly 80 with or without applicator 86 may function to provide a flat electron beam dose profile such that the coefficient of variation of the beam dose across the full width at half-maximum (FWHM) of the beam is less than ±50%, less than ±40%, less than ±30%, less than ±20%, less than ±10%, less than ±5%, less than ±2.5%, or less than ±1%. Those of skill in the art will recognize that the coefficient of variation of the electron beam energy across the FWHM may have any value within this range, for example, about ±5%. In some embodiments, the collimator may function to broaden the electron beam to field sizes that are 1 cm to 25 cm across.

A typical scattering foil system 82 includes at least one, even two or more, and even three or more scattering foils (not shown). The distance between the two or more foils can vary, depending on the energy range of the unit, the field size needed for the treatment application, and the geometry and materials of the mass elements in the treatment head. Generally, electron scattering foils may be designed using techniques such as empirical design iteration or Monte Carlo simulations. Other means of providing uniformity could rely on magnetic phenomena. For example, steering coils could be employed to raster the beam across a programmed area. Alternatively, a quadrupole magnet system could be used to modify the beam size at the target plane. The first sub-assembly 96 of coupling system 95 is attached to the exit end of collimator assembly 80. In the meantime, applicator 86 is attached to the exit end of the second sub-assembly 98. Field defining shield 88 (also referred to as an "insert") is attached to the exit end of the applicator 86. Because second sub-assembly 98 is rotatably coupled to the first sub-assembly 96, this means that applicator 86 and the attached shield 88 are able to rotate about axis 192 (See FIGS. 5-7) relative to the first sub-assembly 96 and, hence, collimator assembly 80 and other upstream components of unit 26. Rotation is helpful to help ensure that an appropriate alignment for the field defining opening (e.g., the outlet of the shield 88) with the treatment site, e.g., tumor, scar, incision, etc., is achieved.

If the applicator 86 is metallic and could come into contact with the target site, the applicator 86 desirably is electrically isolated from the upstream components (e.g., coupling system 95, collimator assembly 80, etc.) of system 10. This can be accomplished in various ways such as by interposing an insulative coupling between applicator 86 and second sub-assembly 98, between applicator 86 and substrate 14 (e.g., a patient), or by forming applicator from a material that is inherently insulating (e.g., polymethyl(meth) acrylate often referred to as PMMA, quartz, ceramic, or the like).

The accelerated and collimated electron beam 16 is aimed at a target site 12 through applicator 86 and field defining shield 88. The applicator 86 and shield 88 are configured so that the electron beam continues on linear electron beam path 90 straight through to the target site 12. In many modes of practice, the applicator 86 and shield 88 further help to define the shape and flatness of the electron beam 16. Applicator 86 also makes it easier to aim the electron beam while minimizing the manipulation of, contact with, or disturbance of the patient or target site. Furthermore, the use of applicator 86 and shield 88 helps to avoid stray radiation and minimizes the dose delivered to healthy tissue by confining the radiation field.

Applicator 86 and/or shield 88 optionally may include one or more other components to help further modify the electron beam characteristics. For example, energy reduction with low bremsstrahlung can be achieved by interspersing thin (0.5-1 mm) sheets of plastic or sheets made from low atomic number material into the applicator 86 and/or shield 88 in a slot provided to accept them. Materials with higher electron density also may be used and could be thinner for the same absorption. The applicator 86 and/or shield 88 could also incorporate element(s) to act as a secondary scattering component. These may be made from suitable shaped low atomic number materials that help to further scatter electrons within the volume of applicator 86 and/or shield 88. Examples of such materials, but by no means exclusive to these materials, include aluminum, carbon, and copper and combinations of these. These can be located in applicator 86 at positions determined by Monte Carlo calculations or empirically for the energy and field size needed for the application.

In some modes of practice, a transparent or partially transparent applicator 86 and/or shield 88 may be beneficial. For example, such an applicator design may allow easier viewing of the treatment site. Applicators and or shields fabricated at least in part from PMMA, quartz, or the like would permit such viewing.

Unit 26 may be positioned in any orientation or position with respect to the target site regardless of patient orientation. In many modes of practice, the distance from the exit end of the applicator 86 (or the end of field defining shield 88, if present) to the surface of the target site can vary from contact with the target site to distances up to about 10 cm from the patient surface. The distance can be determined by any suitable measurement technique such as by either mechanical measurement or an electronic rangefinder. Advantageously, coupling system 95 includes functionality that allows distance to be determined automatically. In some embodiments, the system and/or applicator may be positioned manually to achieve any orientation or position relative to the target. In some embodiments, system and/or the applicator may be positioned using one or more motor drives for automated control of orientation and position. For example, the applicator 86 could be placed by hand and held in place by a suitable support structure (not shown). Then the electron beam machine would be docked (i.e., aligned) to the applicator 86. The applicator 86 desirably is electrically isolated from other components of system 10, particularly in treatments in which the applicator contacts or is close to the substrate 14 (e.g., a patient).

The applicator 86 may have a variety of shapes, such as being shaped to produce circular, square, irregular, or rectangular fields on the target site. Some useful applicators include cylindrical pathways for the electron beam to traverse. Another example of an applicator design, called a scan horn, creates long narrow fields by having scattering elements within the applicator that scatter electrons preferentially along the length of the field. In some embodiments, the scan horn may be used to confine the irradiated area to a strip of from about 2 cm to about 10 cm in length, and about 0.2 cm to about 1 cm in width.

FIG. 2 shows how an absorber 89 may be mounted on applicator 86 in a manner effective to tune the electron beam to adjust electron beam energy, dose, dose rate, penetration depth, or the like. By having a library of absorbers 89 with fine, stepwise differences in electron beam absorption, different adjustments of the electron beam in fine increments can be delivered to treatment sites such as site 12. In the meantime, feedback strategies such as those described in U.S. Pat. No. 10,485,993 optionally may be used to stabilize the electron beam with high precision prior to tuning by the absorber 89. To change to another penetration depth setting, one or more different absorbers 89 are presented to the beam and/or the machine may be set to produce an electron beam with a different energy level that is presented to the one or more absorbers 89. The different absorbers 89 may be installed manually or via automation. U.S. Pat. No. 10,485,993 further describes how to use absorbers to help adjust an electron beam.

FIG. 2 shows absorber 89 mounted to applicator 86. The absorber 89 may be located in other positions and still provide effective tuning. Generally, the absorber 89 is deployed in the path 90 of the electron beam between the exit window 78 and the target site 12. Many suitable embodiments of absorber 89 are fabricated from one or more low Z materials above atomic number 4. Exemplary materials useful to form absorber 89 include carbon, aluminum, beryllium, and combinations of two or more of these. Higher Z materials could be used, but with the risk of generating undo amounts of Bremsstrahlung radiation.

FIG. 2 shows machine vision capability integrated with unit 26. In some embodiments, machine vision is achieved by mounting one or more endoscopes 93 onto applicator 86. Endoscope 93 allows real time video imaging of target site 12. Endoscope 93 or other machine vision capability is helpful to allow target site 12 to be viewed without obstruction by applicator 86, shield 88, or other components of unit 26 or system 10. As one advantage, endoscope 93 allows real time viewing of target site 12 as system 10 is set up and aimed at the target site 12. This can be helpful to make sure that system 10 is aimed properly at site 12 without undue misalignment or tilting. An operator can also view the captured image information to observe the site 12 during a treatment. This will allow the operator to capture image information to document the treatment. Also, the operator can observe to make sure that the substrate 14 (e.g., a patient) does not move out of the proper set up as a treatment proceeds. Endoscope 93 is very suitable for this, as endoscopes generally are flexible for easy mounting, capture high quality, real time images, and are inexpensive.

FLASH treatment times are very short (often less than 5 seconds or even less than 1 second or even occurring in tenths of a second or thousandths of a second or milliseconds or on the order of microseconds). Providing an accurate dose per pulse is highly desirable to allow accurate use and control of ionizing radiation in FLASH treatments. The accuracy of the dose per pulse is limited in one aspect by the ability of the system 10 to produce stable, uniform beam pulses quickly. Toward this goal, system 10, including unit 26, may be configured with one or more optional features incorporated into circuitry to generate gun pulses, the shape of the pulses that power the microwave or RF energy pulses, the automatic frequency control functionality, and/or the timing to allow the microwave or RF power and gun pulses to be synchronized (electron beam produced) or out of synchronization (no electron beam produced.

The circuitry that generates the gun pulse desirably is configured to generate a more stable pulse shape with faster rise and decay times for better repeatability and less susceptibility to temperature drift. To accomplish this, an electronic switching device was incorporated into the design of the grid pulse circuitry that allowed switching to occur with sufficient rapidity for effective actuation in the time scales associated with FLASH treatments. Additionally, the shape of the high voltage pulse that powers the magnetron preferably is configured for more stable magnetron operation. To accomplish this, control of the switching device for a solid state modulator (a high voltage power supply that provides high voltage pulses to a magnetron) preferably is modified to make the slope of the rise and fall times more vertical. Also, the automatic frequency control system desirably may be configured to provide accurate tracking of the magnetron frequency to the linear accelerator resonant frequency. To accomplish this, the frequency response of an AFC servo system can be increased (quicker response time) by adjustments to the control software of a magnetron tuner motor in order to provide a frequency response more effective in the time scales of typical FLASH treatments.

The control system 28 desirably may be configured to allow the microwave or RF power pulses and gun pulses to power on in an out of synchronization or out-of-coincidence state (no beam produced) until the system 28 comes to thermal stability. Once thermal stability is reached, the pulses can then be synchronized, or switched into coincidence, to generate the beam used for a treatment.

As an advantage, embodiments of system 10, such as the MOBETRON electron beam machine, may be configured so that the operator can select from one or more non-FLASH modes of treatment as well as one or more FLASH modes of treatment. Generally, non-FLASH modes may be switched to FLASH modes by increasing the dose per pulse and implementing partial pulse control if not already active. Increasing the dose rate by pulse can be accomplished by implementing one or more strategies selected from increasing the amplitude of the electron beam current, increasing the duty factor of the electron beam current, increasing the pulse width, and/or increasing the ratio of the dose rate to the electron beam current.

For example, increasing the amplitude of the beam current may be accomplished by one or more of increasing the gun voltage, increasing the grid voltage; modifying the RF system, including the magnetron, and if necessary the modulator, to compensate for the increase in RF power needed to accelerate the higher gun current; modifying the design of the linear accelerator cavities to improve the capture ratio of the gun current; and/or increasing the length of the linear accelerator to reduce the required RF power. Increasing the duty factor of the beam may be accomplished by one or more of increasing the gun and/or RF pulse widths and/or increasing the pulse repetition frequency of the beam pulses. Increasing the ratio of dose rate to beam current may be accomplished by one or more of reducing the distance from the beam source (the flattening filter) to the treatment plane to concentrate the beam in a smaller treatment area (inverse square law) and/or modifying the scattering foil and or flattening filter to reduce the number of electrons that are scattered out of the treatment field.

FIG. 3 shows an alternative configuration of system 10 of FIG. 2. System 10 of FIG. 3 is identical to system 10 as shown in FIG. 2 except that a different applicator 100 and an alternative field defining shield 102 are used. In this illustration, applicator 100 is longer than applicator 86 (FIG. 2), while shield 102 is smaller and helps shape a more tightly defined electron beam field than shield 88 (FIG. 2). FIG. 3 shows the modular capabilities of system 10 with respect to independently choose and use different applicators and/or shields to easily adapt to the needs of a variety of different electron beam treatments and circumstances. The applicators (e.g., applicator 86) are modular in the sense that a library may include an inventory of two or more applicators, each of which is interchangeably mounted on the unit 26. Similarly, the shields (e.g., shield 88) are modular in the sense that a library may include an inventory of two or more shields, each of which is interchangeably mounted on the unit 26.

Figure 4:
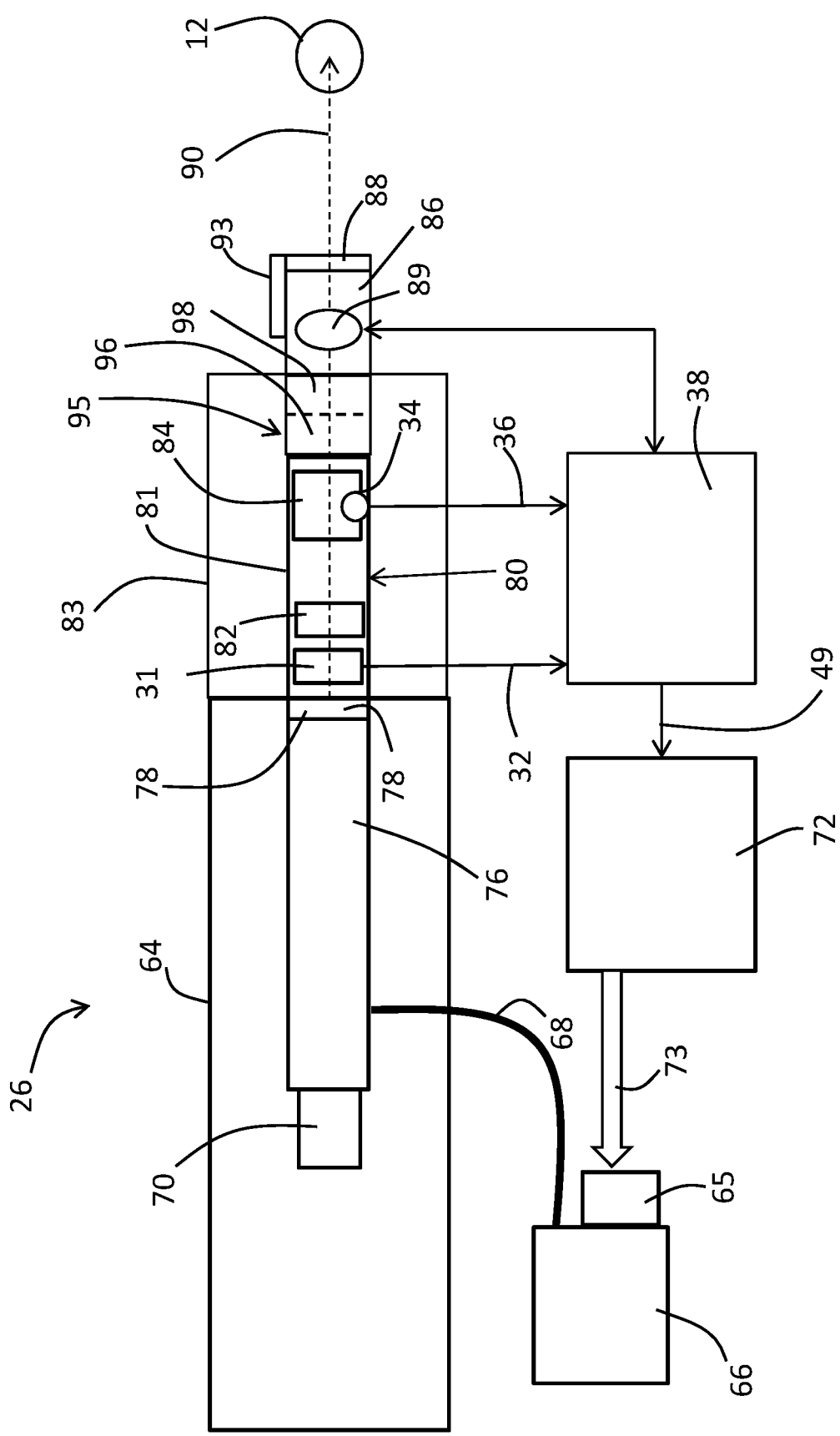
FIG. 4 schematically shows an alternative embodiment of an electron beam generation unit useful in the electron beam radiation system of FIG. 1.

FIG. 4 shows another alternative embodiment of the electron beam generation unit 26. The system 10 of FIG. 3 is identical to the system 10 of FIG. 2 except that the microwave source 66 and a portion of the microwave network 68 are external to housing 64. Rotational motion between the two ends of the network 68 can be practiced by incorporating one or more rotary joints into network 68 according to conventional practices.

Figure 5:
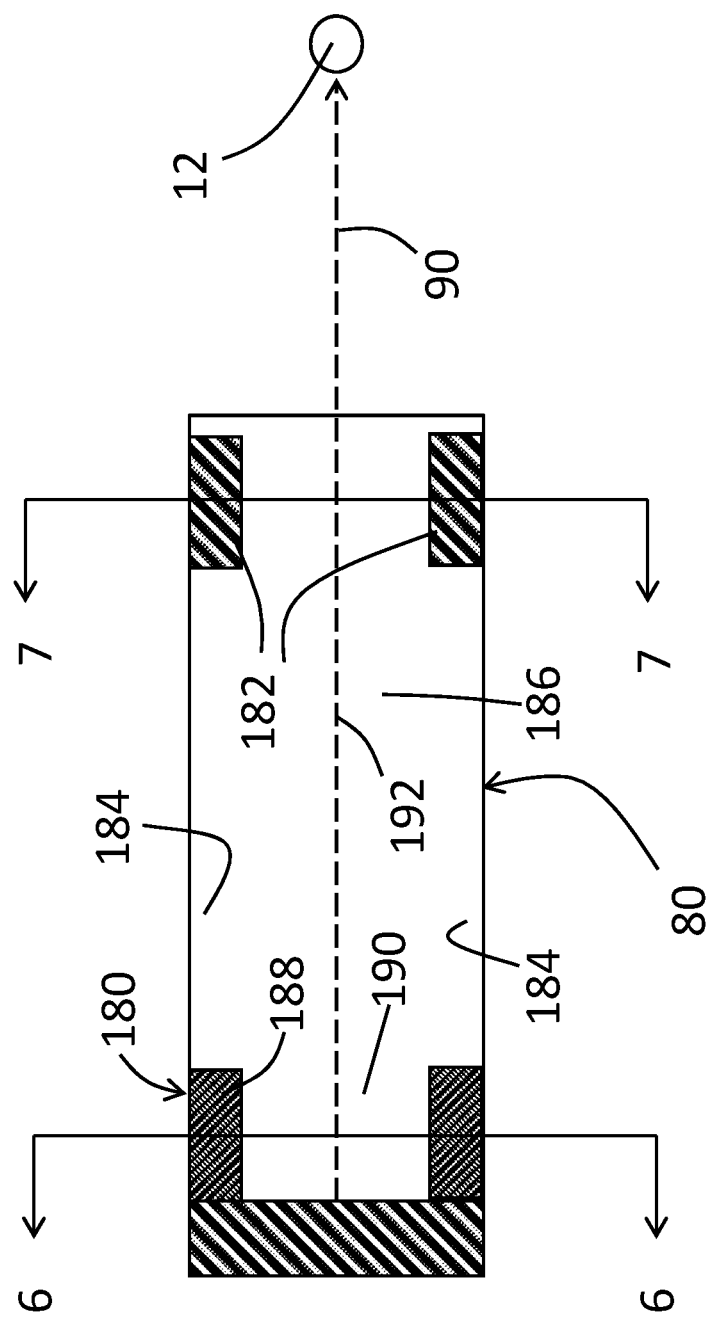
FIG. 5 schematically shows an alternative embodiment of an electron beam generation unit useful in the electron beam radiation system of FIG. 1.
Figure 7:
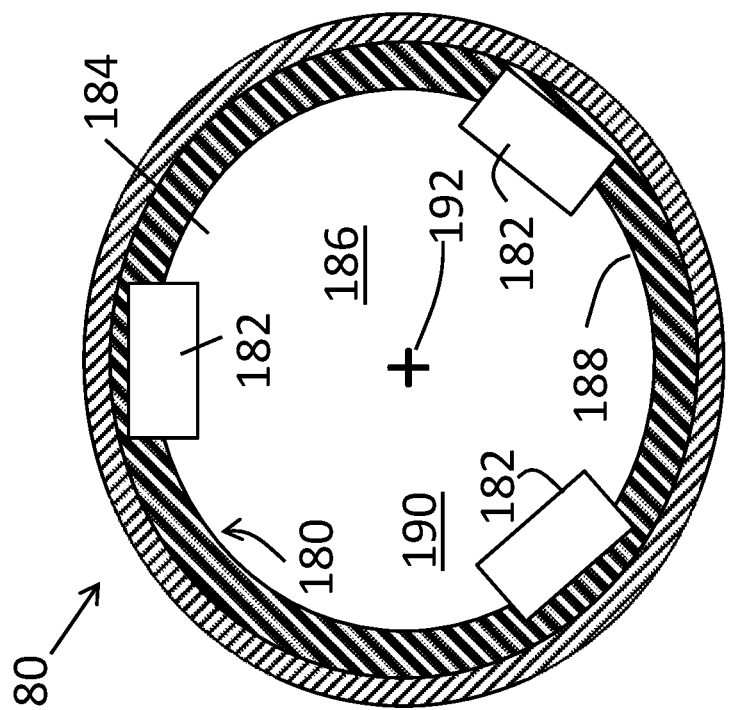
FIG. 7 schematically shows a cross-section of FIG. 5 taken through line 7-7.
Figure 6:
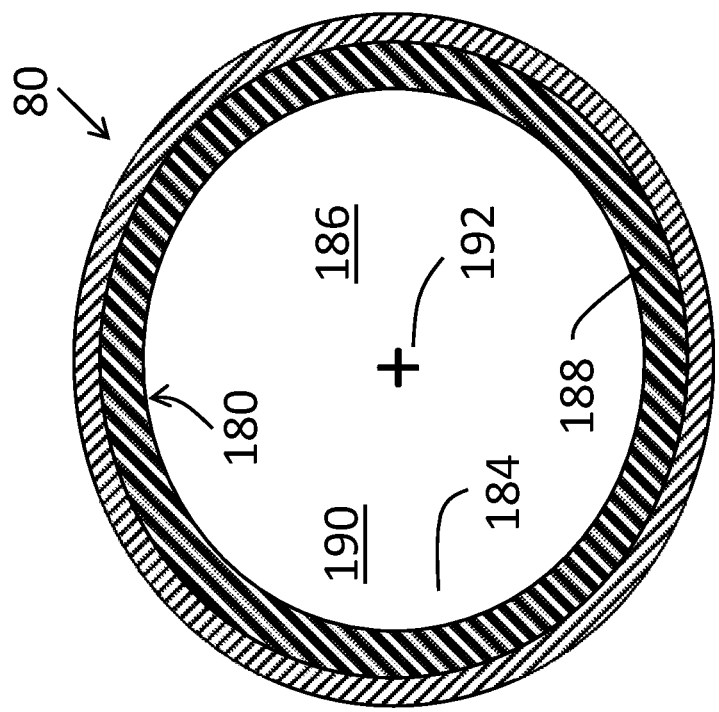
FIG. 6 schematically shows a cross-section of FIG. 5 taken through line 6-6.

FIGS. 5, 6, and 7 show an alternative embodiment of a portion of unit 26 of system 10 in which sensor 31 of FIG. 2 is in the form of a toroid sensor 180, while sensor 34 of FIG. 2 is in the form of an array of ion chambers 182 deployed around the periphery 184 of the electron beam channel 186 inside collimator assembly 80. In this embodiment, toroid sensor 180 includes an annular housing 188 that encases sensing components (not shown). A central bore 190 is open and provides an unobstructed aperture for passage of the electron beam. The central axis 192 of the channel 186 generally corresponds to the central axis of the electron beam (ebeam or beam) flowing along pathway 90 to the target site 12. Three ion chambers 182 are deployed as a uniform array to sense characteristics of the beam at the channel periphery. By detecting characteristics at a plurality of regions around the channel periphery, the readings from the ion chambers 182 can indicate if the beam is homogenous (e.g., the readings are substantially similar) or if the beam is non-uniform (e.g., the readings are insufficiently similar).

FIG. 7 shows an array of ion chambers 182 including three ion chambers 182 deployed symmetrically around the central axis 192. In other embodiments, an array may include two ion chambers 182, or more than three ion chambers 182, such as 4 to 8 ion chambers 182. In some embodiments, even a single ion chamber 182 may be used instead of an array where beam sensing with ion chamber redundancy and the ability to monitor multiple peripheral regions are not desired.

FIG. 8 schematically shows how electron gun pulse characteristics correlate to the output signal of a beam monitor such as sensors 31 and/or 34, described above, and then how the output signal correlates to the cumulative dose deposited into the target site. FIG. 8 includes a plot 200 of electron gun voltage as a function of time. The plot 200 shows that the electron gun voltage is applied as pulses 202 (full) and 203 (partial) over time. The pulses have a frequency that is the inverse of the period, T. Each pulse 202 is characterized by a pulse width, W. The pulses are flat on top, indicating that the voltage advantageously is constant and uniform during the pulse. Each pulse 202 also has a rise profile 206 and a decay profile 208. The profiles 206 and 208 are substantially vertical, indicating the pulses start and end quickly. The last pulse 203 is similar to pulses 202 except that pulse 203 is a partial pulse. The electron gun voltage is turned off to end pulse 203 at time t. Time t corresponds to the time at which the target dose 226 has been deposited into the treatment site. The dotted portion of pulse 203 shows the portion of pulse 203 that did not occur due to the termination of the electron gun voltage.

Still referring to FIG. 8, plot 210 shows the amplitude of the output signal of a beam monitor as a function of time. In this illustration, the beam monitor is a toroid sensor used as sensor 31 (see e.g., FIG. 2). The output signal correlates to the instantaneous dose rate as the treatment proceeds. Plot 210 shows how the beam monitor detects the electron beam dose rate as pulses 212 (full) and 203 (partial) as a function of time. The horizontal time scale of plot 210 matches the time scale of plot 200 to show how pulses 202/203 are synchronized and occur at the same time and with the same frequency as pulses 212/213. Each pulse 212 also has a rise profile 216 and a decay profile 218. The profiles 216 and 218 are substantially vertical, indicating the pulses start and end quickly. Pulse 213 is a partial pulse that ends at time t, to show how termination of partial pulse 203 promptly ends pulse 213, thus showing the prompt termination of the electron beam using partial pulse control strategies. The dotted portion of pulse 213 shows the portion of pulse 213 that did not occur due to partial pulse control strategies.

Still referring to FIG. 8, plot 220 shows the cumulative dose 225 deposited by the electron beam of plot 210 as a function of time. The horizontal time scale of plot 220 matches the time scales of plots 210 and 200 to show how the cumulative dose is synchronized with the electron gun pulses 202/203 and the electron beam pulses 212/213. Plot 220 shows how the cumulative dose increases linearly in rises 224 occurring during each pulse 202/203 and 212/213. The increase is linear because each pulse in plots 200 and 210 has a uniform magnitude during its duration. In between each rise 224 is a plateau 227 during which the instantaneous cumulative dose remains constant. This corresponds to regions of plots 200 and 210 in which no pulses are occurring. Hence, no additions to the cumulative dose are made.

Plot 220 shows a desired target dose 226. Plot 220 shows how the cumulative dose reaches the target dose 226 at the time t, which is when the pulses 202/203 and 212/213 are stopped. This shows how partial pulse control can stop dosing in the middle of a pulse 213 or 203 when the desired target dose 226 is reached. This provides substantially more accurate dosing as compared to approaches that only control on whole pulses. Partial pulse control is particularly advantageous in FLASH treatment regimes in which a whole pulse, and even a partial pulse, is a significant portion (e.g., at least 10%, or even at least 5%, or even at least 3%, or even at least 1%) of the target dose 226.

Figure 9:
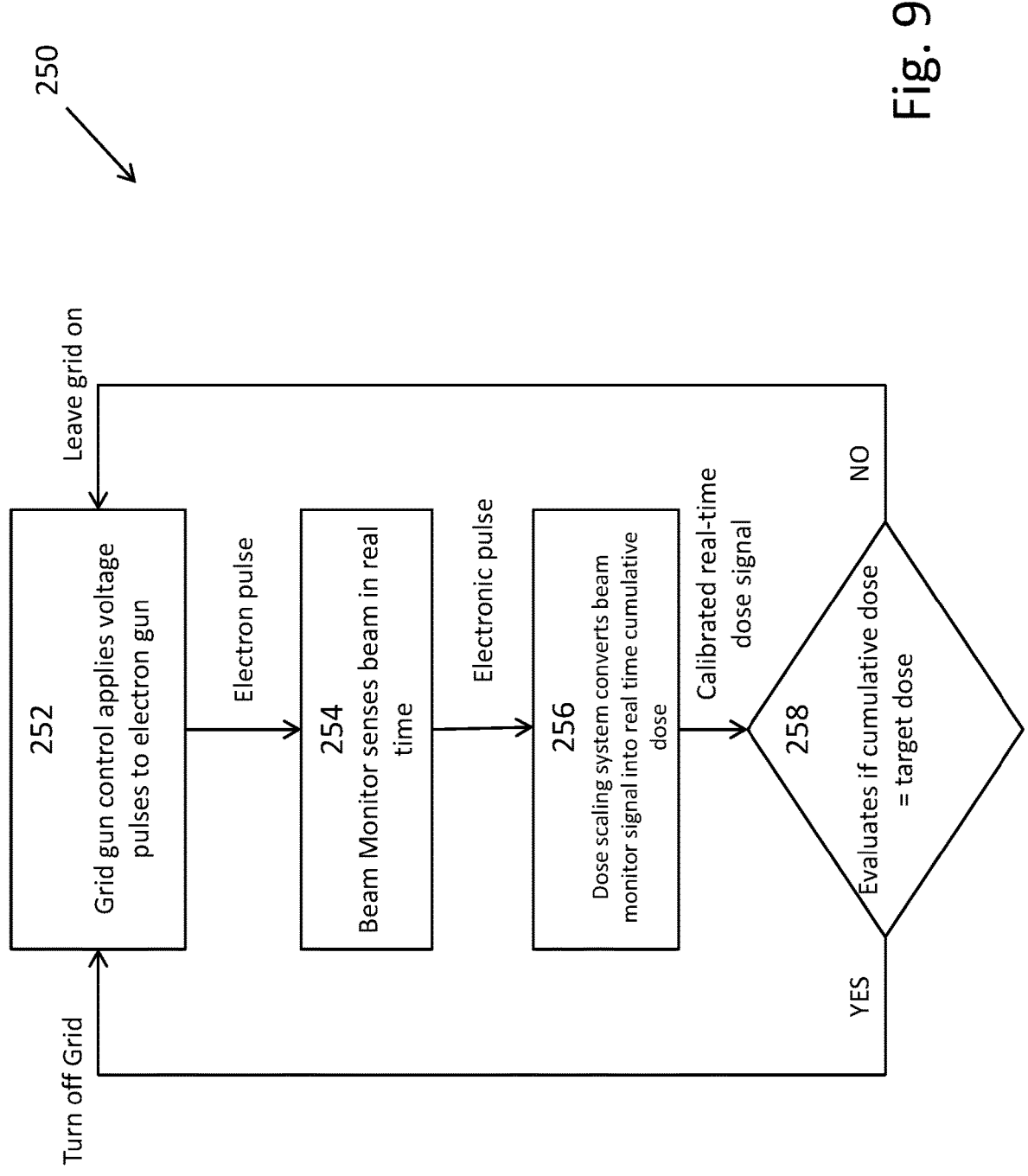
FIG. 9 schematically shows an illustrative methodology of the present invention that uses partial pulse control.

FIG. 9 schematically shows one methodology 250 for implementing the dose control strategy of FIG. 8. In step 252 of methodology 250, the electron gun control functionality applies voltage to the electron gun in pulses. Grid gun control electronics generates the amplitude, pulse width, and pulse frequency of the control voltage applied to the electron gun grid. This grid voltage controls the gun current that is injected into the linear accelerator and ultimately the beam current that exits the accelerator. For example, this could produce the voltage pulses 202 of graph 200 in FIG. 8.

After applying voltage pulses to the electron gun, the electron beam is generated and is pulsed at the target site. The beam current flows out of the accelerator and into the detection aperture of the beam monitor in the form of sensor 31 (see FIGS. 1a-1f and 2). For purposes of this discussion, sensor 31 is in the form of a toroid sensor. The electron beam goes through the center of the toroid sensor and induces an output signal as the treatment proceeds, which is measured by the associated electronics in step 254. This signal is an accurate, real time representation of the amplitude and shape of the beam pulses 212 and 213 as depicted in graph 210 of FIG. 8.

The signal magnitudes of the pulses 212 and 213 correlates to the instantaneous dose rate as the treatment proceeds. In step 256, the output of the toroid sensor is fed to a dose scaling functionality of the control system 28 (FIGS. 1a-1f). This functionality applies dose scaling functionality that is calibrated to convert the output signal of the toroid sensor into a dose rate associated with the dose delivered to the target site as a function of time. The dose rate can be integrated to provide the cumulative dose at any time during the treatment. The profile of the cumulative dose is shown by graph 220 of FIG. 8.

In step 258, control system 28 evaluates if the cumulative dose signal at a particular time is equal to the total target dose 226. If the answer of the evaluation at a time $t_i$ is yes, the control system 28 transmits a signal 260 to terminate the voltage applied to the electron gun, thereby terminating the electron beam at time t. If time t occurs in the middle of a pulse 203/213, the pulse is terminated as a partial pulse to thereby accurately deliver a cumulative dose that matches the target dose 226. If the answer is no, the methodology 250 is repeated.

The electron source 70 (FIG. 2) often is the rate determining factor for time resolution of the system operation. Therefore, controlling the grid allows rapid termination of the electron beam. For example, a typical grid cycling time of an electron gun may be on the order of about 0.1 microseconds (about 100 nanoseconds). This means that step 258 may be practiced via control of the grid mechanism for such gun to allow the electron beam to be terminated with a precision of about 0.1 microseconds. Note also the control of the grid mechanism allows the amplitude, pulse width, pulse frequency, and duty cycle of the electron gun pulses to be controlled.

FIG. 9 shows that the present invention monitors the total dose delivered to the patient in a treatment session as the treatment proceeds. The present invention allows termination of the electron beam during a pulse if the target dose level has been reached, thus delivering only a partial final pulse.

The control methodology 250 of FIG. 9 desirably monitors the electron beam and evaluates the cumulative dose at a frequency suitable to provide accurate control of the electron beam termination. In suitable embodiments, the control occurs at a frequency that is greater than the frequency of pulses 212, or even at least 5 times the frequency of the pulses 212, or even at least 10 times the frequency of pulses 212, or even at least 50 times the frequency of pulses 212, or even at least 100 times the frequency of the pulses 212. Monitoring the electron beam at higher frequency tends to provide more accurate control of the total delivered dose. For example, assuming a 50% duty cycle, monitoring at a frequency that is 10× the pulse frequency allows the dose to be controlled to within 1/5 of a pulse. In contrast, monitoring at a frequency that is 50× the pulse frequency at a 50% duty cycle allows the dose to be controlled to within 1/25 of a pulse.

The methodology 250 provides an approach in which dose monitoring as a treatment proceeds is used to deliver all but the last pulse at a fixed pulse width, while the last pulse is delivered with a smaller pulse width or by terminating the radiation mid-pulse. The smaller partial pulse width of the last pulse is dynamically determined in real time by monitoring the cumulative dose delivered to the target site. Terminating the last pulse early is much faster and less complex than dynamically adjusting the last pulse width to provide the required needed last portion of the dose.

Figure 10:
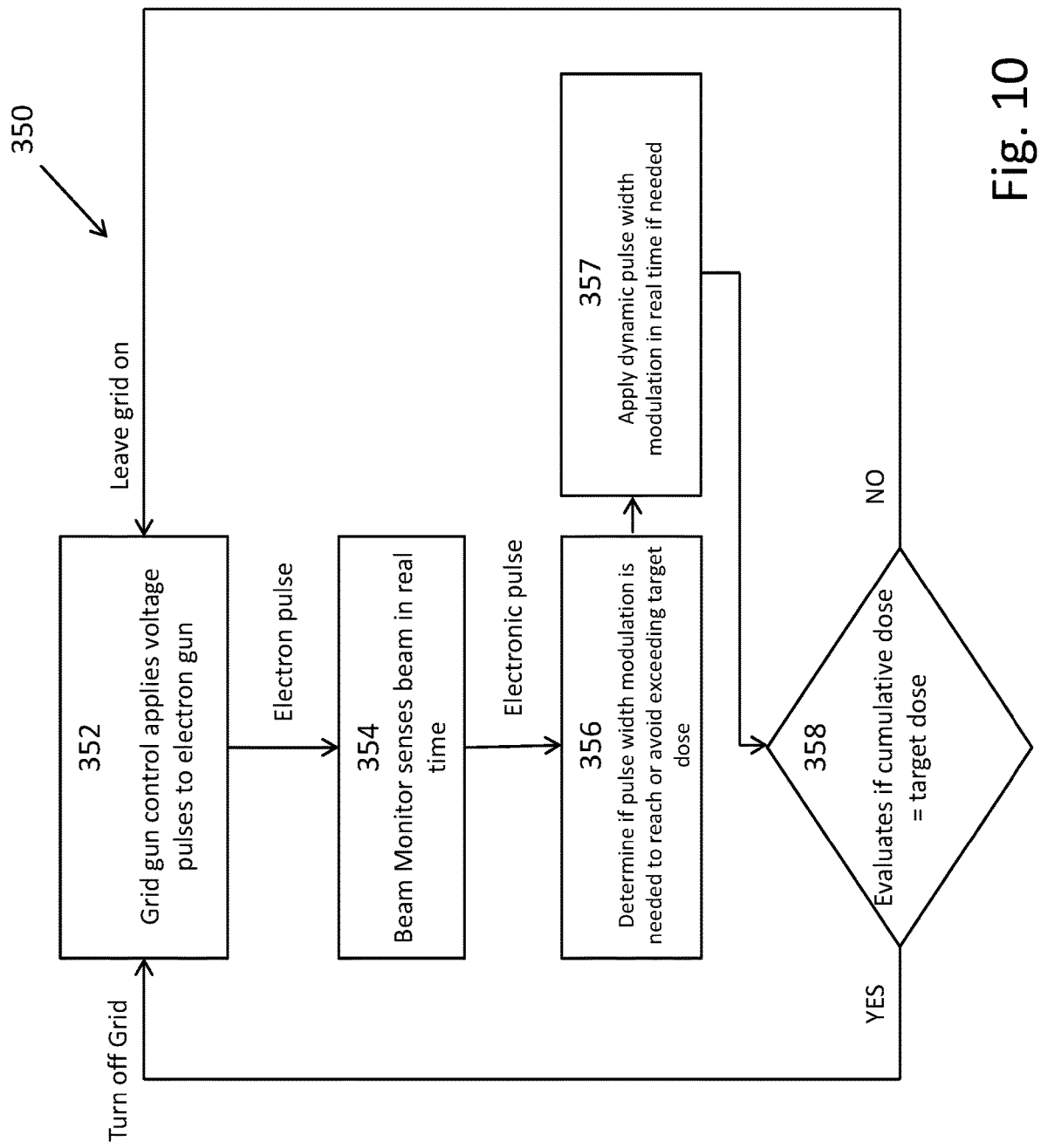
FIG. 10 schematically shows an illustrative methodology of the present invention that uses dynamic pulse width control.

FIG. 10 schematically shows another illustrative methodology 350 for implementing a dose control strategy of the present invention. In step 352 of methodology 350, the electron gun control functionality applies voltage to the electron gun in pulses. Grid gun control electronics generates the amplitude, pulse width, and pulse frequency of the control voltage applied to the electron gun grid. This grid voltage controls the gun current that is injected into the linear accelerator and ultimately the beam current that exits the accelerator.

After applying voltage pulses to the electron gun, the electron beam is generated and is pulsed at the target site. The beam current flows out of the accelerator and into the detection aperture of the beam monitor in the form of sensor 31 (FIGS. 1a-1f and 2). For purposes of this discussion, sensor 31 is in the form of a toroid sensor. The electron beam goes through the center of the toroid sensor and induces a real time signal that is measured by the associated electronics in step 354. This signal may be an accurate, real time representation of the amplitude and shape of the beam pulses.

In step 356, the output signal of the toroid sensor is fed to a control system to determine if the current pulse width is too wide or too narrow such that applying one or more additional pulses will exceed the target dose. If too wide or too narrow, pulse width modulation is needed to deliver one or more subsequently modified pulses in a manner effective to allow the target dose to be accurately achieved.

In step 357, the control system applies dynamic pulse width modulation to either increase and/or narrow the pulse width of one or more additional pulses so that the target dose is delivered.

In step 358, control system evaluates if the cumulative dose at a particular time is equal to the desired target dose. If the answer of the evaluation at a time $t_i$ is yes, the control system transmits a signal to terminate the voltage applied to the electron gun, thereby terminating the electron beam at time t. If the answer is no, the methodology 350 is repeated. In parallel, as a safety protocol, the total cumulative dose delivered to the target site can be monitored so that the beam can be terminated in an emergency in the event that the target dose is reached while a pulse is still ongoing or if one or more pulses might still yet occur.

FIG. 10 shows that the present invention monitors the total dose delivered to the patient in a treatment session as a treatment proceeds and allows dynamic modulation of the pulse widths as a treatment proceeds so that termination of the electron beam occurs upon a predetermined total dose level has been reached.

Figure 11:
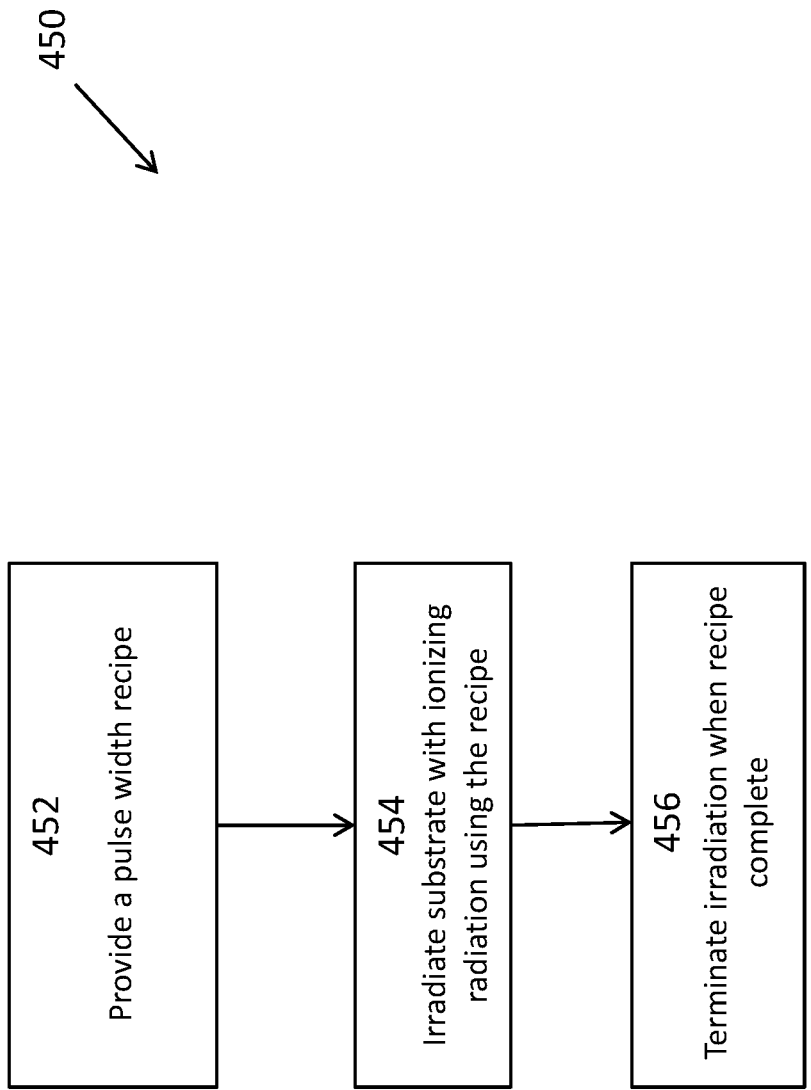
FIG. 11 schematically shows an illustrative methodology of the present invention that uses at least one pre-determined pulse width recipe.

FIG. 11 schematically shows another illustrative methodology 450 for implementing a dose control strategy of the present invention. In step 452 of methodology 450, a pulse width recipe is provided that incorporates a plurality of pulse widths. The pulse width recipe is created so that pulsed ionizing radiation whose pulses implement the recipe deposit a desired target dose to a substrate.

In step 454, the pulse width recipe is used to deposit the pulsed, ionizing radiation into the substrate by irradiating the substrate with ionizing radiation.

In step 456, irradiation of the substrate is terminated when the pulse width recipe is completed. In parallel, as a safety protocol, the total cumulative dose delivered to the target site can be monitored so that the beam can be terminated in an emergency in the event that the target dose is reached while the pulse recipe is still ongoing.

Figure 12:
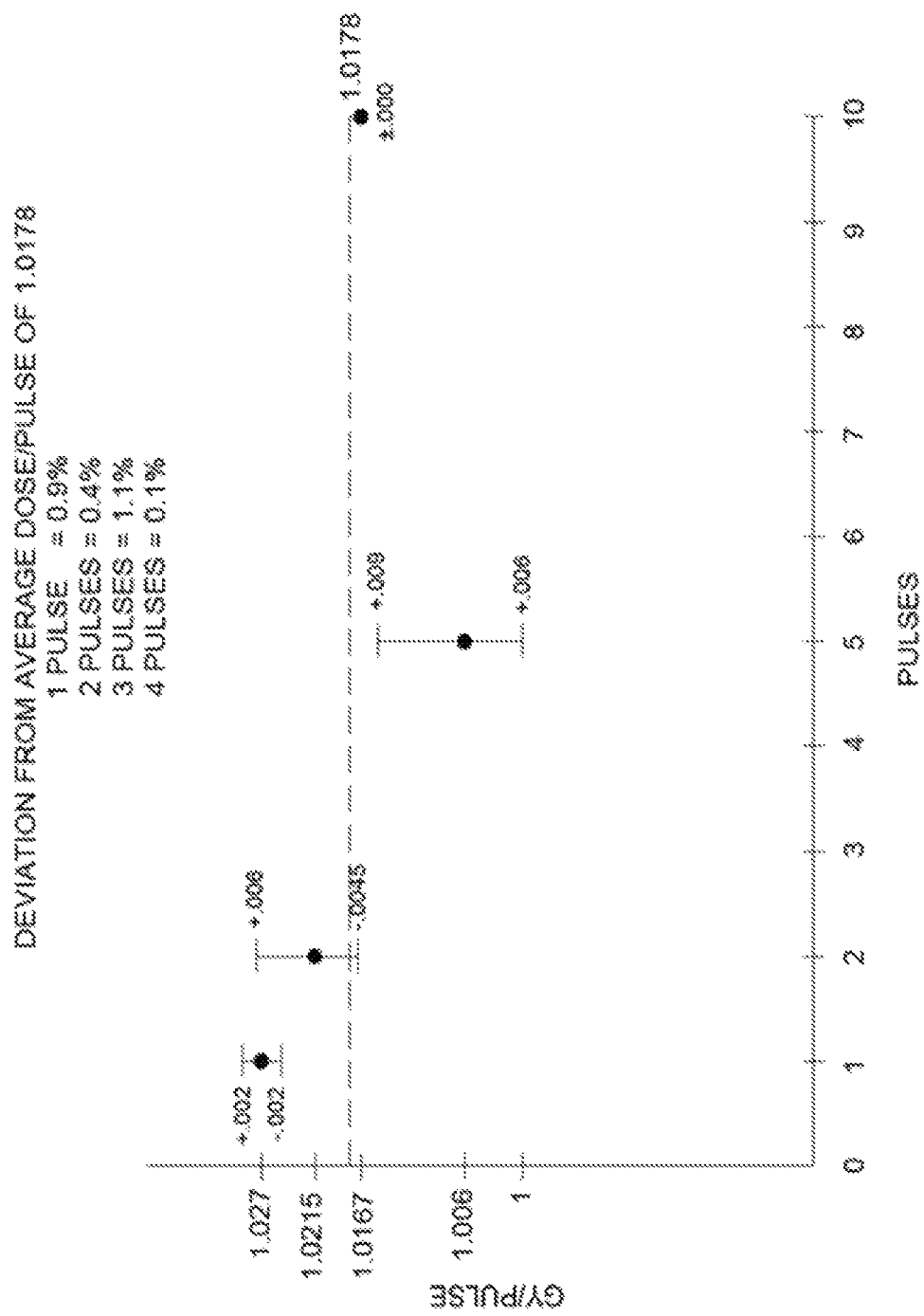
FIG. 12 is a graph showing how the commercially available MOBETRON electron beam machine delivers total doses in a FLASH treatment at 6 MeV that are linear with respect to the number of pulses and that the total dose delivered for particular pulse counts is highly uniform.

FIG. 12 is a graph showing how the commercially available MOBETRON electron beam machine delivers total doses in a FLASH treatment at 6 MeV that are linear with respect to the number of pulses and that the total dose delivered for particular pulse counts is highly uniform.

Figure 13:
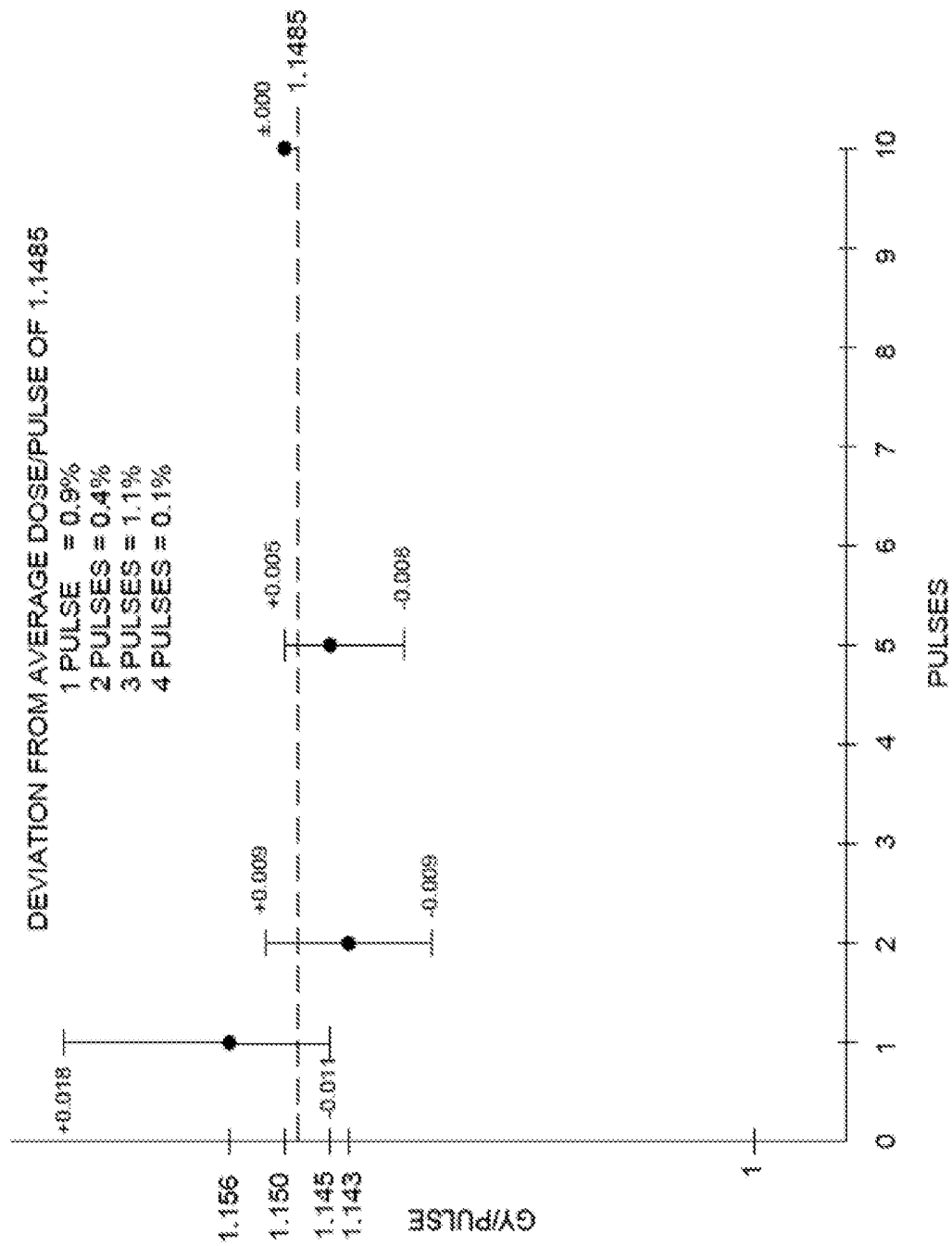
FIG. 13 is a graph showing how the commercially available MOBETRON electron beam machine delivers total doses in a FLASH treatment at 9 MeV that are linear with respect to the number of pulses and that the total dose delivered for particular pulse counts is highly uniform.

FIG. 13 is a graph showing how the commercially available MOBETRON electron beam machine delivers total doses in a FLASH treatment at 9 MeV that are linear with respect to the number of pulses and that the total dose delivered for particular pulse counts is highly uniform.

The present invention will now be described with respect to the following representative examples.

EXAMPLE 1

TABLE 1

Output vs Distance-6e, Full Duty Factor (45 PPS, 4 uS Pulse Width)

| Distance From Flattening Filter (cm) | Distance from Bottom of Applicator (cm) | Max Field Size (cm) | Standard Output (Gy/min) | Flash Output (Gy/min) | Flash Output (Gy/sec) | Notes |
|---|---|---|---|---|---|---|
| 63.0 | 20 | N/A | 5.63 | 1,303 | 22 | 10 cm applicator, 20 cm below it |
| 43.0 | 0.0 | 10.0 | 10.00 | 2,314 | 39 | 10 cm Applicator (standard configuration) |
| 35.5 | −7.5 | 10.0 | 12.20 | 2,823 | 47 | No applicator |
| 25.5 | −17.5 | 7.7 | 20.15 | 4,662 | 78 | No applicator |
| 15.5 | −27.5 | 4.7 | 40.20 | 9,301 | 155 | At output of direct connect mount |
| 9.0 | −34.0 | 2.7 | 67.50 | 15,618 | 260 | At output of collimator |

Output vs Distance Notes:
Flash was tuned for 301.4 Gy/Min for a 10 cm field in 6e
flash output for 9.0 cm from flattening filter is an estimate The data in Table 1 shows that the MOBETRON electron beam machine may be operated to generate FLASH dose rates at an energy level of 6 MeV and that the FLASH output (Gy/s) is correlated (inverse square law) to the distance (cm) between the flattening filter and the location along the electron beam pathway at which the FLASH output is measured. The data also shows the impact of field size on output when the beam parameters of the MOBETRON has been adjusted to operate at FLASH dose rates. In this experiment, for FLASH dose rates, the MOBETRON pulse width is set at 4.0 μsec and the pulse rate is set to 45 pulses per second (PPS). The output is compared to the standard (non-FLASH) MOBETRON output of 10 Gy/min. (1.6 μsec pulse width and 30 PPS). Measurements were made using a Marcus chamber in air. The distances are measured from the standard MOBETRON treatment distance with an applicator in place.

EXAMPLE 2

TABLE 2

Output vs Distance-9e, Full Duty Factor (45 PPS, 4 uS Pulse Width)

| Distance from Flattening Filter (cm) | Distance from Bottom of Applicator (cm) | Max Field Size (cm) | Standard Output (Gy/min) | Flash Output (Gy/min) | Flash Output (Gy/sec) | Notes |
|---|---|---|---|---|---|---|
| 63.0 | 20 | N/A | 5.63 | 3,205 | 53 | 10 cm applicator, 20 cm below it |
| 43.0 | 0.0 | 10.0 | 10.00 | 5,693 | 95 | 10 cm Applicator (standard configuration) |
| 35.5 | −7.5 | 10.0 | 12.20 | 6,945 | 116 | No applicator |
| 25.5 | −17.5 | 7.7 | 20.15 | 11,470 | 191 | No applicator |
| 15.5 | −27.5 | 4.7 | 40.20 | 22,884 | 381 | At output of direct connect mount |
| 9.0 | −34.0 | 2.7 | 67.50 | 38,424 | 640 | At output of collimator |

Output vs Distance Notes:
Flash was tuned for 301.4 Gy/Min for a 10 cm field in 6e
Flash output for 9.0 cm from flattening filter is an estimate The data in Table 2 was obtained in the same manner as the data as Table 1 but with the MOBETRON operating at 9 MeV. The data of Table 2 leads to the same conclusions that the MOBETRON electron beam machine may be operated to generate FLASH dose rates at an energy level of 9 MeV and that the FLASH output (Gy/s) is correlated (inverse square law) to the distance (cm) between the flattening filter and the location along the electron beam pathway at which the FLASH output is measured.

EXAMPLE 3

The MOBETRON was operated to determine whether the dose per pulse was sufficiently uniform so that termination with a partial pulse would achieve an accurate dose delivery. The MOBETRON was run with a nominal dose rate of 30 Gy/sec as that was the maximum dose rate that did not saturate the electronics of the dosimetry system used for the experiment. FIG. 12 and Table 3 below show the results for 1, 2, 5 and 10 pulses at 6 MeV, respectively. The pulse width was 3.7 μsec (microseconds) and the grid voltage was 6 volts at 6 MeV.

TABLE 3

Dose Linearity
6 e/6 V grid/100 a mag/3.5 v gun/13 mm dmax/3.7 uS p-width

| # or Pulses | Gy | Gy/Sec | Gy/Pulse |
|---|---|---|---|
| 1 | 1.025 | 30.75 | 1.025 |
| 1 | 1.029 | 30.87 | 1.029 |
| 1 | 1.027 | 30.81 | 1.027 |
| 2 | 2.04 | 30.6 | 1.02 |
| 2 | 2.055 | 30.825 | 1.0275 |
| 2 | 2.034 | 30.51 | 1.017 |
| 5 | 5.006 | 30.036 | 1.0012 |
| 5 | 5.001 | 30.006 | 1.0002 |
| 5 | 5.076 | 30.456 | 1.0152 |
| 10 | 11.23 | 33.69 | 1.123 |
| 10 | 11.33 | 33.99 | 1.133 |
| 10 | 11.33 | 33.99 | 1.133 |

EXAMPLE 4

The MOBETRON was operated to determine whether the dose per pulse was sufficiently uniform so that termination with a partial pulse would achieve an accurate dose delivery. The MOBETRON was run with a nominal dose rate of 30 Gy/sec as that was the maximum dose rate that did not saturate the electronics of the dosimetry system used for the experiment. FIG. 13 and Table 4 below show the results for 1, 2, 5 and 10 pulses at 9 MeV, respectively. The pulse width was 3.7 μsec and the grid voltage was 5.7 volts at 9 MeV.

TABLE 4

Dose Linearity
9 e/5.7 V gird/100 A mag/3.5 v gun/19 mm dmax/3.7 uS p-width

| # or Pulses | Gy | Gy/sec | Gy/pulse |
|---|---|---|---|
| 1 | 1.145 | 34.35 | 1.145 |
| 1 | 1.149 | 34.47 | 1.149 |
| 1 | 1.174 | 35.22 | 1.174 |
| 2 | 2.304 | 34.56 | 1.152 |
| 2 | 2.268 | 34.02 | 1.134 |
| 2 | 2.29 | 34.35 | 1.145 |
| 5 | 5.738 | 34.428 | 1.1476 |
| 5 | 5.75 | 34.5 | 1.15 |
| 5 | 5.687 | 34.122 | 1.1374 |
| 10 | 11.91 | 35.73 | 1.191 |
| 10 | 12.03 | 36.09 | 1.203 |
| 10 | 11.97 | 35.91 | 1.197 |

All patents, patent applications, and publications cited herein are incorporated by reference in their respective entireties for all purposes. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. An ionization radiation system that deposits a target dose of pulsed ionizing radiation into a substrate during a treatment, said ionization radiation system comprising:
   a. a pulsed ionizing radiation beam that is aimed at and deposits ionizing radiation into the substrate during the treatment, wherein the pulsed ionizing radiation beam comprises fluence characteristics as the treatment proceeds; and
   b. a control system comprising at least one sensor that monitors the pulsed ionizing radiation beam as the treatment proceeds, wherein the at least one sensor comprises a toroid sensor, and wherein:

i. the toroid sensor provides an output signal indicative of the fluence characteristics of the pulsed ionizing radiation beam as the treatment proceeds;
ii. the control system comprises program instructions that use information comprising the output signal to determine dose information indicative of the cumulative dose of the ionizing radiation that is deposited into the substrate as the treatment proceeds;
iii. the toroid sensor has a central bore, and the pulsed ionizing radiation beam passes through the central bore of the toroid sensor;
iv. the control system comprises program instructions that, as the target dose approaches as the treatment proceeds, proactively adjust a pulse duration of the pulsed ionizing radiation beam so that the cumulative dose deposited into the substrate matches the target dose when the depositing of the pulsed ionizing radiation into the substrate is terminated; and
v. the control system comprises program instructions, that as the target dose approaches, issue a stop signal in advance of reaching the target dose that causes the depositing of the pulsed ionizing radiation into the substrate to be terminated when the target dose is reached.

2. The system of claim 1, wherein the substrate is a human or animal patient.

3. The system of claim 1, wherein the pulsed ionizing radiation beam has an energy in the range from 4 MeV to 100 MeV.

4. The system of claim 1, wherein the adjusted pulse duration provides a pulse width that is less than a full pulse width.

5. The system of claim 1, wherein the pulsed ionizing radiation beam comprises an adjusted pulse duration such that at least one pulse has a pulse width that is dynamically modulated as the treatment proceeds.

6. The system of claim 1, wherein the pulsed ionizing radiation beam is sourced from a triode electron gun.

7. The system of claim 1, wherein the pulsed ionizing radiation beam comprises a train of individual pulses having a constant amplitude.

8. The system of claim 1, wherein the control system comprises a plurality of toroid sensors.

9. The system of claim 1, wherein the pulsed ionizing radiation beam has an inner zone constituting from 70% to 80% of the cross-section area of the pulsed ionizing radiation beam and an outer peripheral zone constituting from 20% to 30% of the cross-section area of the pulsed ionizing radiation beam, and wherein at least one the toroid sensor is positioned in a manner effective to sense a beam characteristic in the outer peripheral zone of the pulsed ionizing radiation beam.

10. The system of claim 9, wherein the at least one sensor comprises a plurality of toroid sensors that are deployed in a manner effective to detect beam characteristics in the peripheral zone.

11. The system of claim 10, wherein the at least one sensor further comprises a plurality of ion chambers.

12. The system of claim 9, wherein the toroid sensor is positioned in a manner to sense a fluence characteristic of the pulsed ionizing radiation beam that is in the range from 0.01% to 70% of the fluence at the corresponding center line of the pulsed ionizing radiation beam.

13. The system of claim 1, wherein the system further comprises a triode electron gun that helps to generate the pulsed ionizing radiation beam and wherein the program instructions of step v comprise program instructions that, when executed, turn off the triode electron gun.

14. The system of claim 1, wherein the pulsed ionizing radiation beam is configured to deposit a dose of at least 1 Gy into the substrate per fraction.

15. The system of claim 14, wherein the dose is 5 Gy to 50 Gy per fraction.

16. The system of claim 15, wherein the pulsed ionizing radiation beam has a dose rate that is at least 1 Gy/s and is delivered in a time interval of 10 seconds or less.

17. The system of claim 16, wherein the dose rate is at least 30 Gy/s and the time interval is 1 second or less.

18. The system of claim 16, wherein the time interval is in the range from 0.01 milliseconds to 3 seconds.

19. The system of claim 16, wherein the dose rate is in the range from 1 Gy/s to 1500 Gy/s.

20. A method of using a pulsed beam of ionizing radiation to deposit a target dose of the ionizing radiation to a substrate during a treatment, comprising the steps of:
a. delivering the pulsed beam of ionizing radiation into the substrate, wherein the pulsed ionizing radiation comprises a train of one or more individual pulses, and wherein the pulsed beam of ionization radiation comprises fluence characteristics as the treatment proceeds;
b. using at least one sensor to provide an output signal indicative of the fluence characteristics of the pulsed beam of ionizing radiation as the treatment proceeds, wherein the at least one sensor comprises a toroid sensor having a central bore, and wherein the pulsed beam of ionizing radiation passes through the central bore of the toroid sensor;
c. using the output signal to determine dose information indicative of a total cumulative dose deposited into the substrate as the treatment proceeds;
d. comparing the cumulative dose to the target dose as the treatment proceeds;
e. as the target dose approaches as the treatment proceeds, proactively adjusting a pulse duration of the pulsed beam of ionizing radiation so that the cumulative dose deposited into the substrate matches the target dose when the depositing of the pulsed beam of ionizing radiation into the substrate is terminated; and
f. issuing a stop signal in advance of reaching the target dose that causes the depositing of the pulsed beam of ionizing radiation into the substrate to be terminated when the target dose is reached.

21. The method of claim 20, wherein the substrate is a human or animal patient.

22. The method of claim 21, wherein the beam of pulsed ionizing radiation is delivered to cancerous tissue.

23. The method of claim 20, wherein the pulsed beam of ionizing radiation has an energy in the range from 4 MeV to 100 MeV.

24. The method of claim 20, wherein the train of individual pulses comprises at least one full width pulse and at least one partial width pulse, wherein the at least one partial width pulse having a pulse width that is dynamically adjusted during the treatment.

25. The method of claim 20, wherein step f) comprises terminating the ionizing radiation at a time during a final pulse such that the final pulse is a partial pulse.

26. The method of claim 20, wherein step a) comprises using a triode electron gun to help provide the pulsed beam of ionizing radiation.

27. The method of claim 20, wherein the train of individual pulses has a constant amplitude.

28. The method of claim 20, wherein step b) comprises using a plurality of toroid sensors to sense the fluence characteristics of the pulsed beam of ionizing radiation.

29. The method of claim 20, wherein the pulsed beam of ionizing radiation is a beam that has an inner zone constituting from 70% to 80% of the cross-section area of the beam and an outer peripheral zone constituting from 20% to 30% of the cross-section area of the beam, and wherein step b) comprises sensing a beam characteristic in the outer peripheral zone of the beam.

30. The method of claim 29, wherein the at least one sensor comprises a plurality of toroid that sensors is deployed in a manner effective to detect beam characteristics in the peripheral zone.

31. The method of claim 29, wherein the toroid sensor is positioned in a manner to sense a fluence characteristic of the beam that is in the range from 0.01% to 70% of the fluence at the corresponding center line of the beam.

32. The method of claim 20, wherein the at least one sensor further comprises a plurality of ion chambers.

33. The method of claim 20, wherein step a) comprises using a triode electron gun to help provide the pulsed beam of ionizing radiation, and wherein step f) comprises turning off the triode electron gun.

34. The method of claim 20, wherein step f) occurs in a manner effective to deposit a dose of at least 1 Gy into the substrate per fraction.

35. The method of claim 34, wherein the dose is 5 Gy to 50 Gy per fraction.

36. The method of claim 20, wherein step a) comprises delivering the pulsed beam of ionizing radiation at a dose rate of at least 1 Gy/s and step f) occurs in a manner such that the treatment occurs in a time interval of 10 seconds or less.

37. The method of claim 36, wherein the dose rate is at least 30 Gy/s and the time interval is 1 second or less.

38. The method of claim 36, wherein the time interval is in the range from 0.01 milliseconds to 3 seconds.

39. The method of claim 36, wherein the dose rate is in the range from 1 Gy/s to 1500 Gy/s.

40. The method of claim 20, further comprising the steps of:
   a. providing a pulse width recipe that incorporates a plurality of different pulse widths into a pulse train; and
   b. using the pulse width recipe to deliver the pulsed beam of ionizing radiation to the substrate in a manner effective to deposit the target dose into the substrate.

41. A method of using pulsed electron beam radiation to deposit a target dose into a substrate during a treatment, comprising the steps of:
   a) using a triode electron gun to help generate the pulsed electron beam radiation, wherein the pulsed electron beam radiation comprises a train of one or more individual pulses, and wherein the pulsed electron beam radiation comprises fluence characteristics as the treatment proceeds;
   b) causing the pulsed electron beam radiation to irradiate the substrate;
   c) using at least one sensor to provide an output signal indicative of the fluence characteristics of the pulsed electron beam radiation as the treatment proceeds, including providing the output signal during the one or more individual pulses, wherein the at least one sensor comprises a toroid sensor having a central bore, and wherein the pulsed beam of ionizing radiation passes through the central bore of the toroid sensor;
   d) using the output signal to determine dose information indicative of a total cumulative dose deposited into the substrate as the treatment proceeds;
   e) comparing the cumulative dose to the target dose as the treatment proceeds;
   f) proactively adjusting a pulse duration of the pulsed beam of ionizing radiation so that the cumulative dose deposited into the substrate matches the target dose when the depositing of the pulsed beam of ionizing radiation into the substrate is terminated; and
   g) issuing a stop signal in advance of reaching the target dose that causes the depositing of the pulsed beam of ionizing radiation into the substrate to be terminated when the target dose is reached.

42. An ionization radiation system that irradiates a substrate with a target dose of pulsed ionizing radiation during a treatment, said system comprising:
   a. a pulsed ionizing electron beam that is aimed at and deposited into the substrate, wherein the pulsed electron beam is provided as a train of one or more individual pulses, and wherein the pulsed electron beam comprises fluence characteristics as the treatment proceeds;
   b. a control system comprising at least one sensor that monitors the pulsed electron beam as the treatment proceeds, wherein the at least one sensor comprises a toroid sensor having a central bore, and wherein the pulsed beam of ionizing radiation passes through the central bore of the toroid sensor, and wherein:
      i. the toroid sensor provides an output signal indicative of the fluence characteristics of the pulsed electron beam the treatment proceeds;
      ii. the control system comprises program instructions that use information comprising the output signal to determine dose information indicative of the cumulative dose of the pulsed electron beam deposited into the substrate as the treatment proceeds;
      iii. the control system comprises program instructions that determine a pulse width modulation for at least one of the pulses using information comprising a comparison between the cumulative dose and the target dose;
      iv. the control system comprises program instructions that, as the target dose approaches as the treatment proceeds, proactively adjust a pulse duration of the pulsed ionizing radiation beam so that the cumulative dose deposited into the substrate matches the target dose when the depositing of the pulsed ionizing radiation into the substrate is terminated; and
      v. the control system comprises program instructions, that as the target dose approaches, issue a stop signal in advance of reaching the target dose that causes the depositing of the pulsed ionizing radiation into the substrate to be terminated when the target dose is reached.

* * * * *